US009573953B2

(12) United States Patent
Xi

(10) Patent No.: US 9,573,953 B2
(45) Date of Patent: Feb. 21, 2017

(54) HETEROAROMATIC COMPOUNDS AS PI3 KINASE MODULATORS AND METHODS OF USE

(71) Applicant: Ning Xi, Newbury Park, CA (US)

(72) Inventor: Ning Xi, Newbury Park, CA (US)

(73) Assignees: CALITOR SCIENCES, LLC, Newbury Park, CA (US); SUNSHINE LAKE PHARMA CO., LTD., Dongguan, Guangdong (CN)

(*) Notice: Subject to any disclaimer, the term of this patent is extended or adjusted under 35 U.S.C. 154(b) by 7 days.

(21) Appl. No.: 14/181,670

(22) Filed: Feb. 15, 2014

(65) Prior Publication Data

US 2014/0234254 A1  Aug. 21, 2014

Related U.S. Application Data

(60) Provisional application No. 61/767,721, filed on Feb. 21, 2013.

(51) Int. Cl.

| C07D 487/04 | (2006.01) |
| C07D 471/04 | (2006.01) |
| A61K 31/444 | (2006.01) |
| A61K 45/06 | (2006.01) |
| A61K 31/519 | (2006.01) |

(52) U.S. Cl.
CPC ........... *C07D 487/04* (2013.01); *A61K 31/444* (2013.01); *A61K 31/519* (2013.01); *A61K 45/06* (2013.01); *C07D 471/04* (2013.01)

(58) Field of Classification Search
CPC .................... C07D 487/04; C07D 471/04
See application file for complete search history.

(56) References Cited

U.S. PATENT DOCUMENTS

| 7,196,078 | B2 | 3/2007 | Guzi et al. |
| 7,238,808 | B2 | 7/2007 | McArthur et al. |
| 7,329,662 | B2 | 2/2008 | Wichmann et al. |
| 7,446,113 | B2 | 11/2008 | Gatti McArthur et al. |
| 7,514,443 | B2 | 4/2009 | Wichmann et al. |
| 7,550,470 | B2 | 6/2009 | Fraley |
| 7,718,661 | B2 | 5/2010 | Gatti McArthur et al. |
| 7,820,665 | B2 | 10/2010 | Booker et al. |
| 8,063,048 | B2 | 11/2011 | Gatti McArthur et al. |
| 8,591,943 | B2 | 11/2013 | Deng et al. |
| 8,883,801 | B2 | 11/2014 | Zhao et al. |
| 2010/0311736 | A1 | 12/2010 | Adams et al. |
| 2013/0035324 | A1 | 2/2013 | Ren et al. |

FOREIGN PATENT DOCUMENTS

| CN | 102675286 | 9/2012 |
| CN | 102924450 | 2/2013 |
| CN | 103570709 | 2/2014 |
| KR | 20130013264 | 2/2013 |
| WO | 2012156756 | 11/2012 |
| WO | 2012174312 | 12/2012 |
| WO | 2013147711 | 10/2013 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Protein Kinase [online], [retrieved on Aug. 9, 2008]. Retrieved from the internet, URL; http://en.wikipedia.org/wiki/Protein_kinase>.*
ISR of PCT/US2014/016643.
Written Opinion of PCT/US2014/016643.
Kim et al., Design and Synthesis of Imidazopyridine Analogues as Inhibitors of Phosphoinositide 3-Kinase Signaling and Angiogenesis, J. Med. Chem., 2011, vol. 54, Issue 7, p. 2455-2466.
Stec et al., Structure-Activity Relationships of Phosphoinositide 3-Kinase (PI3K)/Mammalian Target of Rapamycin (mTOR) Dual Inhibitors: Investigations of Various 6,5-Heterocycles to Improve Metabolic Stability, J. Med. Chem., 2011, vol. 54, Issue 14, p. 5174-5184.
Jeong et al., Selectivity Enhancement Arising from Interactions at the PI3K Unique Pocket, Chem. Med. Chem., 2012, vol. 7, Issue 8, p. 1379-1383.
Wang et al., Synthesis and anticancer activity evaluation of a series of [1,2,4]triazolo[1,5-a]pyridinylpyridines in vitro and in vivo, Eur. J. Med. Chem., 2013, vol. 67, p. 243-251.

* cited by examiner

*Primary Examiner* — Shawquia Jackson
(74) *Attorney, Agent, or Firm* — Kam W. Law; Squire Patton Boggs (US) LLP

(57) ABSTRACT

The present invention provides heteroaromatic derivatives and pharmaceutical acceptable salts and formulations thereof useful in modulating the protein kinase activity, especially phosphatidylinositol 3-kinases (PI3 kinases) and mTOR, and in modulating inter- and/or intra-cellular signaling activities such as proliferation, differentiation, apoptosis, migration and invasion. The invention also provides pharmaceutically acceptable compositions comprising such compounds and methods of using the compositions in the treatment of hyperproliferative disorders in mammals, especially humans.

15 Claims, No Drawings

HETEROAROMATIC COMPOUNDS AS PI3 KINASE MODULATORS AND METHODS OF USE

CROSS-REFERENCE TO RELATED APPLICATION

This application claims the benefit of U.S. Provisional Application Ser. No. 61/767,721, filed on Feb. 21, 2013, which is hereby incorporated by reference in its entirety.

FIELD OF THE INVENTION

The invention disclosed herein relates to the field of protein kinases and inhibitors thereof. In particular, the invention relates to modulators of phosphatidylinositol 3-kinases (PI3 kinases or PI3Ks) signaling pathways, and methods of use thereof.

BACKGROUND OF THE INVENTION

The phosphoinositide 3-kinases (PI3 kinases or PI3Ks), a family of lipid kinases, have been found to have key regulatory roles in many cellular processes including cell survival, proliferation and differentiation. As major effectors downstream of receptor tyrosine kinases (RTKs) and G protein-coupled receptors (GPCRs), PI3Ks transduce signals from various growth factors and cytokines into intracellular massages by generating phospholipids, which activate the serine-threonine protein kinase AKT (also known as protein kinase B (PKB)) and other downstream effector pathways. The tumor suppressor or PTEN (phosphatase and tensin homologue) is the most important negative regulator of the PI3K signaling pathway ("Small-molecule inhibitors of the PI3K signaling network" *Future Med. Chem.,* 2011, 3, 5, 549-565).

The phosphoinositide 3-kinase (PI3K) pathway is an important signal transduction pathway commonly activated in cancer. Activated PI3K pathway leads to phosphorylation of phosphatidylinositol-4,5-bisphosphate (PIP2) to generate phosphatidylinositol-3,4,5-trisphosphate (PIP3). PIP3 can be dephosphorylated by the phosphatase and tensin homolog (PTEN), which terminates PI3K signaling. The accumulation of PIP3 activates a signaling cascade starting with the phosphorylation (activation) of the protein serine-threonine kinase AKT at threonine 308 by phosphoinositide-dependent kinase 1 (PDK1). Phosphotylated AKT activates the mammalian target of rapamycin (mTOR), which leads to phosphorylation of its downstream targets.

There are three PI3K classes, with different structures and characteristics. Class I can be further subdivided into class Ia and class Ib. Class II PI3Ks are large (170-210 kDa) proteins that have a catalytic domains that mediate calcium/lipid binding in classical protein kinase C isoforms. Class III PI3Ks are typified by the yeast protein encoded by the VPS34 gene and phosphorylate only PtdIns to produce PtdIns(3)P and they are thought to regulate vesicle transport ("Targeting PI3K signaling in cancer: opportunities, challenges and limitations" *Nature Review Cancer,* 2009, 9, 550).

Class Ia PI3Ks (PI3Kα, PI3Kβ, PI3Kγ and PI3Kδ) comprise heterodimers between a p110 catalytic subunit (p110α, p110β, p110γ and p110δ respectively), and a p85 regulatory adapter subunit (i.e., p85α, p85β, p55δ, p55α and p50α). The catalytic p110 subunit uses ATP to phosphorylate PtdIns, PtdIns4P and PtdIns(4,5)P2. The importance of Class Ia PI3Ks in cancer was confirmed by the discovery that the PI3K catalytic subunit α-isoform gene (PIK3CA), which encodes p110α, is frequently mutated or amplified in a number of human tumors such as ovarian cancer (Campbell et al., *Cancer Res.,* 2004, 64, 7678-7681; Levine et al., *Clin. Cancer Res.,* 2005, 11, 2875-2878; Wang et al., *Hum. Mutat.,* 2005, 25, 322; Lee et al., *Gynecol. Oncol.,* 2005, 97, 26-34), cervical cancer, breast cancer (Bachman et al., *Cancer Biol., Ther.,* 2004, 3, 772-775; Levine et al., supra; Li et al., *Breast Cancer Res. Treat.,* 2006, 96, 91-95; Saal et al., *Cancer Res.,* 2005, 65, 2554-2559; Samuels and Velculescu, *Cell Cycle,* 2004, 3, 1221-1224), colorectal cancer (Samuels et al., *Science,* 2004, 304, 554; Velho et al., *Eur. J. Cancer,* 2005, 41, 1649-1654), endometrial cancer (Oda et al., *Cancer Res.,* 2005, 65, 10669-10673), gastric carcinomas (Byun et al., *M. J. Cancer,* 2003, 104, 318-327; Li et al., supra; Velho et al., supra; Lee et al., *Oncogene,* 2005, 24, 1477-1480), hepatocellular carcinoma (Lee et al., id), small and non-small cell lung cancer (Tang et al., *Lung Cancer* 2006, J1, 181-191; Massion et al., *Am. J. Respir. Crit. Care Med.,* 2004, 170, 1088-1094), thyroid carcinoma (Wu et al., *J. Clin. Endocrinol. Metab.,* 2005, 90, 4688-4693), acute myelogenous leukemia (AML) (Sujobert et al., *Blood,* 1997, 106, 1063-1066), chronic myelogenous leukemia (CML) (Hickey et al., *J. Biol. Chem.,* 2006, 281, 2441-2450), and glioblastomas (Hartmann et al., *Acta Neuropathol (Berl),* 2005, 109, 639-642; Samuels et al., supra).

mTOR is a highly conserved serine-threonine kinase with lipid kinase activity and participates as an effector in the PI3K/AKT pathway. mTOR exists in two distinct complexes, mTORC1 and mTORC2, and plays an important role in cell proliferation by monitoring nutrient availability and cellular energy levels. The downstream targets of mTORC1 are ribosomal protein S6 kinase 1 and eukaryotic translation initiation factor 4E-binding protein 1, both of which are crucial to the regulation of protein synthesis. ("Present and future of PI3K pathway inhibition in cancer: perspectives and limitations" *Current Med. Chem.,* 2011, 18, 2647-2685).

Knowledge about consequences of dysregulated mTOR signaling for tumorigenesis comes mostly from studies of pharmacologically disruption of mTOR by repamycin and its analogues such as temsirolimus (CCI-779) and everolimus (RAD001). Rapamycin was found to inhibit mTOR and thereby induce G1 arrest and apoptosis. The mechanism of rapamycin growth inhibition was found to be related to formation of complexes of rapamycin with FK-binding protein 12 (FKBP-12). These complexes then bound with high affinity to mTOR, preventing activation and resulting in inhibition of protein translation and cell growth. Cellular effects of mTOR inhibition are even more pronounced in cells that have concomitant inactivation of PTEN. Antitumor activity of rapamycin was subsequently identified, and a number of rapamycin analogues such as temsirolimus and everolimus have been approved by the US Food and Drug Administration for the treatment certain types of cancer.

In view of the important role of PI3Ks and mTOR in biological processes and disease states, inhibitors of these kinases are desirable ("Phosphatidylinositol 3-kinase isoforms as a novel drug targets" *Current Drug Targets,* 2011, 12, 1056-1081; "Progress in the preclinical discovery and clinical development of class I and dual class I/IV phosphoinositide 3-kinase (PI3K) inhibitors" *Current Med. Chem.,* 2011, 18, 2686-2714).

SUMMARY OF THE INVENTION

The following only summarizes certain aspects of the invention and is not intended to be limiting in nature. These aspects and other aspects and embodiments are described more fully below. All references cited in this specification are hereby incorporated by reference in their entirety. In the event of a discrepancy between the express disclosure of this specification and the references incorporated by reference, the express disclosure of this specification shall control.

Provided herein are compounds that inhibit, regulate, and/or modulate PI3K and/or mTOR, and are useful in the treatment of hyperproliferative diseases, such as cancer, in humans. Also provided herein are methods of making the compound, methods of using such compounds in the treatment of hyperproliferative diseases in humans and pharmaceutical compositions containing such compounds.

The first aspect of the invention provides a compound having Formula (I):

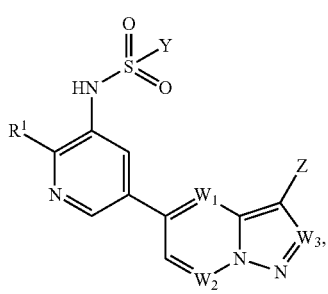

(I)

or a stereoisomer, a geometric isomer, a tautomer, an N-oxide, a solvate, a metabolite, a pharmaceutically salt or a prodrug thereof, wherein each of Y, $R^1$, Z, $W_1$, $W_2$ and $W_3$ is as defined herein.

In certain embodiments, each of $W_1$, $W_2$ and $W_3$ is independently N or $CR^c$;

Z is D, CN, $N_3$, or

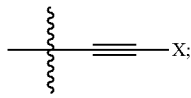

X is H, D, $(C_1-C_6)$alkyl, $(C_3-C_6)$cycloalkyl, $(C_3-C_6)$heterocyclyl, —$(C_1-C_4)$alkylene-$(C_3-C_6)$cycloalkyl, —$(C_1-C_4)$alkylene-$(C_3-C_6)$heterocyclyl, $(C_6-C_{10})$aryl, or 5-10 membered heteroaryl comprising 1, 2, 3 or 4 heteroatoms independently selected from O, S and N, wherein each of the $(C_1-C_6)$alkyl, $(C_3-C_6)$cycloalkyl, $(C_3-C_6)$heterocyclyl, —$(C_1-C_4)$alkylene-$(C_3-C_6)$cycloalkyl, —$(C_1-C_4)$alkylene-$(C_3-C_6)$heterocyclyl, $(C_6-C_{10})$aryl and 5-10 membered heteroaryl is optionally substituted with 1, 2, 3 or 4 substituents independently selected from D, F, Cl, Br, CN, $N_3$, $OR^a$, $SR^a$, $NR^aR^b$, —C(=O)$NR^aR^b$, $(C_1-C_6)$alkyl, $(C_1-C_6)$haloalkyl, $(C_2-C_6)$alkenyl, $(C_2-C_6)$alkynyl, —$(C_1-C_4)$alkylene-CN, —$(C_1-C_4)$alkylene-$OR^a$, —$(C_1-C_4)$alkylene-$NR^aR^b$, $(C_6-C_{10})$aryl, and 5-10 membered heteroaryl;

Y is $(C_1-C_6)$alkyl, $(C_3-C_6)$cycloalkyl, $(C_3-C_6)$heterocyclyl, —$(C_1-C_4)$alkylene-$(C_3-C_6)$cycloalkyl, —$(C_1-C_4)$alkylene-$(C_3-C_6)$heterocyclyl, $(C_2-C_6)$alkenyl, $(C_2-C_6)$alkynyl, $(C_6-C_{10})$aryl, or 5-10 membered heteroaryl comprising 1, 2, 3 or 4 heteroatoms independently selected from O, S and N, wherein each of the $(C_1-C_6)$alkyl, $(C_3-C_6)$cycloalkyl, $(C_3-C_6)$heterocyclyl, —$(C_1-C_4)$alkylene-$(C_3-C_6)$cycloalkyl, —$(C_1-C_4)$alkylene-$(C_3-C_6)$heterocyclyl, $(C_2-C_6)$alkenyl, $(C_2-C_6)$alkynyl, $(C_6-C_{10})$aryl and 5-10 membered heteroaryl is optionally substituted with 1, 2, 3 or 4 substituents independently selected from D, F, Cl, Br, CN, $N_3$, $OR^a$, $SR^a$, $NR^aR^b$, —C(=O)$NR^aR^b$, $(C_1-C_6)$alkyl, $(C_1-C_6)$haloalkyl, $(C_2-C_6)$alkenyl, $(C_2-C_6)$alkynyl, —$(C_1-C_4)$alkylene-CN, —$(C_1-C_4)$alkylene-$OR^a$, —$(C_1-C_4)$alkylene-$NR^aR^b$, $(C_6-C_{10})$aryl, and 5-10 membered heteroaryl;

$R^1$ is H, D, Cl, $OR^a$, $NR^aR^b$, $(C_1-C_6)$aliphatic, or $(C_3-C_6)$cycloalkyl, wherein each of the $(C_1-C_6)$aliphatic and $(C_3-C_6)$cycloalkyl is optionally substituted with 1, 2, 3 or 4 substituents independently selected from D, F, Cl, CN, $N_3$, $OR^a$, $SR^a$, and $NR^aR^b$;

each $R^a$ and $R^b$ is independently H, $(C_1-C_6)$alkyl, $(C_3-C_6)$cycloalkyl, $(C_3-C_6)$heterocyclyl, $(C_6-C_{10})$aryl, 5-10 membered heteroaryl comprising 1, 2, 3 or 4 heteroatoms independently selected from O, S and N, —$(C_1-C_4)$alkylene-$(C_6-C_{10})$aryl, —$(C_1-C_4)$alkylene-(5-10 membered heteroaryl), or $R^a$ and $R^b$ are taken together with the nitrogen atom to which they are attached form a 3-8 membered heterocyclic ring, wherein each of the above substituents is optionally substituted with 1, 2, 3 or 4 substituents independently selected from D, F, Cl, CN, $N_3$, OH, $NH_2$, $(C_1-C_6)$alkoxy, and $(C_1-C_6)$alkylamino; and each $R^c$ is independently H, D, F, Cl, Br, I, $N_3$, CN, OH, $NH_2$, $(C_1-C_6)$alkyl, $(C_1-C_6)$alkoxy, $(C_1-C_6)$alkylamino, $(C_3-C_6)$cycloalkyl, $(C_3-C_6)$heterocyclyl, $(C_6-C_{10})$aryl, or 5-10 membered heteroaryl comprising 1, 2, 3 or 4 heteroatoms independently selected from O, S and N, wherein each of the $(C_1-C_6)$alkyl, $(C_1-C_6)$alkoxy, $(C_1-C_6)$alkylamino, $(C_3-C_6)$cycloalkyl, $(C_3-C_6)$heterocyclyl, $(C_6-C_{10})$aryl and 5-10 membered heteroaryl is optionally substituted with 1, 2, 3 or 4 substituents independently selected from D, F, Cl, CN, $N_3$, OH, $NH_2$, $(C_1-C_6)$alkyl, $(C_3-C_6)$cycloalkyl, $(C_1-C_6)$haloalkyl, $(C_1-C_6)$alkoxy, and $(C_1-C_6)$alkylamino.

In another embodiment, $W_1$ is N or $CR^c$; and each of $W_2$ and $W_3$ is independently $CR^c$.

In another embodiment, Z is CN, $N_3$, or

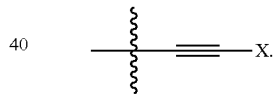

In another embodiment, X is H, D, $(C_1-C_6)$alkyl, $(C_3-C_6)$cycloalkyl, $(C_3-C_6)$heterocyclyl, —$(C_1-C_4)$alkylene-$(C_3-C_6)$cycloalkyl, or —$(C_1-C_4)$alkylene-$(C_3-C_6)$heterocyclyl, wherein each of the $(C_1-C_6)$alkyl, $(C_3-C_6)$cycloalkyl, $(C_3-C_6)$heterocyclyl, —$(C_1-C_4)$alkylene-$(C_3-C_6)$cycloalkyl and —$(C_1-C_4)$alkylene-$(C_3-C_6)$heterocyclyl is optionally substituted with 1, 2, 3 or 4 substituents independently selected from D, F, Cl, Br, CN, $N_3$, $OR^a$, $SR^a$, $NR^aR^b$, —C(=O)$NR^aR^b$, $(C_1-C_3)$alkyl, $(C_1-C_3)$haloalkyl, $(C_2-C_4)$alkenyl, and $(C_2-C_4)$alkynyl.

In another embodiment, Y is $(C_1-C_6)$alkyl, $(C_3-C_6)$cycloalkyl, $(C_2-C_6)$alkenyl, $(C_2-C_6)$alkynyl, $(C_6-C_{10})$aryl, or 5-10 membered heteroaryl comprising 1, 2, 3 or 4 heteroatoms independently selected from O, S and N, wherein each of the $(C_1-C_6)$alkyl, $(C_3-C_6)$cycloalkyl, $(C_2-C_6)$alkenyl, $(C_2-C_6)$alkynyl, $(C_6-C_{10})$aryl and 5-10 membered heteroaryl is optionally substituted with 1, 2, 3 or 4 substituents independently selected from D, F, Cl, Br, CN, $N_3$, $OR^a$, $SR^a$, $NR^aR^b$, —C(=O)$NR^aR^b$, $(C_1-C_3)$alkyl, $(C_1-C_3)$haloalkyl, $(C_2-C_4)$alkynyl, $(C_6-C_{10})$aryl, and 5-10 membered heteroaryl.

In another embodiment, $R^1$ is H, D, Cl, $CH_3$, $CH_2CH_3$, $CF_3$, $CH_2CF_3$, $OCH_3$, or $OCH_2CH_3$.

In another embodiment, each $R^c$ is independently H, D, F, Cl, $N_3$, CN, $NH_2$, $(C_1-C_3)$alkyl, $(C_1-C_3)$alkoxy, $(C_1-C_3)$ alkylamino, $(C_3-C_6)$cycloalkyl, or $(C_3-C_6)$heterocyclyl, wherein each of the $(C_1-C_3)$alkyl, $(C_1-C_3)$alkoxy, $(C_1-C_3)$alkylamino, $(C_3-C_6)$cycloalkyl and $(C_3-C_6)$heterocyclyl is optionally substituted with 1, 2, 3 or 4 substituents independently selected from D, F, CN, $N_3$, OH, $NH_2$, $(C_1-C_3)$alkyl, $(C_3-C_6)$cycloalkyl, and $(C_1-C_3)$haloalkyl.

In another aspect, provided herein are pharmaceutical compositions comprising a compound disclosed herein, or a stereoisomer, geometric isomer, tautomer, solvate, metabolite, pharmaceutically acceptable salt or prodrug thereof, and an optional pharmaceutically acceptable carrier, excipient, diluent, adjuvant, vehicle or a combination thereof. In certain embodiments, the compound is a modulator of PI3K.

In some embodiments, the pharmaceutical composition disclosed herein further comprises an additional therapeutic agent. In other embodiments, the therapeutic agent is a chemotherapeutic agent, an anti-proliferative agent, an agent for treating atherosclerosis, an agent for treating lung fibrosis or a combination thereof.

In certain embodiments, the therapeutic agent is chlorambucil, melphalan, cyclophosphamide, ifosfamide, busulfan, carmustine, lomustine, streptozocin, cisplatin, carboplatin, oxaliplatin, dacarbazine, temozolomide, procarbazine, methotrexate, fluorouracil, cytarabine, gemcitabine, mercaptopurine, fludarabine, vinblastine, vincristine, vinorelbine, paclitaxel, docetaxel, topotecan, irinotecan, etoposide, trabectedin, dactinomycin, doxorubicin, epirubicin, daunorubicin, mitoxantrone, bleomycin, mitomycin, ixabepilone, tamoxifen, flutamide, gonadorelin analogues, megestrol, prednidone, dexamethasone, methylprednisolone, thalidomide, interferon alfa, leucovorin, sirolimus, temsirolimus, everolimus, afatinib, alisertib, amuvatinib, apatinib, axitinib, bortezomib, bosutinib, brivanib, cabozantinib, cediranib, crenolanib, crizotinib, dabrafenib, dacomitinib, danusertib, dasatinib, dovitinib, erlotinib, foretinib, ganetespib, gefitinib, ibrutinib, icotinib, imatinib, iniparib, lapatinib, lenvatinib, linifanib, linsitinib, masitinib, momelotinib, motesanib, neratinib, nilotinib, niraparib, oprozomib, olaparib, pazopanib, pictilisib, ponatinib, quizartinib, regorafenib, rigosertib, rucaparib, ruxolitinib, saracatinib, saridegib, sorafenib, sunitinib, tasocitinib, telatinib, tivantinib, tivozanib, tofacitinib, trametinib, vandetanib, veliparib, vemurafenib, vismodegib, volasertib, alemtuzumab, bevacizumab, brentuximab vedotin, catumaxomab, cetuximab, denosumab, gemtuzumab, ipilimumab, nimotuzumab, ofatumumab, panitumumab, ramucirumab, rituximab, tositumomab, trastuzumab, or a combination thereof.

In another aspect, provided herein are methods for preventing, managing, treating or lessening the severity of a proliferative disorder in a patient infected with the proliferative disorder, which comprises administrating a pharmaceutically effective amount of the compound disclosed herein, or the pharmaceutical composition disclosed herein to the patient.

In another aspect, provided herein is use of the compound disclosed herein, or the pharmaceutical composition disclosed herein in the manufacture of a medicament for preventing, managing, treating or lessening the severity of a proliferative disorder in a patient.

In some embodiments, the proliferative disorder is metastatic cancer. In other embodiments, the proliferative disorder is colon cancer, gastric adenocarcinoma, bladder cancer, breast cancer, kidney cancer, liver cancer, lung cancer, skin cancer, thyroid cancer, cancer of the head and neck, prostate cancer, pancreatic cancer, cancer of the CNS, glioblastoma or a myeloproliferative disorder. In further embodiments, the proliferative disorder is atherosclerosis or lung fibrosis.

In another aspect, provided herein is a method of inhibiting or modulating PI3K and/or mTOR activity in a biological sample comprising contacting a biological sample with the compound disclosed herein, or the pharmaceutical composition disclosed herein.

In some embodiments, provided herein is a method of inhibiting or modulating PI3K or mTOR, the method comprising contacting the kinase with the compound according to the present invention, or with the composition according to the present invention. In some embodiments, the invention provides a method of inhibiting or modulating PI3K or mTOR signaling, the method comprising contacting the receptor with the compound according to the present invention, or with the composition according to the present invention. In some embodiments, inhibition or modulation of PI3K or mTOR activity can be in a cell or a multicellular organism. If in a multicellular organism, the method according to this aspect of the invention comprises administering to the organism the compound according to the present invention, or the composition according to the present invention. In some embodiments, the organism is a mammal. In other embodiments is a human. In still other embodiment, the method further comprises contacting the kinase with an additional therapeutic agent.

In another aspect, provided herein is a method of inhibiting proliferative activity of a cell, the method comprising contacting the cell with an effective proliferative inhibiting amount of a compound according to the present invention or a composition thereof. In some embodiments, the method further comprises contacting the cell with an additional therapeutic agent.

In another aspect, provided herein is a method of treating a cell proliferative disease in a patient, the method comprising administering to the patient in need of such treatment an effective therapeutic amount of the compound according to the present invention or the composition thereof. In some embodiments, the method further comprises administering an additional therapeutic agent.

In some embodiments, provided herein is a method of inhibiting tumor growth in a patient, the method comprising administering to the patient in need thereof an effective therapeutic amount of the compound according to the present invention or the composition thereof. In some embodiments, the method further comprises administering an additional therapeutic agent.

In another aspect, provided herein includes methods of preparing, methods of separating, and methods of purifying compounds of Formula (I).

The foregoing merely summarizes certain aspects of the invention and is not intended to be limiting in nature. These aspects and other aspects and embodiments are described more fully below.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable sub combination.

Unless defined otherwise, all technical and scientific terms used herein have the same meaning as is commonly understood by one of skill in the art to which this invention belongs. All patents and publications referred to herein are incorporated by reference.

As used herein, the following definitions shall apply unless otherwise indicated. For purposes of this invention, the chemical elements are identified in accordance with the Periodic Table of the Elements, CAS version, and the Handbook of Chemistry and Physics, 75$^{th}$ Ed. 1994. Additionally, general principles of organic chemistry are described in Sorrell et al., "Organic Chemistry", University Science Books, Sausalito: 1999, and Smith et al., "March's Advanced Organic Chemistry", John Wiley & Sons, New York: 2007, all of which are incorporated by reference in their entireties.

The grammatical articles "a", "an" and "the", as used herein, are intended to include "at least one" or "one or more" unless otherwise indicated herein or clearly contradicted by the context. Thus, the articles are used herein to refer to one or more than one (i.e. at least one) of the grammatical objects of the article. By way of example, "a component" means one or more components, and thus, possibly, more than one component is contemplated and may be employed or used in an implementation of the described embodiments.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, "patient" refers to a human (including adults and children) or other animal. In one embodiment, "patient" refers to a human.

The term "comprising" is meant to be open ended, including the indicated component but not excluding other elements.

"Stereoisomers" refers to compounds which have identical chemical constitution, but differ with regard to the arrangement of the atoms or groups in space. Stereoisomers include enantiomer, diastereomers, conformer (rotamer), geometric (cis/trans) isomer, atropisomer, etc.

"Chiral" refers to molecules which have the property of non-superimposability of the mirror image partner, while the term "achiral" refers to molecules which are superimposable on their mirror image partner.

"Enantiomers" refer to two stereoisomers of a compound which are non-superimposable mirror images of one another.

"Diastereomer" refers to a stereoisomer with two or more centers of chirality and whose molecules are not mirror images of one another. Diastereomers have different physical properties, e.g. melting points, boiling points, spectral properties or biological activities. Mixture of diastereomers may separate under high resolution analytical procedures such as electrophoresis and chromatography such as HPLC.

Stereochemical definitions and conventions used herein generally follow Parker et al., McGraw-Hill Dictionary of Chemical Terms (1984) McGraw-Hill Book Company, New York and Eliel et al., "Stereochemistry of Organic Compounds", John Wiley & Sons, Inc., New York, 1994.

Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may be referred to as an enantiomer, and a mixture of such stereoisomers is called an enantiomeric mixture. A 50:50 mixture of enantiomers is referred to as a racemic mixture or a racemate, which may occur where there has been no stereoselection or stereospecificity in a chemical reaction or process.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Any resulting mixtures of stereoisomers can be separated on the basis of the physicochemical differences of the constituents, into the pure or substantially pure geometric isomers, enantiomers, diastereomers, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., "Enantiomers, Racemates and Resolutions," Wiley Interscience, New York, 1981; Gawley et al., "Principles of Asymmetric Synthesis," 2$^{nd}$ Ed. Elsevier, Oxford, UK, 2012; Eliel et al., Stereochemistry of Carbon Compounds, McGraw-Hill, NY, 1962; Wilen et al., "Tables of Resolving Agents and Optical Resolutions," p. 268 (E. L. Eliel, Ed., Univ. of Notre Dame Press, Notre Dame, Ind., 1972) and Subramanian et al., "Chiral Separation Techniques: A Practical Approach," Ed., Wiley-VCH Verlag GmbH & Co. KGaA, Weinheim, Germany, 2007.

The term "tautomer" or "tautomeric form" refers to structural isomers of different energies which are interconvertible via a low energy barrier. Where tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers. Unless otherwise stated, all tautomeric forms of the compounds disclosed herein are within the scope of the invention.

As described herein, the compounds disclosed herein may optionally be substituted with one or more substituents, such as those illustrated below, or as exemplified by particular classes, subclasses, and species of the invention. It will be appreciated that the phrase "optionally substituted" is used interchangeably with the phrase "substituted or unsubstituted". In general, the term "substituted" whether proceeded by the term "optionally" or not, refers to the replacement of one or more hydrogen radicals in a given structure with the radical of a specified substituent. The term "optional" or "optionally" means that the subsequently described event or circumstance may but need not occur, and that the description includes instances where the event or circumstance occurs and instances in which it does not. Unless otherwise indicated, an optionally substituted group may have a substituent at each substitutable position of the group. When more than one position in a given structure can be substituted with more than one substituent selected from a specified group, the substituent may be either the same or different at each position.

At various places in the present specification, substituents of compounds disclosed herein are disclosed in groups or in ranges. It is specifically intended that the invention include each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "alkyl" or "alkyl group" refers to a saturated linear or branched-chain monovalent hydrocarbon radical of 1 to 20 carbon atoms. Unless otherwise specified, the alkyl group contains 1-20 carbon atoms. In some embodiments, the alkyl group contains 1-10 carbon atoms. In other embodiments, the alkyl group contains 1-8 carbon atoms. In still other embodiments, the alkyl group contains 1-6 carbon atoms. In yet other embodiments, the alkyl group contains 1-4 carbon atoms, and in further embodiments, the alkyl group contains 1-3 carbon atoms.

Some non-limiting examples of the alkyl group include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like. The alkyl group herein is optionally substituted independently with one or more substituents described herein.

The prefix "alk-" is inclusive of both straight chain and branched saturated carbon chain.

The term "alkylene" refers to a saturated divalent hydrocarbon group derived from a straight or branched chain saturated hydrocarbon by the removal of two hydrogen atoms. Unless otherwise specified, the alkylene group contains 1-10 carbon atoms. In some embodiments, the alkylene group contains 1-6 carbon atoms. In other embodiments, the alkylene group contains 1-4 carbon atoms. In still other embodiments, the alkylene group contains 1-3 carbon atoms, and in yet other embodiments, the alkylene group contains 1-2 carbon atoms Some non-limiting examples of the alkylene group include methylene (—$CH_2$—), ethylene (—$CH_2CH_2$—), isopropylene (—$CH(CH_3)CH_2$—), and the like.

The term "alkenyl" refers to a linear or branched-chain monovalent hydrocarbon radical of 2 to 12 carbon atoms with at least one site of unsaturation, i.e., a carbon-carbon, sp2 double bond, wherein the alkenyl radical may be optionally substituted independently with one or more substituents described herein, and includes radicals having "cis" and "trans" orientations, or alternatively, "E" and "Z" orientations. In some embodiments, the alkenyl group contains 2-8 carbon atoms. In other embodiments, the alkenyl group contains 2-6 carbon atoms. In still other embodiments, the alkenyl group contains 2-4 carbon atoms. Some non-limiting examples of the alkenyl group include ethylenyl or vinyl (—CH=$CH_2$), allyl (—$CH_2$CH=$CH_2$), and the like.

The term "alkynyl" refers to a linear or branched-chain monovalent hydrocarbon radical of 2 to 12 carbon atoms with at least one site of unsaturation, i.e., a carbon-carbon, sp triple bond, wherein the alkynyl radical may be optionally substituted independently with one or more substituents described herein. In some embodiments, the alkynyl group contains 2-8 carbon atoms. In other embodiments, the alkynyl group contains 2-6 carbon atoms. In still other embodiments, the alkynyl group contains 2-4 carbon atoms. Some non-limiting examples of the alkynyl group include ethynyl (—C≡CH), propynyl (propargyl, —$CH_2$C≡CH), —C≡C—$CH_3$, and the like.

The term "aliphatic" or "aliphatic group" refers to a straight-chain (i.e., unbranched) or branched, substituted or unsubstituted hydrocarbon chain that is completely saturated or that contains one or more units of unsaturation. Unless otherwise specified, the aliphatic group contains 1-20 carbon atoms. In some embodiments, the aliphatic group contains 1-10 carbon atoms. In other embodiments, the aliphatic group contains 1-8 carbon atoms. In still other embodiments, the aliphatic group contains 1-6 carbon atoms. In yet other embodiments, the aliphatic group contains 1-4 carbon atoms. In still other embodiments, the aliphatic group contains 1-3 carbon atoms, and in yet other embodiments, the aliphatic group contains 1-2 carbon atoms. Some non-limiting examples of the aliphatic group include linear or branched, substituted or unsubstituted alkyl, alkenyl, or alkynyl groups. For example, ($C_1$-$C_6$)aliphatic groups include unbranched or branched, unsubstituted or suitably substituted ($C_1$-$C_6$)alkyl, ($C_2$-$C_6$)alkenyl or ($C_2$-$C_6$)alkynyl groups. The aliphatic group herein is optionally substituted independently with one or more substituents described herein.

The term "alkoxy" refers to an alkyl group, as previously defined, attached to the principal carbon atom through an oxygen atom. Unless otherwise specified, the alkoxy group contains 1-20 carbon atoms. In some embodiments, the alkoxy group contains 1-10 carbon atoms. In other embodiments, the alkoxy group contains 1-8 carbon atoms. In still other embodiments, the alkoxy group contains 1-6 carbon atoms. In yet other embodiments, the alkoxy group contains 1-4 carbon atoms, and in further embodiments, the alkoxy group contains 1-3 carbon atoms.

Some non-limiting examples of the alkoxy group include methoxy (MeO, —$OCH_3$), ethoxy (EtO, —$OCH_2CH_3$), 1-propoxy (n-PrO, n-propoxy, —$OCH_2CH_2CH_3$), 2-propoxy (i-PrO, i-propoxy, —$OCH(CH_3)_2$), 1-butoxy (n-BuO, n-butoxy, —$OCH_2CH_2CH_2CH_3$), 2-methyl-1-propoxy (i-BuO, i-butoxy, —$OCH_2CH(CH_3)_2$), 2-butoxy (s-BuO, s-butoxy, —$OCH(CH_3)CH_2CH_3$), 2-methyl-2-propoxy (t-BuO, t-butoxy, —$OC(CH_3)_3$), 1-pentoxy (n-pentoxy, —$OCH_2CH_2CH_2CH_2CH_3$), 2-pentoxy (—$OCH(CH_3)$ $CH_2CH_2CH_3$), 3-pentoxy (—$OCH(CH_2CH_3)_2$), 2-methyl-2-butoxy (—$OC(CH_3)_2CH_2CH_3$), 3-methyl-2-butoxy (—$OCH(CH_3)CH(CH_3)_2$), 3-methyl-1-butoxy (—$OCH_2CH_2CH(CH_3)_2$), 2-methyl-1-butoxy (—$OCH_2CH$ ($CH_3$)$CH_2CH_3$), and the like. The alkoxy group herein is optionally substituted independently with one or more substituents described herein.

The term "haloalkyl", "haloalkenyl" or "haloalkoxy" refers to alkyl, alkenyl, or alkoxy, as the case may be, substituted with one or more halogen atoms.

The term "alkylamino" embraces "N-alkylamino" and "N,N-dialkylamino" where amino groups are independently substituted with one alkyl radical or with two alkyl radicals, respectively. More preferred alkylamino radicals are "lower alkylamino" radicals having one or two alkyl radicals of one to six carbon atoms, attached to a nitrogen atom. Suitable alkylamino radicals may be mono or dialkylamino such as N-methylamino, N-ethylamino, N,N-dimethylamino, N,N-diethylamino and the like. The alkylamino group herein is optionally substituted independently with one or more substituents described herein.

The term "arylamino" refers to amino groups, which have been substituted with one or two aryl radicals, such as N-phenylamino. The arylamino radicals may be further substituted on the aryl ring portion of the radical.

The term "aminoalkyl" refers to linear or branched alkyl radicals having one to about ten carbon atoms any one of which may be substituted with one or more amino radicals. More preferred aminoalkyl radicals are "lower aminoalkyl" radicals having 1-6 carbon atoms and one or more amino radicals. Some non-limiting examples of the aminoalkyl group include aminomethyl, aminoethyl, aminopropyl, aminobutyl and aminohexyl.

The term "carbocycle", "carbocyclyl", or "carbocyclic ring" refers to a monovalent or multivalent non-aromatic, saturated or partially unsaturated ring having 3 to 12 carbon atoms as a monocyclic, bicyclic or tricyclic ring system. The carbobicyclyl system includes a spiro carbobicyclyl or a fused carbobicyclyl. Some non-limiting examples of the carbocyclyl group include cycloalkyl, cycloalkenyl, and cycloalkynyl. Further non-limiting examples of the carbocyclyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, and the like.

The term "cycloalkyl" refers to a monovalent or multivalent saturated ring having 3 to 12 carbon atoms as a monocyclic, bicyclic, or tricyclic ring system. Unless otherwise specified, the cycloalkyl contains 3-12 carbon atoms. In some embodiments, the cycloalkyl contains 3-8 carbon atoms. In other embodiments, the cycloalkyl contains 3-6 carbon atoms. The cycloalkyl radical is optionally substituted independently with one or more substituents described herein.

The term "heterocycle", "heterocyclyl" or "heterocyclic" as used interchangeably herein refers to a monocyclic, bicyclic, or tricyclic ring system in which one or more ring members are an independently selected heteroatom and that is completely saturated or that contains one or more units of unsaturation, but not aromatic, having one or more points of attachment to the rest of the molecule. One or more ring atoms are optionally substituted independently with one or more substituents described herein. In some embodiments, the "heterocycle", "heterocyclyl", or "heterocyclic" group is a monocycle having 3 to 7 ring members (2 to 6 carbon atoms and 1 to 3 heteroatoms selected from N, O, P, and S, wherein the S or P is optionally substituted with one or more oxo to provide the group SO or $SO_2$, PO or $PO_2$). In other embodiments, it is a monocycle having 3 to 6 ring members (2 to 5 carbon atoms and 1 to 3 heteroatoms selected from N, O, P, and S, wherein the S or P is optionally substituted with one or more oxo to provide the group SO or $SO_2$, PO or $PO_2$) or a bicycle having 7 to 10 ring members (4 to 9 carbon atoms and 1 to 3 heteroatoms selected from N, O, P, and S, wherein the S or P is optionally substituted with one or more oxo to provide the group SO or $SO_2$, PO or $PO_2$).

The heterocyclyl may be a carbon radical or heteroatom radical. Some non-limiting examples of the heterocyclic ring include pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homo-piperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, and 1,2,3,4-tetrahydro iso-quinolinyl. Some non-limiting examples of the heterocyclic group wherein 2 ring carbon atoms are substituted with oxo (=O) moieties are pyrimidindionyl and 1,1-dioxo-thiomorpholinyl.

The term "heteroatom" refers to one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or NR (as in N-substituted pyrrolidinyl).

The term "halogen" refers to Fluoro (F), Chloro (Cl), Bromo (Br), or Iodo (I).

The term "H" denotes a single hydrogen atom. This radical may be attached, for example, to an oxygen atom to form a hydroxyl radical.

The term "D" or "²H" denotes a single deuterium atom. One of this radical may be attached, for example, to a methyl group to form a mono-deuterated methyl group (CDH₂), two of deuterium atoms may be attached to a methyl group to form a di-deuterated methyl (CD₂H), and three of deuterium atoms may be attached to a methyl group to form a tri-deuterated methyl group (CD₃).

The term "azido" or "N₃" refers to an azide moiety. This radical may be attached, for example, to a methyl group to form azidomethane (methyl azide, MeN₃); or attached to a phenyl group to form phenyl azide (PhN₃).

The term "aryl" refers to monocyclic, bicyclic, and tricyclic carbocyclic ring systems having a total of 6 to 14 ring members, preferably, 6 to 12 ring members, and more preferably 6 to 10 ring members, wherein at least one ring in the system is aromatic, wherein each ring in the system contains 3 to 7 ring members and that has one or more points of attachment to the rest of the molecule. The term "aryl" may be used interchangeably with the term "aryl ring" or "aromatic ring". Some non-limiting examples of the aryl group include phenyl, naphthyl, and anthracene. The aryl radical is optionally substituted independently with one or more substituents described herein.

The term "heteroaryl" refers to monocyclic, bicyclic, and tricyclic ring systems having a total of 5 to 14 ring members, preferably, 5 to 12 ring members, and more preferably 5 to 10 ring members, wherein at least one ring in the system is aromatic, and at least one aromatic ring in the system contains one or more heteroatoms, wherein each ring in the system contains 5 to 7 ring members and that has one or more points of attachment to the rest of the molecule. The term "heteroaryl" may be used interchangeably with the term "heteroaryl ring" or the term "heteroaromatic ring". In some embodiments, the 5-10 membered heteroaryl comprises 1, 2, 3 or 4 heteroatoms independently selected from O, S and N. In other embodiments, the 5-6 membered heteroaryl comprises 1, 2, 3 or 4 heteroatoms independently selected from O, S and N. The heteroaryl radical is optionally substituted independently with one or more substituents described herein.

Some non-limiting examples of the heteroaryl group include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,3,4-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl or 4-isoquinolinyl), imidazo[1,2-a]pyridyl, pyrazolo[1,5-a]pyridyl, pyrazolo[1,5-a]pyrimidyl, imidazo[1,2-b]pyridazinyl, [1,2,4]triazolo[4,3-b]pyridazinyl, [1,2,4]triazolo[1,5-a]pyrimidinyl, or [1,2,4]triazolo[1,5-a]pyridyl.

The term "carboxy" or "carboxyl", whether used alone or with other terms, such as "carboxyalkyl", refers to —CO₂H. The term "carbonyl", whether used alone or with other terms, such as "aminocarbonyl", denotes —(C=O)—.

The term "fused bicyclic ring", "fused cyclic", "fused bicyclyl" or "fused cyclyl" as used interchangeably refers to a monovalent or multivalent saturated or partially unsaturated bridged ring system, which refers to a bicyclic ring system that is not aromatic. Such a system may contain isolated or conjugated unsaturation, but not aromatic or heteroaromatic rings in its core structure (but may have aromatic substitution thereon).

The term "spirocyclyl", "spirocyclic", "spiro bicyclyl" or "spiro bicyclic" as used interchangeably refers to a monovalent or multivalent, saturated or partially unsaturated ring system wherein a ring originating from a particular annular carbon of another ring. For example, as depicted below in Structure a, a saturated bridged ring system (ring B and B') is termed as "fused bicyclic", whereas ring A and ring B share an atom between the two saturated ring system, which terms as a "spirocyclyl" or "spiro bicyclyl". Each ring in the fused bicyclyl or the spiro bicyclyl can be either a carbocyclyl or a heterocyclyl, and each ring is optionally substituted independently with one or more substituents described herein.

Structure a

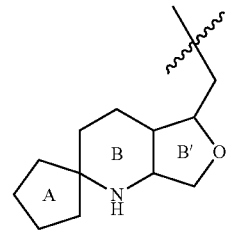

The term "heterocycloalkyl" refers to a monovalent or multivalent saturated ring having 3 to 12 ring atoms as a monocyclic, bicyclic, or tricyclic ring system in which at least one ring atom is selected from nitrogen, sulfur and oxygen.

The term "n membered" where n is an integer typically describes the number of ring-forming atoms in a moiety where the number of ring-forming atoms is n. For example, piperidinyl is an example of a 6 membered heterocycloalkyl and 1,2,3,4-tetrahydro-naphthalene is an example of a 10 membered cycloalkyl group.

The term "unsaturated" refers to a moiety having one or more units of unsaturation.

The term "protecting group" or "PG" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxy-carbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —CH₂CH₂SO₂Ph, cyanoethyl, 2-(trimethylsilyl)ethyl, 2-(trimethylsilyl)ethoxy-methyl-1,2-(p-toluenesulfonyl) ethyl, 2-(p-nitrophenylsulfenyl)-ethyl, 2-(diphenylphosphino)-ethyl, nitroethyl and the like. For a general description of protecting groups and their use, see Greene et al., "Protective Groups in Organic Synthesis," John Wiley &

Sons, New York, 1991 and Kocienski et al., "Protecting Groups," Thieme, Stuttgart, 2005.

The term "prodrug" refers to a compound that is transformed in vivo into a compound of formula (I). Such a transformation can be affected, for example, by hydrolysis in blood or enzymatic transformation of the prodrug form to the parent form in blood or tissue. Prodrugs of the compounds disclosed herein may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound disclosed herein that contains an OH group may be acylated at this position in its prodrug form. Other prodrug forms include phosphates, such as, for example those phosphates resulting from the phosphonation of an OH group on the parent compound. A thorough discussion of prodrugs is provided in Higuchi et al., "Prodrugs as Novel Delivery Systems," Vol. 14, A.C.S. Symposium Series; Roche et al., "Bioreversible Carriers in Drug Design," American Pharmaceutical Association and Pergamon Press, 1987; Rautio et al., "Prodrugs: Design and Clinical Applications," *Nat. Rev. Drug Discovery*, 2008, 7, 255-270, and Hecker et al., "Prodrugs of Phosphates and Phosphonates," *J. Med. Chem.*, 2008, 51, 2328-2345, all of which are incorporated herein by reference.

A "metabolite" refers to a product produced through metabolism in the body of a specified compound or salt thereof. The metabolite of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds disclosed herein, including compounds produced by a process comprising contacting a compound disclosed herein with a mammal for a period of time sufficient to yield a metabolic product thereof.

A "pharmaceutically acceptable salt" refers to organic or inorganic salts of a compound disclosed herein. The pharmaceutically acceptable salts are well known in the art. For example, Berge et al., describe pharmaceutically acceptable salts in detail in *J. Pharm. Sci.*, 1977, 66, 1-19, which is incorporated herein by reference. Some non-limiting examples of the pharmaceutically acceptable salt include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange.

Other examples of the pharmaceutically acceptable salt include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Pharmaceutically acceptable salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further examples of the pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate and aryl sulfonate.

A "solvate" refers to an association or complex of one or more solvent molecules and a compound disclosed herein. Some non-limiting examples of solvents that form solvates include water, isopropanol, ethanol, methanol, DMSO, ethyl acetate, acetic acid, and ethanolamine. The term "hydrate" refers to the complex where the solvent molecule is water.

The term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment, the term "treat", "treating" or "treatment" refers to alleviating or ameliorating at least one physical parameter including those which may not be discernible by the patient. In yet another embodiment, the term "treat", "treating" or "treatment" refers to modulating the disease or disorder, either physically, (e.g., stabilization of a discernible symptom), physiologically, (e.g., stabilization of a physical parameter), or both. In yet another embodiment, the term "treat", "treating" or "treatment" refers to preventing or delaying the onset or development or progression of the disease or disorder.

The term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed, Mack Printing Company, 1990, 1289-1329). Except insofar as any conventional carrier is incompatible with the active ingredient, its use in the therapeutic or pharmaceutical compositions is contemplated.

The term "a therapeutically effective amount" of a compound disclosed herein refers to an amount of the compound disclosed herein that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound disclosed herein that, when administered to a subject, is effective to (1) at least partially alleviate, inhibit, prevent and/or ameliorate a condition, or a disorder or a disease (i) mediated by PI3K or (ii) associated with PI3K activity, or (iii) characterized by activity (normal or abnormal) of PI3K or (2) reduce or inhibit the activity of PI3K or (3) reduce or inhibit the expression of PI3K. In another non-limiting embodiment, the term "a therapeutically effective amount" refers to the amount of the compound disclosed herein that, when administered to a cell, or a tissue, or a non-cellular biological material, or a medium, is effective to at least partially reducing or inhibiting the activity of PI3K; or at least partially reducing or inhibiting the expression of PI3K. The meaning of the term "a therapeutically effective amount" as illustrated in the above embodiment for PI3K also applies by the same means to any other relevant proteins/peptides/enzymes.

The term "cancer" or "cancerous" refers to or describes the physiological condition in mammals that is typically characterized by unregulated cell growth. A "tumor" comprises one or more cancerous cells. Some non-limiting examples of the cancer include carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Description of Compounds of the Invention

The present invention provides heteroaromatic compounds, salts, and pharmaceutical formulations thereof, which are potentially useful in the treatment of diseases, conditions and disorders modulated by protein kinases, especially PI3K and mTOR. More specifically, the present invention provides a compound of Formula (I):

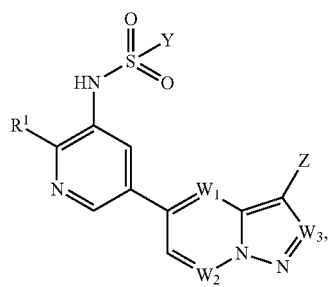

or a stereoisomer, a geometric isomer, a tautomer, an N-oxide, a solvate, a metabolite, a pharmaceutically salt or a prodrug thereof, wherein each of Y, $R^1$, Z, $W_1$, $W_2$ and $W_3$ is as defined herein.

In certain embodiments, each of $W_1$, $W_2$ and $W_3$ is independently N or $CR^c$;

Z is D, CN, $N_3$, or

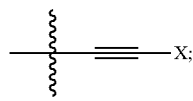

X is H, D, $(C_1-C_6)$alkyl, $(C_3-C_6)$cycloalkyl, $(C_3-C_6)$heterocyclyl, —$(C_1-C_4)$alkylene-$(C_3-C_6)$cycloalkyl, —$(C_1-C_4)$alkylene-$(C_3-C_6)$heterocyclyl, $(C_6-C_{10})$aryl, or 5-10 membered heteroaryl comprising 1, 2, 3 or 4 heteroatoms independently selected from O, S and N, wherein each of the $(C_1-C_6)$alkyl, $(C_3-C_6)$cycloalkyl, $(C_3-C_6)$heterocyclyl, —$(C_1-C_4)$alkylene-$(C_3-C_6)$cycloalkyl, —$(C_1-C_4)$alkylene-$(C_3-C_6)$heterocyclyl, $(C_6-C_{10})$aryl and 5-10 membered heteroaryl is optionally substituted with 1, 2, 3 or 4 substituents independently selected from D, F, Cl, Br, CN, $N_3$, $OR^a$, $SR^a$, $NR^aR^b$, —C(=O)$NR^aR^b$, $(C_1-C_6)$alkyl, $(C_1-C_6)$haloalkyl, $(C_2-C_6)$alkenyl, $(C_2-C_6)$alkynyl, —$(C_1-C_4)$alkylene-CN, —$(C_1-C_4)$alkylene-$OR^a$, —$(C_1-C_4)$alkylene-$NR^aR^b$, $(C_6-C_{10})$aryl, and 5-10 membered heteroaryl;

Y is $(C_1-C_6)$alkyl, $(C_3-C_6)$cycloalkyl, $(C_3-C_6)$heterocyclyl, —$(C_1-C_4)$alkylene-$(C_3-C_6)$cycloalkyl, —$(C_1-C_4)$alkylene-$(C_3-C_6)$heterocyclyl, $(C_2-C_6)$alkenyl, $(C_2-C_6)$alkynyl, $(C_6-C_{10})$aryl, or 5-10 membered heteroaryl comprising 1, 2, 3 or 4 heteroatoms independently selected from O, S and N, wherein each of the $(C_1-C_6)$alkyl, $(C_3-C_6)$cycloalkyl, $(C_3-C_6)$heterocyclyl, —$(C_1-C_4)$alkylene-$(C_3-C_6)$cycloalkyl, —$(C_1-C_4)$alkylene-$(C_3-C_6)$heterocyclyl, $(C_2-C_6)$alkenyl, $(C_2-C_6)$alkynyl, $(C_6-C_{10})$aryl and 5-10 membered heteroaryl is optionally substituted with 1, 2, 3 or 4 substituents independently selected from D, F, Cl, Br, CN, $N_3$, $OR^a$, $SR^a$, $NR^aR^b$, —C(=O)$NR^aR^b$, $(C_1-C_6)$alkyl, $(C_1-C_6)$haloalkyl, $(C_2-C_6)$alkenyl, $(C_2-C_6)$alkynyl, —$(C_1-C_4)$alkylene-CN, —$(C_1-C_4)$alkylene-$OR^a$, —$(C_1-C_4)$alkylene-$NR^aR^b$, $(C_6-C_{10})$aryl, and 5-10 membered heteroaryl;

$R^1$ is H, D, Cl, $OR^a$, $NR^aR^b$, $(C_1-C_6)$aliphatic, or $(C_3-C_6)$cycloalkyl, wherein each of the $(C_1-C_6)$aliphatic and $(C_3-C_6)$cycloalkyl is optionally substituted with 1, 2, 3 or 4 substituents independently selected from D, F, Cl, CN, $N_3$, $OR^a$, $SR^a$, and $NR^aR^b$;

each $R^a$ and $R^b$ is independently H, $(C_1-C_6)$alkyl, $(C_3-C_6)$cycloalkyl, $(C_3-C_6)$heterocyclyl, $(C_6-C_{10})$aryl, 5-10 membered heteroaryl comprising 1, 2, 3 or 4 heteroatoms independently selected from O, S and N, —$(C_1-C_4)$alkylene-$(C_6-C_{10})$aryl, —$(C_1-C_4)$alkylene-(5-10 membered heteroaryl), or $R^a$ and $R^b$ are taken together with the nitrogen atom to which they are attached form a 3-8 membered heterocyclic ring, wherein each of the above substituents is optionally substituted with 1, 2, 3 or 4 substituents independently selected from D, F, Cl, CN, $N_3$, OH, $NH_2$, $(C_1-C_6)$alkoxy, and $(C_1-C_6)$alkylamino; and each $R^c$ is independently H, D, F, Cl, Br, I, $N_3$, CN, OH, $NH_2$, $(C_1-C_6)$alkyl, $(C_1-C_6)$alkoxy, $(C_1-C_6)$alkylamino, $(C_3-C_6)$cycloalkyl, $(C_3-C_6)$heterocyclyl, $(C_6-C_{10})$aryl, or 5-10 membered heteroaryl comprising 1, 2, 3 or 4 heteroatoms independently selected from O, S and N, wherein each of the $(C_1-C_6)$alkyl, $(C_1-C_6)$alkoxy, $(C_1-C_6)$alkylamino, $(C_3-C_6)$cycloalkyl, $(C_3-C_6)$heterocyclyl, $(C_6-C_{10})$aryl and 5-10 membered heteroaryl is optionally substituted with 1, 2, 3 or 4 substituents independently selected from D, F, Cl, CN, $N_3$, OH, $NH_2$, $(C_1-C_6)$alkyl, $(C_3-C_6)$cycloalkyl, $(C_1-C_6)$haloalkyl, $(C_1-C_6)$alkoxy, and $(C_1-C_6)$alkylamino.

In another embodiment, $W_1$ is N or $CR^c$; and each of $W_2$ and $W_3$ is independently $CR^c$.

In another embodiment, Z is CN, $N_3$, or

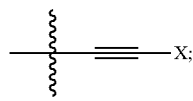

In another embodiment, X is H, D, $(C_1-C_6)$alkyl, $(C_3-C_6)$cycloalkyl, $(C_3-C_6)$heterocyclyl, —$(C_1-C_4)$alkylene-$(C_3-C_6)$cycloalkyl, or —$(C_1-C_4)$alkylene-$(C_3-C_6)$heterocyclyl, wherein each of the $(C_1-C_6)$alkyl, $(C_3-C_6)$cycloalkyl, $(C_3-C_6)$heterocyclyl, —$(C_1-C_4)$alkylene-$(C_3-C_6)$cycloalkyl and —$(C_1-C_4)$alkylene-$(C_3-C_6)$heterocyclyl is optionally substituted with 1, 2, 3 or 4 substituents independently selected from D, F, Cl, Br, CN, $N_3$, $OR^a$, $SR^a$, $NR^aR^b$, —C(=O)$NR^aR^b$, $(C_1-C_3)$alkyl, $(C_1-C_3)$haloalkyl, $(C_2-C_4)$alkenyl, and $(C_2-C_4)$alkynyl.

In another embodiment, Y is (C₁-C₆)alkyl, (C₃-C₆)cycloalkyl, (C₂-C₆)alkenyl, (C₂-C₆)alkynyl, (C₆-C₁₀)aryl, or 5-10 membered heteroaryl comprising 1, 2, 3 or 4 heteroatoms independently selected from O, S and N, wherein each of the (C₁-C₆)alkyl, (C₃-C₆)cycloalkyl, (C₂-C₆)alkenyl, (C₂-C₆)alkynyl, (C₆-C₁₀)aryl and 5-10 membered heteroaryl is optionally substituted with 1, 2, 3 or 4 substituents independently selected from D, F, Cl, Br, CN, N₃, OR$^a$, SR$^a$, NR$^a$R$^b$, —C(=O)NR$^a$R$^b$, (C₁-C₃)alkyl, (C₁-C₃)haloalkyl, (C₂-C₄)alkynyl, (C₆-C₁₀)aryl, and 5-10 membered heteroaryl.

In another embodiment, R$^1$ is H, D, Cl, CH₃, CH₂CH₃, CF₃, CH₂CF₃, OCH₃, or OCH₂CH₃.

In another embodiment, each R$^c$ is independently H, D, F, Cl, N₃, CN, NH₂, (C₁-C₃)alkyl, (C₁-C₃)alkoxy, (C₁-C₃)alkylamino, (C₃-C₆)cycloalkyl, or (C₃-C₆)heterocyclyl, wherein each of the (C₁-C₃)alkyl, (C₁-C₃)alkoxy, (C₁-C₃)alkylamino, (C₃-C₆)cycloalkyl and (C₃-C₆)heterocyclyl is optionally substituted with 1, 2, 3 or 4 substituents independently selected from D, F, CN, N₃, OH, NH₂, (C₁-C₃)alkyl, (C₃-C₆)cycloalkyl, and (C₁-C₃)haloalkyl.

Some non-limiting examples of the compounds disclosed herein, and their pharmaceutically acceptable salts and solvates thereof, are shown in the following:

TABLE 1

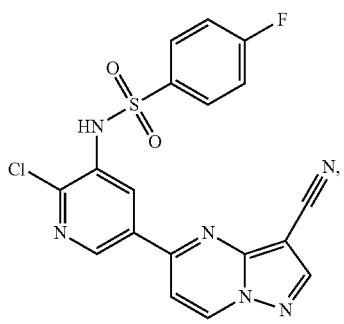 [SMILES: N#Cc1cnn2ccc(-c3cnc(Cl)c(NS(=O)(=O)c4ccc(F)cc4)c3)nc12]

(1)

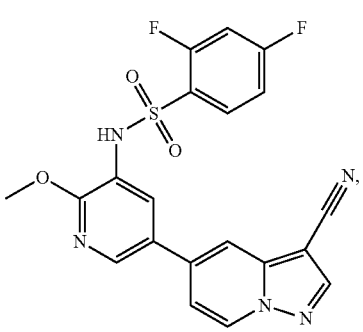 [SMILES: COc1ncc(-c2ccn3ncc(C#N)c3c2)cc1NS(=O)(=O)c1ccc(F)cc1F]

(2)

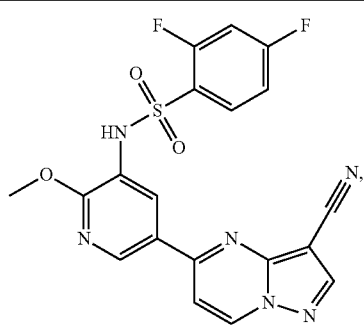

(3)

TABLE 1-continued

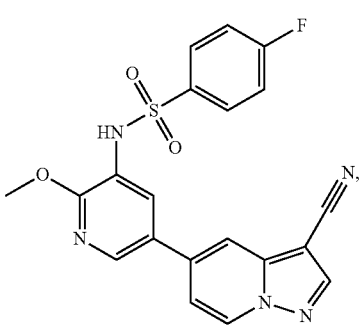 [SMILES: COc1ncc(-c2ccn3ncc(C#N)c3c2)cc1NS(=O)(=O)c1ccc(F)cc1]

(4)

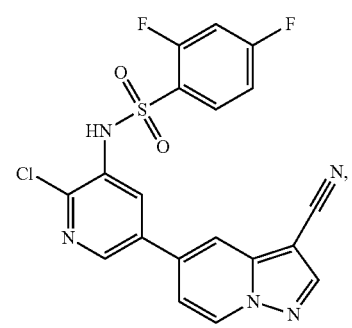 [SMILES: N#Cc1cnn2ccc(-c3cnc(Cl)c(NS(=O)(=O)c4ccc(F)cc4F)c3)cc12]

(5)

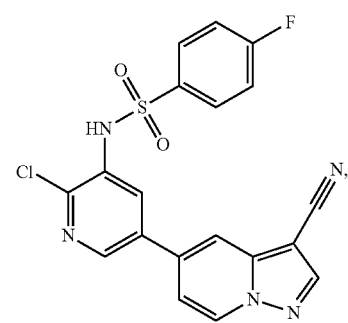 [SMILES: N#Cc1cnn2ccc(-c3cnc(Cl)c(NS(=O)(=O)c4ccc(F)cc4)c3)cc12]

(6)

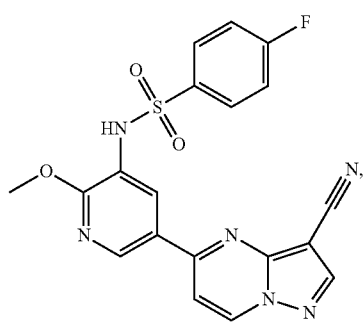

(7)

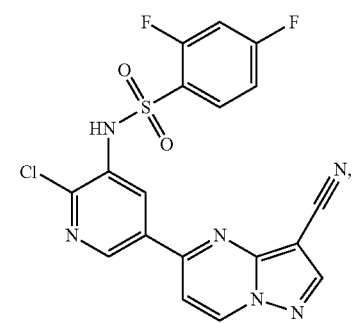

(8)

TABLE 1-continued
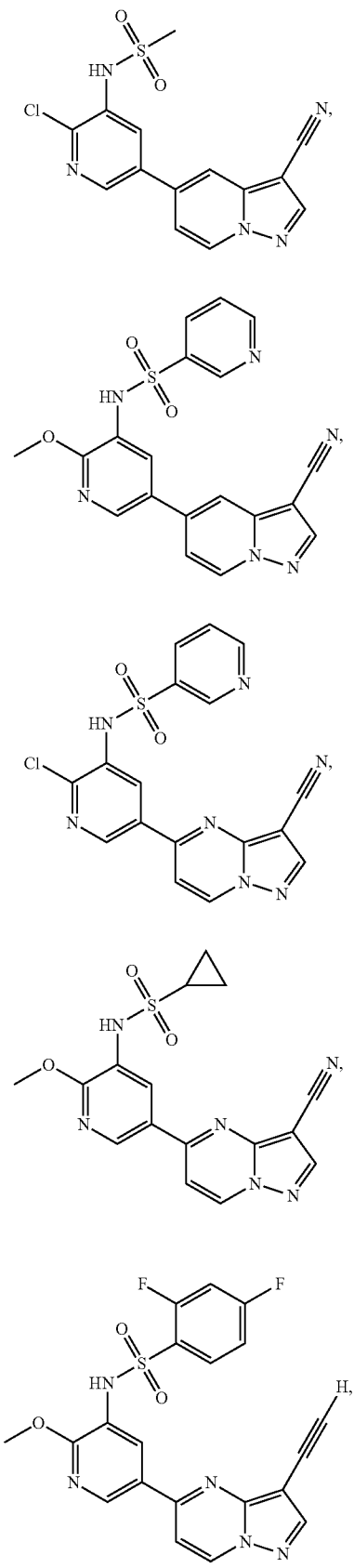
TABLE 1-continued
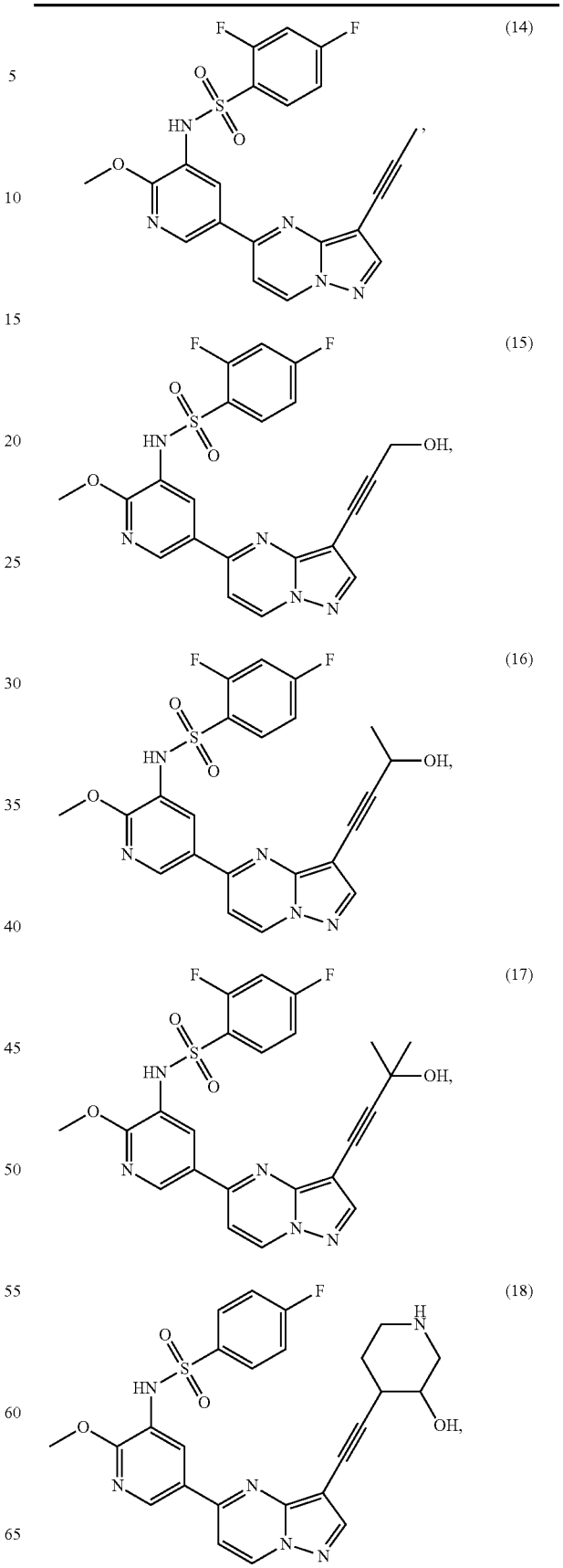

TABLE 1-continued
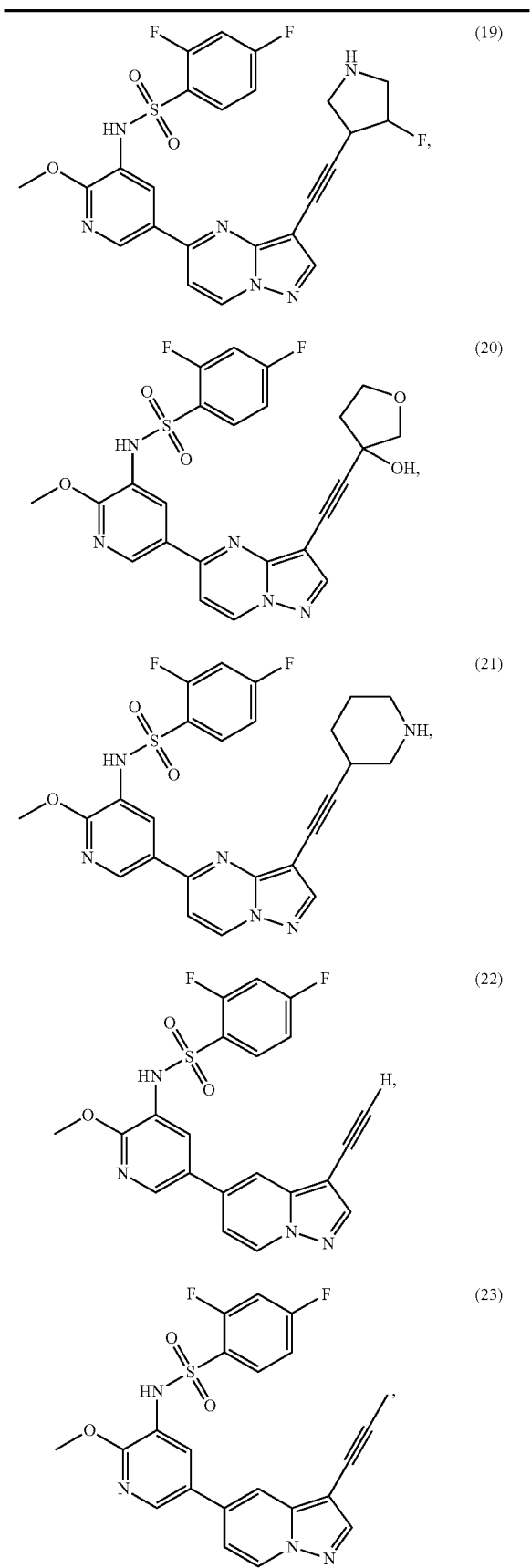
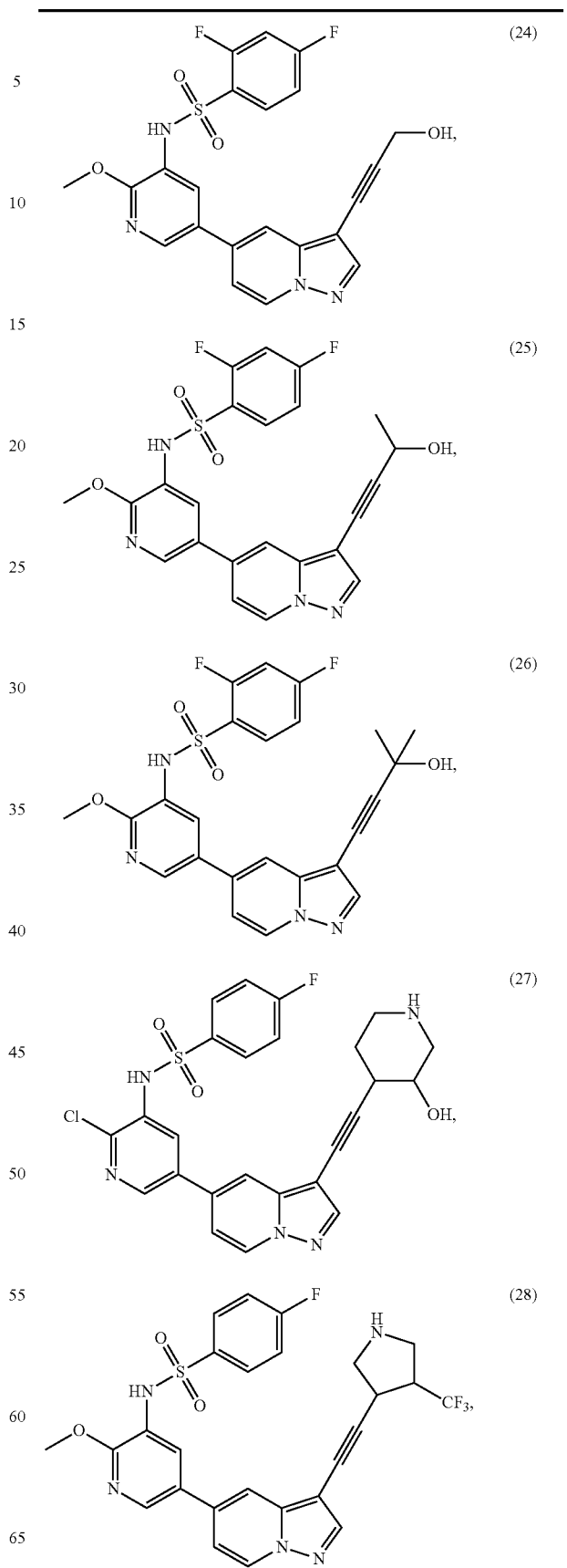

TABLE 1-continued

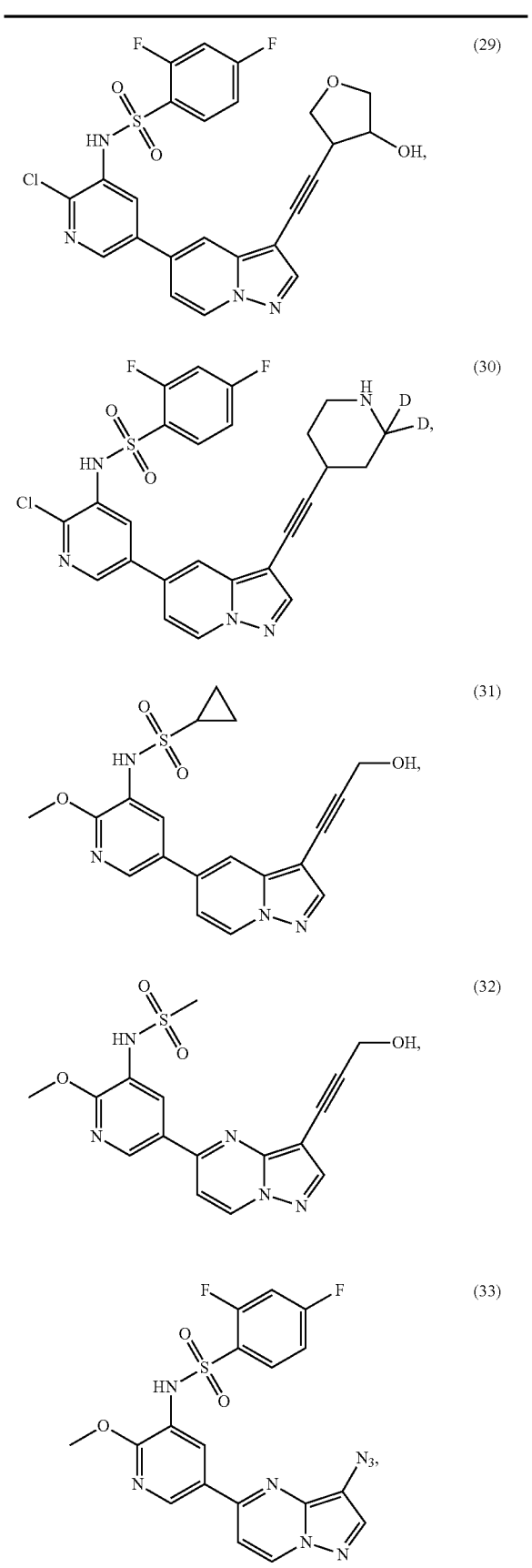

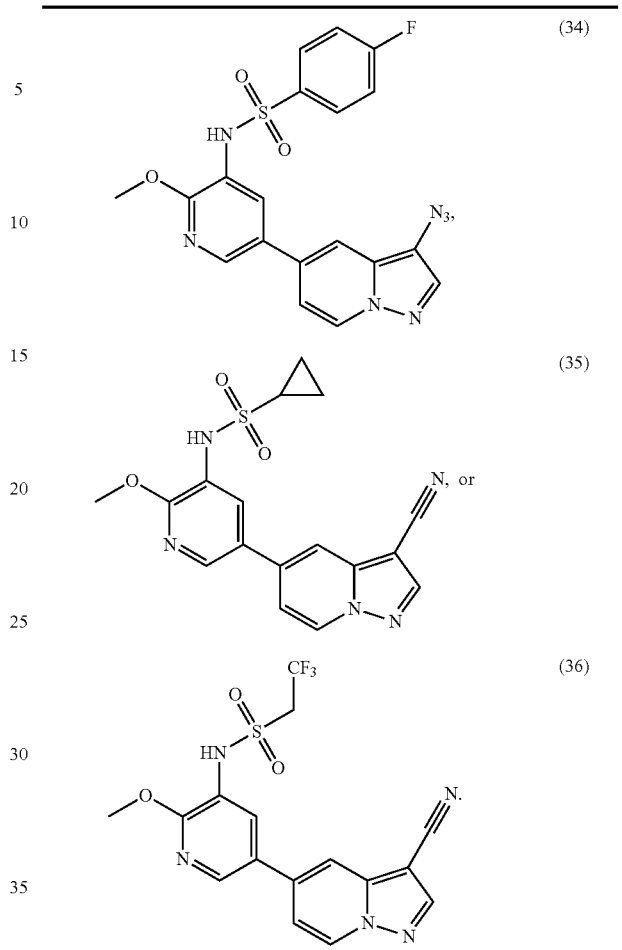

The present invention also comprises the use of a compound disclosed herein, or pharmaceutically acceptable salt thereof, in the manufacture of a medicament for the treatment either acutely or chronically of a hyperproliferative disease state and/or an angiogenesis mediated disease state, including those described previously. The compounds disclosed herein are useful in the manufacture of an anti-cancer medicament. The compounds disclosed herein are also useful in the manufacture of a medicament to attenuate or prevent disorders through inhibition of protein kinases. The present invention comprises a pharmaceutical composition comprising a therapeutically effective amount of a compound of Formula (I) in association with at least one pharmaceutically acceptable carrier, adjuvant or diluent.

The present invention also comprises a method of treating hyperproliferating and angiogenesis related disorders in a subject having or susceptible to such disorder, the method comprising treating the subject with a therapeutically effective amount of a compound of Formula (I).

Unless otherwise stated, all stereoisomers, geometric isomers, tautomers, solvates, metabolites, salts, and pharmaceutically acceptable prodrugs of the compounds disclosed herein are within the scope of the invention.

In certain embodiments, the salt is a pharmaceutically acceptable salt. The phrase "pharmaceutically acceptable" indicates that the substance or composition must be compatible chemically and/or toxicologically, with the other ingredients comprising a formulation, and/or the mammal being treated therewith.

The compounds disclosed herein also include salts of such compounds which are not necessarily pharmaceutically acceptable salts, and which may be useful as intermediates for preparing and/or purifying compounds of Formula I and/or for separating enantiomers of compounds of Formula (I).

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, subsalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethan sulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts disclosed herein can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences," 20th ed., Mack Publishing Company, Easton, Pa., 1985; and in "Handbook of Pharmaceutical Salts: Properties, Selection, and Use" by Stahl and Wermuth, Wiley-VCH, Weinheim, Germany, 2002.

Furthermore, the compounds disclosed herein, including their salts, can also be obtained in the form of their hydrates, or include other solvents used for their crystallization. The compounds disclosed herein may inherently or by design form solvates with pharmaceutically acceptable solvents (including water); therefore, it is intended that the invention embrace both solvated and unsolvated forms.

In another aspect, provided herein are methods of preparing, methods of separating, and methods of purifying compounds of Formula (I). The compounds disclosed herein may have in general several asymmetric centers and are typically depicted in the form of racemic mixtures. This invention is intended to encompass racemic mixtures, partially racemic mixtures and separate enantiomers and diasteromers.

Compounds disclosed herein can be in the form of one of the possible isomers, rotamers, atropisomers, tautomers or mixtures thereof. This invention is intended to encompass mixtures of isomers, rotamers, atropisomers, tautomers, partially mixed isomers, rotamers, atropisomers, or tautomers, and separated isomers, rotamers, atropisomers, tautomers.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds disclosed herein include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F, $^{31}$P, $^{32}$P, $^{36}$S, $^{37}$Cl, and $^{125}$I respectively.

In another aspect, the compounds disclosed herein include isotopically labeled compounds as defined herein, for example those into which radioactive isotopes, such as $^3$H, $^{14}$C and $^{18}$F, or those into which nonradioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g. $D_2O$, acetone-$d_6$, and DMSO-$d_6$.

Composition, Formulations and Administration of the Compounds Disclosed Herein

According to one aspect, the invention features pharmaceutical compositions that include a compound of formula (I), a compound listed in Table 1, and a pharmaceutically acceptable carrier, adjuvant, or vehicle. The amount of compound in the compositions disclosed herein is such that is effective to detectably inhibit a protein kinase in a biological sample or in a patient.

It will also be appreciated that certain of the compounds disclosed herein can exist in free form for treatment, or where appropriate, as a pharmaceutically acceptable derivative thereof. According to the present invention, some non-limiting examples of the pharmaceutically acceptable derivatives include pharmaceutically acceptable prodrugs, salts, esters, salts of such esters, or any other adducts or derivatives which upon administration to a patient in need is capable of providing, directly or indirectly, a compound as otherwise described herein, or a metabolite or residue thereof.

As described above, the pharmaceutically acceptable compositions disclosed herein additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Troy et al., "Remington: The Science and Practice of Pharmacy," 21st ed., 2005, Lippincott Williams & Wilkins, Philadelphia and Swarbrick et al., "Encyclopedia of Pharmaceutical Technology," eds., 1988-1999, Marcel Dekker, New York, all of which are incorporated by reference in their entireties, are disclosed various carriers used in formulating pharmaceutically acceptable compositions and known techniques for the preparation thereof. Except insofar as any conventional carrier medium is incompatible with the compounds disclosed herein, such as by producing any undesirable biological effect or otherwise interacting in a deleterious manner with any other component(s) of the pharmaceutically acceptable composition, its use is contemplated to be within the scope of this invention.

Some non-limiting examples of materials which can serve as pharmaceutically acceptable carriers include ion exchangers, alumina, aluminum stearate, lecithin, serum proteins, such as human serum albumin, buffer substances such as phosphates, glycine, sorbic acid or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions disclosed herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the low intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used. For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of a compound disclosed herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, dissolving or suspending the compound in an oil vehicle accomplishes delayed absorption of a parenterally administered compound form.

Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polythylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain pacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds disclosed herein are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions disclosed herein will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds disclosed herein that may be combined with the carrier materials to produce a composition in a single dosage form will vary depending upon the host treated, the particular mode of administration. Preferably, the compositions should be formulated so that a dosage of between 0.01-200 mg/kg body weight/day of the inhibitor can be administered to a patient receiving these compositions.

Compounds of this invention can be administered as the sole pharmaceutical agent or in combination with one or more other additional therapeutic (pharmaceutical) agents where the combination causes no unacceptable adverse effects. This may be of particular relevance for the treatment of hyper-proliferative diseases such as cancer. In this instance, the compound of this invention can be combined with known cytotoxic agents, signal transduction inhibitors, or with other anti-cancer agents, as well as with admixtures and combinations thereof. As used herein, additional therapeutic agents that are normally administered to treat a particular disease, or condition, are known as "appropriate for the disease, or condition, being treated". As used herein, "additional therapeutic agents" is meant to include chemotherapeutic agents and other anti-proliferative agents.

For example, chemotherapeutic agents or other antiproliferative agents may be combined with the compounds of this invention to treat proliferative disease or cancer. Examples of chemotherapeutic agents or other antiproliferative agents include HDAC inhibitors including, but are not limited to, SAHA, MS-275, MGO 103, and those described in WO 2006/010264, WO 03/024448, WO 2004/069823, US 2006/0058298, US 2005/0288282, WO 00/71703, WO 01/38322, WO 01/70675, WO 03/006652, WO 2004/035525, WO 2005/030705, WO 2005/092899, and demethylating agents including, but not limited to, 5-aza-dC, Vidaza and Decitabine and those described in U.S. Pat. No. 6,268,137, U.S. Pat. No. 5,578,716, U.S. Pat. No. 5,919,772, U.S. Pat. No. 6,054,439, U.S. Pat. No. 6,184,211, U.S. Pat. No. 6,020,318, U.S. Pat. No. 6,066,625, U.S. Pat. No. 6,506,735, U.S. Pat. No. 6,221,849, U.S. Pat. No. 6,953,783, U.S. Ser. No. 11/393,380.

In another embodiment of the present invention, for example, chemotherapeutic agents or other anti-proliferative agents may be combined with the compounds of this invention to treat proliferative diseases and cancer. Examples of known chemotherapeutic agents include, but are not limited to, for example, other therapies or anticancer agents that may be used in combination with the inventive anticancer agents disclosed herein and include surgery, radiotherapy (in but a few examples, gamma radiation, neutron beam radiotherapy, electron beam radiotherapy, proton therapy, brachytherapy, and systemic radioactive isotopes, to name a few), endocrine therapy, taxanes (paclitaxel, taxotere), platinum derivatives (cisplatin, carboplatin, oxaliplatin), biologic response modifiers (interferons, interleukins), tumor necrosis factor (TNF, TRAIL receptor targeting agents, to name a few), hyperthermia and cryotherapy, agents to attenuate any adverse effects (e.g., antiemetics), and other approved chemotherapeutic drugs, including, but not limited to, alkylating drugs (chlormethine, chlorambucil, cyclophosphamide, ifosfamide, melphalan, etc.), anti-metabolites (methotrexate, raltitrexed, pemetrexed, etc.), purine antagonists and pyrimidine antagonists (6-mercaptopurine, 5-fluorouracil, cytarabine, gemcitabine), spindle poisons (vinblastine, vincristine, vinorelbine), podophyllotoxins (etoposide, irinotecan, topotecan), antibiotics (doxorubicin, bleomycin, mitomycin), nitrosoureas (carmustine, lomustine), cell cycle inhibitors (KSP mitotic kinesin inhibitors, CENP-E and CDK inhibitors), enzymes (asparaginase), hormones (tamoxifen, leuprolide, flutamide, megestrol, dexamethasone), antiangiogenic agents (avastin and others), monoclonal antibodies (Belimumab (BENLYSTA®), brentuximab (ADCETRIS®), cetuximab (ERBITUX®), gemtuzumab (MYLOTARG®), ipilimumab (YERVOY®), ofatumumab (ARZERRA®), panitumumab (VECTIBIX®), ranibizumab (LUCENTIS®), rituximab (RITUXAN®), tositumomab (BEXXAR®), trastuzumab (HERCEPTIN®), kinase inhibitors (imatinib) (GLEEVEC®), sunitinib (SUTENT®), sorafenib (NEXAVAR®), erlotinib (TARCEVA®), gefitinib (IRESSA®), dasatinib (SPRYCEL®), nilotinib (TASIGNA®), lapatinib (TYKERB®), crizotinib (XALKORI®), ruxolitinib (JAKAFI®), vemurafenib (ZELBORAF®), vandetanib (CAPRELSA®), pazopanib (VOTRIENT®), and others), and agents inhibiting or activating cancer pathways such as the mTOR, HIF (hypoxia induced factor) pathways (such as everolimus and temsirolimus) and others. For a more comprehensive discussion of updated cancer therapies see, http://www.nci.nih.gov/, a list of the FDA approved oncology drugs at http://www.fda.gov/cder/cancer/druglistrame.htm, and The Merck Manual, Eighteenth Ed. 2006, the entire contents of which are hereby incorporated by reference.

In another embodiment, the compounds disclosed herein can be combined, with cytotoxic anti-cancer agents. Examples of such agents can be found in the 13th Edition of the Merck Index (2001). These agents include, by no way of limitation, asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other cytotoxic drugs suitable for use with the compounds disclosed herein include, but are not limited to, those compounds acknowledged to be used in the treatment of neoplastic diseases, such as those for example in Goodman and Gilman's The Pharmacological Basis of Therapeutics (Ninth Edition, 1996, McGraw-Hill). These agents include, by no way of limitation, aminoglutethimide, L-asparaginase, azathioprine, 5-azacytidine cladribine, busulfan, diethylstilbestrol, 2,2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other cytotoxic anti-cancer agents suitable for use in combination with the compounds disclosed herein also include newly discovered cytotoxic principles such as oxaliplatin, gemcitabine, capecitabine, epothilone and its natural or synthetic derivatives, temozolomide (Quinn et al., *J. Clin. Oncol.*, 2003, 21(4), 646-651), tositumomab (BEXXAR®), trabedectin (Vidal et al., Proceedings of the American Society for Clinical Oncology, 2004, 23, abstract 3181), and the inhibitors of the kinesin spindle protein Eg5 (Wood, et al., *Curr. Opin. Pharmacol.*, 2001, 1, 370-377).

In another embodiment, the compounds disclosed herein can be combined with other signal transduction inhibitors. Some non-limiting examples of such agents include antibody therapies such as trastuzumab (HERCEPTIN®), cetuximab (ERBITUX®), ipilimumab (YERVOY®) and pertuzumab. Some non-limiting examples of such therapies also include small-molecule kinase inhibitors such as imatinib (GLEEVEC®), sunitinib (SUTENT®), sorafenib (NEXAVAR®), erlotinib (TARCEVA®), gefitinib (IRESSA®), dasatinib (SPRYCEL®), nilotinib (TASIGNA®), lapatinib (TYKERB®), crizotinib (XALKORI®), ruxolitinib (JAKAFI®), vemurafenib (ZELBORAF®), vandetanib (CAPRELSA®), pazopanib (VOTRIENT®), afatinib, alisertib, amuvatinib, axitinib, bosutinib, brivanib, canertinib, cabozantinib, cediranib, crenolanib, dabrafenib, dacomitinib, danusertib, dovitinib, foretinib, ganetespib, ibrutinib, iniparib, lenvatinib, linifanib, linsitinib, masitinib, momelotinib, motesanib, neratinib, niraparib, oprozomib, olaparib, pictilisib, ponatinib, quizartinib, regorafenib, rigosertib, rucaparib, saracatinib, saridegib, tandutinib, tasocitinib, telatinib, tivantinib, tivozanib, tofacitinib, trametinib, vatalanib, veliparib, vismodegib, volasertib, BMS-540215, BMS777607, JNJ38877605, TKI258, GDC-0941 (Folkes, et al., *J. Med. Chem.*, 2008, 51, 5522), BZE235, and others.

In another embodiment, the compounds disclosed herein can be combined with inhibitors of histone deacetylase. Some non-limiting examples of such agents include suberoylanilide hydroxamic acid (SAHA), LAQ-824 (Ottmann et al., Proceedings of the American Society for Clinical Oncology, 2004, 23, abstract 3024), LBH-589 (Beck et al., Proceedings of the American Society for Clinical Oncology, 2004, 23, abstract 3025), MS-275 (Ryan et al., Proceedings of the American Association of Cancer Research, 2004, 45, abstract 2452), FR-901228 (Piekarz et al., Proceedings of the American Society for Clinical Oncology, 2004, 23, abstract 3028) and MGCDO1 03 (U.S. Pat. No. 6,897,220).

In another embodiment, the compounds disclosed herein can be combined with other anti-cancer agents such as proteasome inhibitors, and mTOR inhibitors. These include, by no way of limitation, bortezomib, and CCI-779 (Wu et al., Proceedings of the American Association of Cancer Research, 2004, 45, abstract 3849). The compounds disclosed herein can be combined with other anti-cancer agents such as topoisomerase inhibitors, including but not limited to camptothecin.

Those additional agents may be administered separately from the compound-containing composition, as part of a multiple dosage regimen. Alternatively, those agents may be part of a single dosage form, mixed together with the compound of this invention in a single composition. If administered as part of a multiple dosage regimen, the two active agents may be submitted simultaneously, sequentially or within a period of time from one another which would result in the desired activity of the agents.

The amount of both the compound and the additional therapeutic agent (in those compositions which comprise an additional therapeutic agent as described above) that may be combined with the carrier materials to produce a single dosage form will vary depending upon the host treated and the particular mode of administration. Normally, the amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent. In those compositions which comprise an additional therapeutic agent, that additional therapeutic agent and the compound of this invention may act synergistically.

Uses of the Compounds and Compositions Disclosed Herein

The invention features pharmaceutical compositions that include a compound of formula (I), a compound listed in Table 1, and a pharmaceutically acceptable carrier, adjuvant, or vehicle. The amount of compound in the compositions of the invention is such that is effective to detectably inhibit or modulate a protein kinase, such as PI3K or mTOR activity. The compounds disclosed herein are useful in therapy as antineoplastic agents or to minimize deleterious effects of PI3K or mTOR signaling.

Compounds disclosed herein would be useful for, but not limited to, the prevention or treatment of proliferative diseases, condition, or disorder in a patient by administering to the patient a compound or a composition disclosed herein in an effective amount. Such diseases, conditions, or disorders include cancer, particularly metastatic cancer, atherosclerosis and lung fibrosis.

The compounds disclosed herein would be useful for the treatment of neoplasm including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xeroderma pigmentosum, keratoacanthoma, thyroid follicular cancer and Kaposi's sarcoma).

The compounds also would be useful for treatment of ophthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemanginoma, angiofibroma of the nasopharynx and avascular necrosis of bone; and disorders of the female reproductive system such as endometriosis. The compounds are also useful for the treatment of edema, and conditions of vascular hyperpermeability.

The compounds disclosed herein are also useful in the treatment of diabetic conditions such as diabetic retinopathy and microangiopathy. The compounds disclosed herein are also useful in the reduction of blood flow in a tumor in a subject. The compounds disclosed herein are also useful in the reduction of metastasis of a tumor in a subject.

Besides being useful for human treatment, these compounds are also useful for veterinary treatment of companion animals, exotic animals and farm animals, including mammals, rodents, and the like. More preferred animals include horses, dogs, and cats. As used herein, the compounds disclosed herein include the pharmaceutically acceptable derivatives thereof.

Where the plural form is used for compounds, salts, and the like, this is taken to mean also a single compound, salt and the like.

The treatment method that includes administering a compound or composition disclosed herein can further include administering to the patient an additional therapeutic agent (combination therapy) selected from: a chemotherapeutic or anti-proliferative agent, or an anti-inflammatory agent, wherein the additional therapeutic agent is appropriate for the disease being treated and the additional therapeutic agent is administered together with a compound or composition disclosed herein as a single dosage form or separately from the compound or composition as part of a multiple dosage form. The additional therapeutic agent may be administered at the same time as a compound disclosed herein or at a different time. In the latter case, administration may be staggered by, for example, 6 hours, 12 hours, 1 day, 2 days, 3 days, 1 week, 2 weeks, 3 weeks, 1 month, or 2 months.

The invention also features a method of inhibiting the growth of a cell that expresses PI3K or mTOR, that includes contacting the cell with a compound or composition disclosed herein, thereby causing inhibition of growth of the cell. Examples of a cell whose growth can be inhibited include: a breast cancer cell, a colorectal cancer cell, a lung cancer cell, a papillary carcinoma cell, a prostate cancer cell, a lymphoma cell, a colon cancer cell, a pancreatic cancer cell, an ovarian cancer cell, a cervical cancer cell, a central nervous system cancer cell, an osteogenic sarcoma cell, a renal carcinoma cell, a hepatocellular carcinoma cell, a bladder cancer cell, a gastric carcinoma cell, a head and neck squamous carcinoma cell, a melanoma cell, or a leukemia cell.

The invention provides a method of inhibiting or modulating the activity of PI3K or mTOR in a biological sample comprising contacting the biological sample with a compound or composition disclosed herein. The term "biological sample" as used herein, means a sample outside a living organism and includes, without limitation, cell cultures or extracts thereof; biopsied material obtained from a mammal or extracts thereof; and blood, saliva, urine, feces, semen, tears, or other body fluids or extracts thereof. Inhibition or modulation of kinase activity, particularly PI3K or mTOR activity, in a biological sample is useful for a variety of purposes known to one of skill in the art. Examples of such purposes include, but are not limited to, blood transfusion, organ-transplantation, biological specimen storage, and biological assays.

In certain embodiments of the present invention an "effective amount" or "effective dose" of the compound or pharmaceutically acceptable composition is that amount effective for treating or lessening the severity of one or more of the aforementioned disorders. The compounds and compositions, according to the method disclosed herein, may be administered using any amount and any route of administration effective for treating or lessening the severity of the disorder or disease. The exact amount required will vary from subject to subject, depending on the species, age, and general condition of the subject, the severity of the infection, the particular agent, its mode of administration, and the like. A compound or composition can also be administered with one or more other therapeutic agents, as discussed above.

The compounds of this invention or pharmaceutical compositions thereof may also be used for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a compound of this invention.

Suitable coatings and the general preparation of coated implantable devices are described in U.S. Pat. Nos. 6,099,562; 5,886,026; and 5,304,121, the contents of each of which are incorporated by reference herein. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics into the composition. Implantable devices coated with a compound of this invention are another embodiment of the present invention. The compounds may also be coated on implantable medical devices, such as beads, or co-formulated with a polymer or other molecule, to provide a "drug depot" thus permitting the drug to be released over a longer time period than administration of an aqueous solution of the drug.

General Synthetic Procedures

In order to illustrate the invention, the following examples are included. However, it is to be understood that these examples do not limit the invention and are only meant to suggest a method of practicing the invention.

Generally, the compounds in this invention may be prepared by methods described herein, wherein the substituents are as defined for formula (I), above, except where further noted. The following non-limiting schemes and examples are presented to further exemplify the invention. Persons skilled in the art will recognize that the chemical reactions described herein may be readily adapted to prepare a number of other compounds disclosed herein, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, Shanghai Medpep. Co Ltd, Aladdin-Shanghai Jinchun Reagents, Ltd, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tainjin YuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexanes, DMA and DMF were treated with anhydrous $Na_2SO_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory. $^1$H NMR spectra were recorded with a Bruker 400 MHz spectrometeror a Bruker 600 MHz spectrometer at ambient temperature. $^1$H NMR spectra were obtained as $CDCl_3$, DMSO-$d_6$, $CD_3OD$ or acetone-$d_6$ solutions (reported in ppm), using TMS (0 ppm) or chloroform (7.26 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Low-resolution mass spectral (MS) data were generally determined on an Agilent 6120 Quadrupole HPLC-MS (Zorbax SB-C18, 2.1×30 mm, 3.5 micron, 6 minutes run, 0.6 mL/min flow rate, 5% to 95% (0.1% formic acid in $CH_3CN$) in (0.1% formic acid in $H_2O$)) with UV detection at 210 nm/254 nm and electrospray ionization mode (ESI).

Purities of compounds were assessed by Agilent 1260 Pre-HPLC or Calesep Pump 250 Pre-HPLC (Column NOVASEP 50/80 mm DAC) with UV detection at 210 nm/254 nm.

The following abbreviations are used throughout the specification:
$Ac_2O$ acetic anhydride
$BBr_3$ boron tribromide
BINAP 2,2'-bis(diphenylphosphino)-1,1'-binaphthyl
BOC, Boc butyloxycarbonyl
BSA bovine serum albumin
$CDCl_3$ chloroform deuterated
$CHCl_3$ chloroform
$CH_2Cl_2$, DCM methylene chloride
$CH_3CN$ methyl cyanide
$CH_3SO_2Cl$, MsCl methanesulfonyl chloride
$Cs_2CO_3$ cesium carbonate
Cu copper
CuI cuprous iodide
DAST Diethylaminosulfur trifluoride
DBU 1,8-Diazabicyclo[5.4.0]undec-7-ene
DEAD dimethyl azodicarboxylate
DIAD diisopropyl azodicarboxylate
DIBAL diisobutylaluminum hydride
DIEA, DIPEA diisopropylethylamine
DMAP 4-dimethylaminopyridine
DME dimethoxyethane
DMF dimethylformamide
DMSO dimethylsulfoxide
DMSO-$d_6$ dimethylsulfoxide deuterated
DPPA diphenylphosphoryl azide
EDCI 1-(3-dimethylaminopropyl)-3-ethylcarbodiimide hydrochloride
EtOAc, EA ethyl acetate
EtOH ethanol
$Et_2O$ diethyl ether
$Et_3N$, TEA triethylamine
FBS fetal bovine serum
Fe iron
g gram
h hour
HATU O-(7-azabenzotriazol-1-yl)-N,N,N',N'-tetramethyluronium hexafluorophosphate
HBr hydrobromic acid HBTU O-benzotriazol-1-yl-N,N,N',N'-tetramethyluronium hexafluorophosphate
HCl hydrochloric acid
$H_2$ hydrogen
$H_2O$ water
$H_2O_2$ hydrogen peroxide
HOAc, AcOH acetic acid
HOBt 1-hydroxybenzotriazole hydrate
i-$Pr_2$NH diisopropylamine
$K_2CO_3$ potassium carbonate
KOH potassium hydroxide
LiHMDS lithium bis(trimethylsilyl)amide
LDA Lithium diisopropylamide
MCPBA meta-chloroperbenzoic acid
MeCN, $CH_3CN$ acetonitrile
MeI methyl iodide
MeOH, $CH_3OH$ methanol
2-MeTHF 2-methyl tetrahydrofuran
$MgSO_4$ magnesium sulfate
MsCl methanesulfonyl chloride
mL, ml milliliter
min minute
$N_2$ nitrogen
$NaBH_4$ sodium borohydride
$NaBH_3CN$ sodium cyanoborohydride
NaCl sodium chloride
$NaClO_2$ sodium chlorite
NaH sodium hydride
$Na_2CO_3$ sodium carbonate
$NaHCO_3$ sodium bicarbonate
$NaH_2PO_4$ sodium biphosphate
NaI sodium iodide
NaO(t-Bu) sodium tert-butoxide
NaOH sodium hydroxide
$Na_2SO_4$ sodium sulfate
NBS N-Bromosuccinimide
NIS N-Iodosuccinimide
$NH_3$ ammonia
$NH_4Cl$ ammonium chloride
NMP N-methylpyrrolidinone
PBS phosphate buffered saline
$P(t-Bu)_3$ tri(tert-butyl)phosphine
Pd/C palladium on carbon
$Pd_2(dba)_3$ bis(dibenzylideneacetone) palladium
$Pd(dppf)Cl_2$ 1,1-bis(diphenylphosphino)ferrocene palladium dichloride
$Pd(dppf)Cl_2 \cdot CH_2Cl_2$ dichloro[1,1'bis(diphenylphosphino)ferrocene]palladium(II) dichloromethane adduct
$Pd(OAc)_2$ palladium acetate
$Pd(OH)_2$ palladium hydroxide
$Pd(PPh_3)_4$ palladium tetrakis triphenylphosphine
$Pd(PPh_3)_2Cl_2$ Bis(triphenylphosphine)palladium(II) chloride
PE petroleum ether (60-90° C.)
$POCl_3$ phosphorous oxychloride
$PCl_5$ Phosphorus (V) chloride
PyBop benzotriazol-1-yl-oxytripyrrolidinophosphonium hexafluorophosphate
RT, rt, r.t. room temperature
Rt retention time
TBAB tetrabutylammonium bromide
TBAF tetrabutyl ammonium fluoride
TBAHSO$_4$ tetrabutylammonium hydrogen sulfate
TBTU O-benzotriazol-1-yl-N,N,N',N'-tetramethyluronium tetrafluoroborate
TFA trifluoroacetic acid
TEAC bis(tetra-ethylammonium)carbonate THF tetrahydrofuran
μL microliter
X-Phos 5-Bromo-4-chloro-3-indolylphosphat p-Toluidine salt Representative synthetic procedures for the preparation of compounds disclosed herein are outlined below in following schemes. Unless otherwise indicated, $R^1$, $W_1$, $W_2$, $W_3$, Y and Z carry the definitions set forth above in connection with formula (I). X' is Cl, Br, or I.

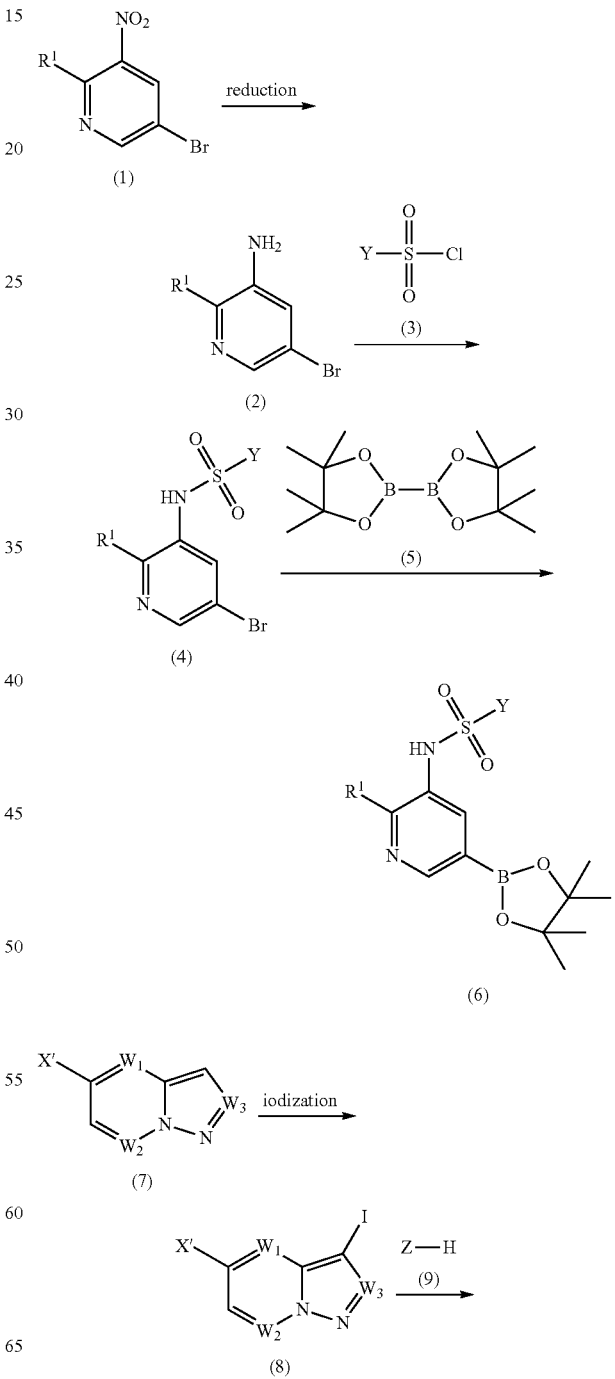

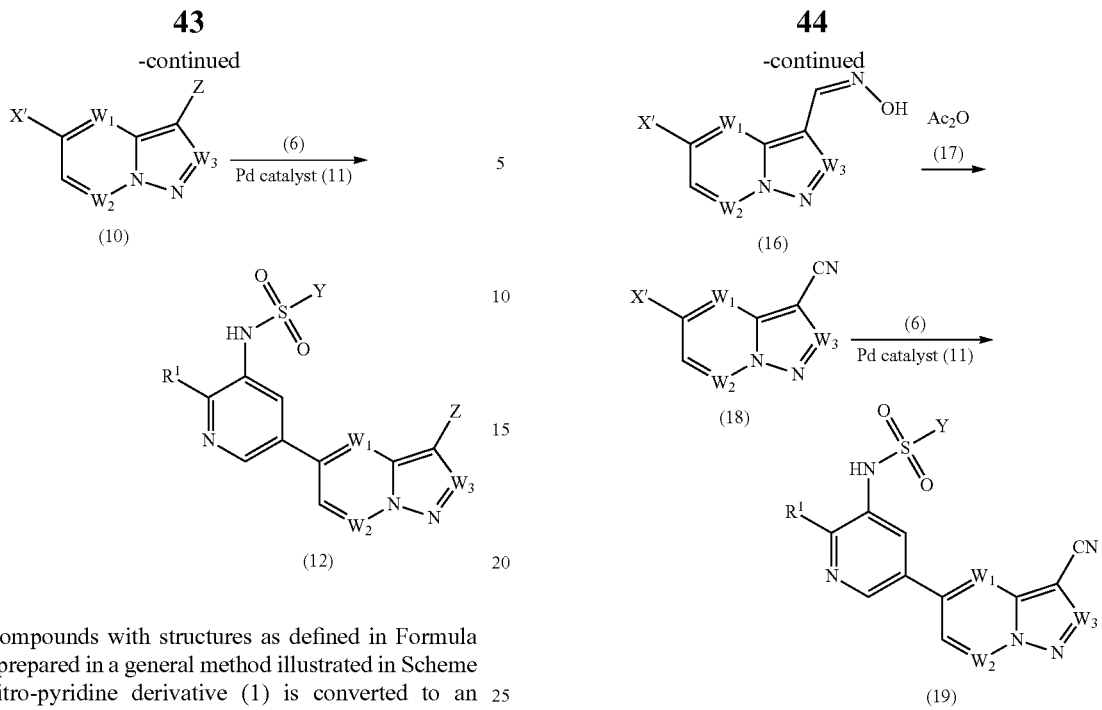

Some compounds with structures as defined in Formula (I) can be prepared in a general method illustrated in Scheme 1. The nitro-pyridine derivative (1) is converted to an amino-pyridine (2) under a reducing condition such as hydrogenation in the presence of a catalyst Pd/C or Fe powder in aqueous acidic conditions. Compound (2) can then be coupled with sulfonyl chloride (1) to give sulfonamide (4) in the presence of a base such as $Na_2CO_3$, $Et_3N$, or pyridine in an aprotic solvent (for example, $CH_2Cl_2$, $CHCl_3$, etc.), or in pyridine with catalytic amount of DMAP, or under the Schotten-Baumann condition. The subsequent coupling of (4) with bis(pinacolato)diboron (5) in the presence of an approporiate Pd catalyst leads to boronic ester (6).

The synthesis of compound (12) is also demonstrated in Scheme 1. The iodination of halogenated compound (2) with N-iodosuccinimide at room temperature affords iodo compound (8). Iodo compound (8) is then coupled with compound (9) (i.e., acetylene derivatives, cyanide or azide) to give the intermediate (10) under either basic conditions or in the presence of a Pd catalyst. The desired kinase inhibitors (12) are obtained by the coupling of compound (10) with the boronic ester (6) in the presence of an appropriate Pd catalyst (11).

Alternatively, the compounds disclosed herein can be prepared by the method as described in Scheme 2. Compound (7) is first treated with (chloromethylene)dimethyliminium chloride 13) to afford aldehyde (14). Compound (14) is condensed with hydroxylamine hydrochloride (15) to give oxime (16), which is further reacted with acetic anhydride (17) leading to nitrile (18). Coupling of nitrile (18) with boronic ester (6) in the presence of an appropriate Pd catalyst (11) furnishes the desired kinase inhibitors (19).

Scheme 3

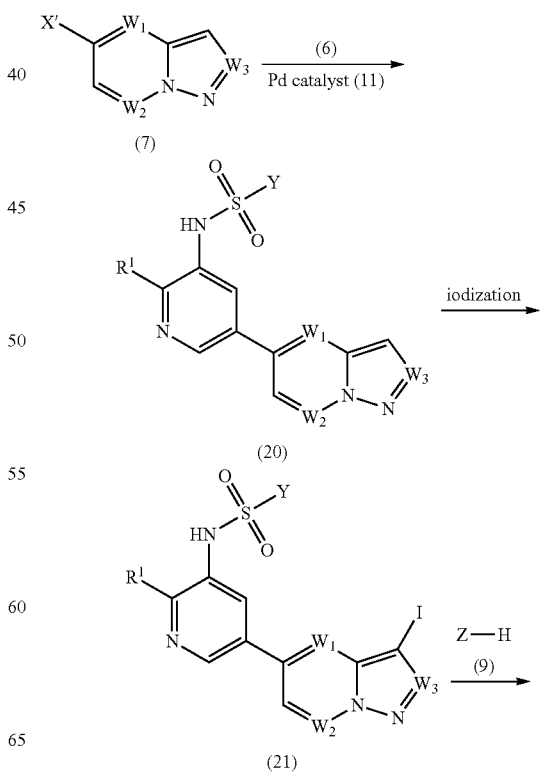

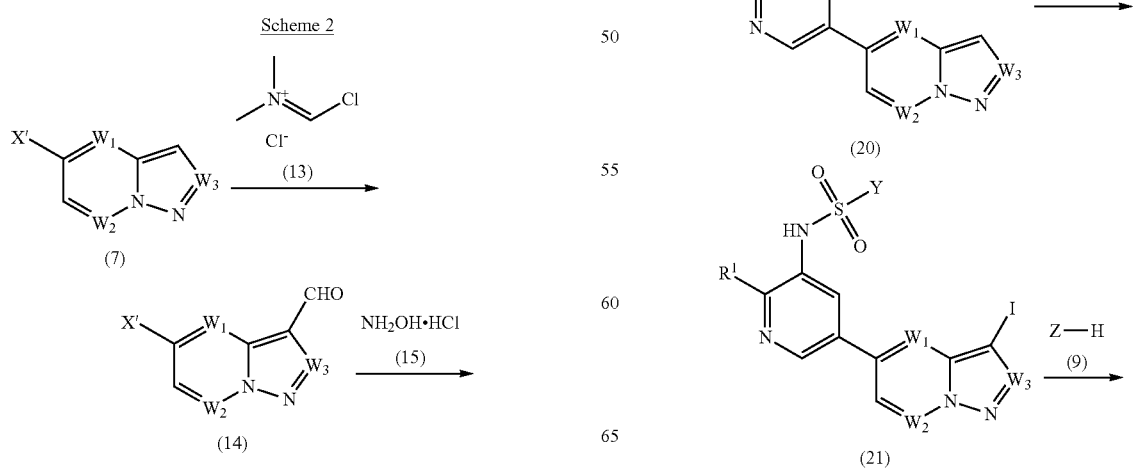

-continued

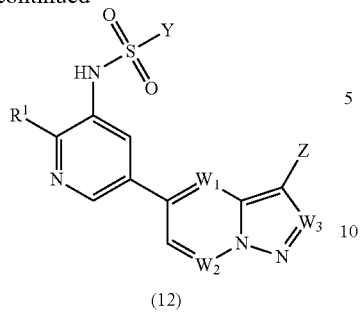

(12)

Scheme 3 shows another method of preparing the kinase inhibitors disclosed herein. The coupling of halogenated compound (2) with the boronic ester (6) in the presence of an appropriate Pd catalyst can give compound (20). The subsequent iodination of compound (20) with N-iodosuccinimide can afford compound (21). Coupling of compound (21) with compound (9) (i.e., acetylene deterivatives, cyanide or azide) under either basic conditions or in the presence of a Pd catalyst affords the desired kinase inhibitors (12).

EXAMPLES

Example 1

2,4-difluoro-N-(5-(3-(3-hydroxyprop-1-yn-1-yl)pyrazolo[1,5-a]pyrimidin-5-yl)-2-methoxypyridin-3-yl)benzenesulfonamide

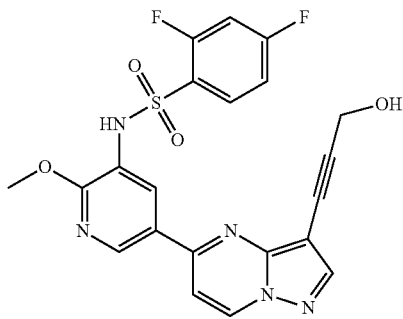 [SMILES: COc1ncc(-c2ccn3ncc(C#CCO)c3n2)cc1NS(=O)(=O)c1ccc(F)cc1F]

Step 1) 5-bromo-2-methoxy-3-nitropyridine

To a solution of sodium methanolate (0.52 g, 9.64 mmol) in MeOH (10 mL) was added 5-bromo-2-chloro-3-nitropyridine (0.57 g, 2.41 mmol) at 0° C. The mixture was stirred at 0° C. for 1 hour, then warmed to rt and stirred for 18 hours. The mixture was quenched with water (20 mL), adjusted to pH=7 with aq. HCl (3 M), and then filtered. The organic phase was separated and concentrated in vacuo to give the title compound as a light yellow solid (0.4 g, 71.4%).

MS (ESI, pos. ion) m/z: 233.0 [M+H]$^+$;
$^1$H NMR (400 MHz, CDCl$_3$) δ (ppm): 3.93 (s, 3H), 8.08 (s, 1H), 8.89 (s, 1H).

Step 2) 5-bromo-2-methoxypyridin-3-amine

To a suspension of 5-bromo-2-methoxy-3-nitropyridine (0.4 g, 1.72 mmol) in EtOH (5 mL) and H$_2$O (5 mL) were added iron powder (0.38 g, 6.87 mmol) and NH$_4$Cl (0.39 g, 7.21 mmol). The reaction was heated to reflux and stirred further for 1 hour, and then concentrated in vacuo. The residue was diluted with EtOAc (10 mL) and the resulted mixture was filtered through a pad of CELITE®. The filtrate was extracted with EtOAc (10 mL×3). The combined organic phases were washed with brine (10 mL), dried over anhydrous Na$_2$SO$_4$ and concentrated in vacuo to give the title compound as a yellow solid (0.30 g, 86%).

MS (ESI, pos. ion) m/z: 203.0 [M+H]$^+$;
$^1$H NMR (400 MHz, CDCl$_3$) δ (ppm): 3.92 (s, 3H), 4.86 (s, 2H), 7.03 (d, J=2.0 Hz, 1H), 7.41 (d, J=2.0 Hz, 1H).

Step 3) N-(5-bromo-2-methoxypyridin-3-yl)-2,4-difluorobenzenesulfonamide

To a solution of 5-bromo-2-methoxypyridin-3-amine (10.15 g, 50 mmol) in pyridine (50 mL) was added 2,4-difluorobenzene-1-sulfonyl chloride (11.68 g, 60 mol) slowly at 0° C. The mixture was stirred at rt for 19 hours and concentrated in vacuo. The residue was dissolved in MeOH (100 mL) and NaOH (2.50 g, 60 mmol). The resulted mixture was stirred at rt for 12 hours and concentrated in vacuo. The residue was dissolved in H$_2$O (50 mL) and the resulted mixture was extracted with DCM (100 mL×3). The combined organic phases were washed with brine (100 mL×3), dried over anhydrous Na$_2$SO$_4$, and concentrated in vacuo to give the title compound as a brown solid (16.90 g, 89.1%).

MS (ESI, pos. ion) m/z: 379.0 [M+H]$^+$.

Step 4) 2,4-difluoro-N-(2-methoxy-5-(4,4,5,5-tetramethyl-1,3,2-dioxaborolan-2-yl)pyridin-3-yl)benzenesulfonamide To a suspension of N-(5-bromo-2-methoxypyridin-3-yl)-2,4-difluorobenzenesulfonamide (16.90 g, 44.6 mmol) in 1,4-dioxane (300 mL) was added bis(pinacolato)diboron (13.59 g, 53.5 mmol), followed by the addition of Pd(dppf)Cl$_2$.CH$_2$Cl$_2$ (3.67 g, 4.5 mmol) and potassium acetate (13.12 g, 133.8 mmol). The reaction mixture was degassed with N$_2$ for 3 times, then heated to 90° C. and stirred further for 7 hours. The mixture was then cooled to rt, quenched with H$_2$O (100 mL) and extracted with EtOAc (500 mL×3). The combined organic phases were washed with brine (500 mL×3), dried over anhydrous Na$_2$SO$_4$, and concentrated in vacuo to give the title compound as a pale yellow solid (24.00 g, 100%).

MS (ESI, pos. ion) m/z: 427.0 [M+H]$^+$.
$^1$H NMR (400 MHz, CDCl$_3$) δ (ppm): 8.25 (d, J=1.0 Hz, 1H), 8.04 (s, 1H), 7.85 (m, 1H), 7.14 (s, 1H), 6.93 (m, 2H), 3.91 (s, 3H), 1.33 (s, 12H).

Step 5) 5-chloro-3-iodopyrazolo[1,5-a]pyrimidine

To a solution of 5-chloropyrazolo[1,5-a]pyrimidine (200 mg, 1.30 mmol) in DMF (2 mL) was added N-iodosuccinimide (322 mg, 1.86 mmol). The reaction was stirred at rt overnight, then diluted with EtOAc (100 mL), and washed with H$_2$O (50 mL), saturated Na$_2$S$_2$O$_3$ aqueous solution (50 mL) and brine (50 mL). The separated organic phase was dried over anhydrous Na$_2$SO$_4$, and concentrated in vacuo. The residue was purified by a silica gel column chromatography (EtOAc/PE (v/v)=1/4) to give the title compound as a pale yellow solid (390 mg, 100%).

MS (ESI, pos. ion) m/z: 279.9 [M+H]$^+$.

$^1$H NMR (400 MHz, CDCl$_3$) δ (ppm): 8.57 (d, J=7.2 Hz, 1H), 8.16 (s, 1H), 6.86 (d, J=7.2 Hz, 1H).

Step 6) 3-(5-chloropyrazolo[1,5-a]pyrimidin-3-yl)prop-2-yn-1-ol

To a suspension of 5-chloro-3-iodopyrazolo[1,5-a]pyrimidine (363 mg, 1.30 mmol), Pd(PPh$_3$)$_2$Cl$_2$ (91 mg, 0.13 mmol), CuI (25 mg, 0.13 mmol) and triethylamine (658 mg, 6.50 mmol) in DMF (15 mL) was added prop-2-yn-1-ol (73 mg, 1.30 mmol). The reaction mixture was degassed with N$_2$ for 3 times and stirred at rt for 20 hours, then quenched with H$_2$O (15 mL) and extracted with EtOAc (50 mL×3). The combined organic phases were washed with brine (50 mL×3), dried over anhydrous Na$_2$SO$_4$, and concentrated in vacuo. The residue was purified by a silica gel column chromatography (EtOAc/PE (v/v)=1/2) to give the title compound as a yellow solid (220 mg, 81.5%).

MS (ESI, pos. ion) m/z: 208.0 [M+H]$^+$.

$^1$H NMR (400 MHz, CDCl$_3$) δ (ppm): 8.58 (d, J=7.4 Hz, 1H), 8.23 (s, 1H), 6.90 (d, J=7.2 Hz, 1H), 4.58 (s, 2H).

Step 7) 2,4-difluoro-N-(5-(3-(3-hydroxyprop-1-yn-1-yl)pyrazolo[1,5-a]pyrimidin-5-yl)-2-methoxypyridin-3-yl)benzenesulfonamide To a suspension of 3-(5-chloropyrazolo[1,5-a]pyrimidin-3-yl)prop-2-yn-1-ol (208 mg, 1 mmol), 2,4-difluoro-N-(2-methoxy-5-(4,4,5,5-tetramethyl-1,3,2-dioxaborolan-2-yl)pyridin-3-yl)benzenesulfonamide (618 mg, 1.5 mmol) and Pd(dppf)Cl$_2$.CH$_2$Cl$_2$ (82 mg, 0.1 mmol) in DME (20 mL) was added a solution of Na$_2$CO$_3$ (318 mg, 3 mmol) in H$_2$O (2.5 mL). The reaction mixture was degassed with N$_2$ for 3 times, then heated to 100° C. and stirred further for 5 hours. The mixture was cooled to rt, quenched with H$_2$O (20 mL), and extracted with EtOAc (500 mL×3). The combined organic phases were washed with brine (50 mL×3), dried over anhydrous Na$_2$SO$_4$, and concentrated in vacuo. The residue was purified by a silica gel column chromatography (EtOAc/PE (v/v)=1/2) to give the title compound as a yellow solid (80 mg, 17%).

MS (ESI, pos. ion) m/z: 472.0 [M+H]$^+$;

$^1$H NMR (400 MHz, DMSO-d$_6$) δ (ppm): 10.46 (s, 1H), 9.23 (d, J=7.4 Hz, 1H), 8.88 (d, J=1.7 Hz, 1H), 8.42 (d, J=2.1 Hz, 1H), 8.41 (s, 1H), 7.82 (dd, J=8.4, 6.2 Hz, 1H), 7.76 (d, J=7.5 Hz, 1H), 7.59 (td, J=10.0, 2.2 Hz, 1H), 7.24 (td, J=8.6, 2.0 Hz, 1H), 5.38 (t, J=5.9 Hz, 1H), 4.41 (d, J=5.9 Hz, 2H), 3.72 (s, 3H).

Example 2

N-(5-(3-cyanopyrazolo[1,5-a]pyrimidin-5-yl)-2-methoxypyridin-3-yl)-2,4-difluorobenzenesulfonamide

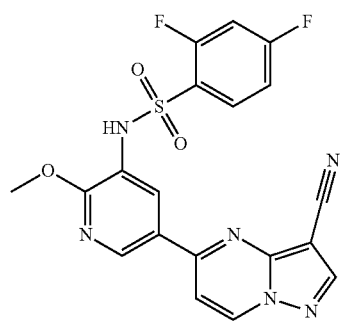 [SMILES: COc1ncc(-c2ccn3ncc(C#N)c3n2)cc1NS(=O)(=O)c1ccc(F)cc1F]

Step 1) 5-chloropyrazolo[1,5-a]pyrimidine-3-carbaldehyde

To a solution of 5-chloropyrazolo[1,5-a]pyrimidine (295 mg, 1.92 mmol) in DCM (10 mL) was added (chloromethylene)dimethyliminium chloride (1.06 g, 6 mmol). The reaction was stirred at 45° C. overnight, and concentrated in vacuo. The residue was dissolved in saturated NaHCO$_3$ aqueous solution (50 mL) and the resulted mixture was then extracted with EtOAc (50 mL×3). The combined organic phases were dried over anhydrous Na$_2$SO$_4$ and concentrated in vacuo to give the title compound as a light yellow solid (380 mg, 100%).

MS (ESI, pos. ion) m/z: 182.2 [M+H]$^+$.

Step 2) (E)-5-chloropyrazolo[1,5-a]pyrimidine-3-carbaldehyde oxime

To a suspension of 5-chloropyrazolo[1,5-a]pyrimidine-3-carbaldehyde (380 mg, 2.1 mmol) in EtOH (20 mL) and H$_2$O (10 mL) was added hydroxylamine hydrochloride (220 mg, 3.15 mmol). The reaction was stirred at 85° C. for 2 hours, and then concentrated in vacuo. The residue was adjusted to pH=7 with saturated NaHCO$_3$ aqueous solution. The resulted mixture was filtered and the filter cake was dried in vacuo to give the title compound as a yellow solid (280 mg, 74.4%).

MS (ESI, pos. ion) m/z: 197.1 [M+H]$^+$.

Step 3) 5-chloropyrazolo[1,5-a]pyrimidine-3-carbonitrile

A solution of (E)-5-chloropyrazolo[1,5-a]pyrimidine-3-carbaldehyde oxime (280 mg, 1.42 mmol) in Ac$_2$O (20 mL) was stirred at 140° C. for 18 hours, then cooled to rt and concentrated in vacuo. The residue was washed with Et$_2$O (20 mL) to give the title compound as a yellow solid (106 mg, 42%).

MS (ESI, pos. ion) m/z: 179.1 [M+H]$^+$.

Step 4) N-(5-(3-cyanopyrazolo[1,5-a]pyrimidin-5-yl)-2-methoxypyridin-3-yl)-2,4-difluorobenzenesulfonamide 2,4-difluoro-N-(2-methoxy-5-(4,4,5,5-tetramethyl-1,3,2-dioxaborolan-2-yl)pyridin-3-yl)benzenesulfonamide (383 mg, 0.9 mmol), 5-chloropyrazolo[1,5-a]pyrimidine-3-carbonitrile (106 mg, 0.6 mmol), Pd(dppf)Cl$_2$.CH$_2$Cl$_2$ (49 mg, 0.06 mmol) and Na$_2$CO$_3$ (254 mg, 2.5 mmol) were placed into a two-neck flask, then degassed with N$_2$ for 3 times, and followed by adding 1,4-dioxane (12 mL) and water (2 mL). The mixture was degassed with N$_2$ for 3 times again, then heated to 90° C. and stirred further for 5 hours. The mixture was cooled to rt, and filtered. The filtrate was concentrated in vacuo and the residue was purified by a silica gel column chromatography (PE/EtOAc (v/v)=4/3) to give the title compound as a light yellow solid (200 mg, 75.3%).

HPLC: 97%;

MS (ESI, pos. ion) m/z: 443.2 [M+H]$^+$;

$^1$H NMR (400 MHz, DMSO-d$_6$) δ (ppm): 10.51 (s, 1H), 9.41 (d, J=7.4 Hz, 1H), 8.93 (d, J=2.1 Hz, 1H), 8.81 (s, 1H), 8.45 (d, J=2.2 Hz, 1H), 7.99 (d, J=7.5 Hz, 1H), 7.85-7.78 (m, 1H), 7.61-7.52 (m, 1H), 7.25 (t, J=8.4 Hz, 1H), 3.77 (s, 3H).

Example 3

N-(5-(3-cyanopyrazolo[1,5-a]pyridin-5-yl)-2-methoxypyridin-3-yl)-2,4-difluorobenzenesulfonamide

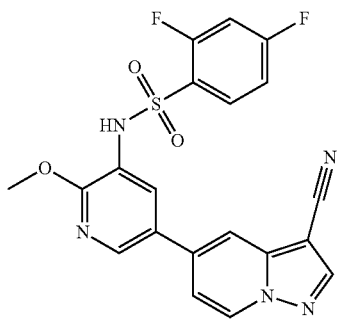 [SMILES: COc1ncc(-c2ccn3ncc(C#N)c3c2)cc1NS(=O)(=O)c1ccc(F)cc1F]

Step 1) 5-bromopyrazolo[1,5-a]pyridine

A solution of ethyl 5-bromopyrazolo[1,5-a]pyridine-3-carboxylate (240 mg, 0.89 mmol) in 40% $H_2SO_4$ (12 mL) was stirred at 100° C. for 4 hours, then cooled to rt, and neutralized to pH=7 with aq. NaOH (6 M) in ice bath. The resulted mixture was extracted with DCM (25 mL×2). The combined organic phases were dried over anhydrous $Na_2SO_4$ and concentrated in vacuo to give the title compound as a light yellow solid (175 mg, 99.5%).

MS (ESI, pos. ion) m/z: 196.9 [M+H]$^+$.

Step 2) 5-bromopyrazolo[1,5-a]pyridine-3-carbaldehyde

To a solution of 5-bromopyrazolo[1,5-a]pyridine (175 mg, 0.89 mmol) in DCM (6 mL) was added (chloromethylene)dimethyliminium chloride (632 mg, 3.56 mmol). The reaction was stirred at 44° C. overnight, and concentrated in vacuo. The residue was dissolved in saturated $NaHCO_3$ aqueous solution (25 mL) and the resulted mixture was then extracted with EtOAc (25 mL×3). The combined organic phases were dried over anhydrous $Na_2SO_4$ and concentrated in vacuo to give the title compound as a light yellow solid (225 mg, 100%).

MS (ESI, pos. ion) m/z: 225.0 [M+H]$^+$.

Step 3) (E)-5-bromopyrazolo[1,5-a]pyridine-3-carbaldehyde oxime

To a suspension of 5-bromopyrazolo[1,5-a]pyridine-3-carbaldehyde (225 mg, 1 mmol) in EtOH (10 mL) and $H_2O$ (5 mL) was added hydroxylamine hydrochloride (104 mg, 1.5 mmol). The reaction was stirred at 85° C. for 2 hours, then cooled to rt, and concentrated in vacuo. The residue was adjusted to pH=7 with saturated $NaHCO_3$ aqueous solution. The resulted mixture was then filtered and the filter cake was dried in vacuo to give title compound as a yellow solid (240 mg, 99%).

MS (ESI, pos. ion) m/z: 240.0 [M+H]$^+$.

Step 4) 5-bromopyrazolo[1,5-a]pyridine-3-carbonitrile

A solution of (E)-5-bromopyrazolo[1,5-a]pyridine-3-carbaldehyde oxime (240 mg, 1 mmol) in $Ac_2O$ (6 mL) was stirred at 140° C. for 18 hours, then cooled to rt, and concentrated in vacuo. The residue was washed with $Et_2O$ (1 mL) to give the title compound as a yellow solid (44 mg, 22.5%).

MS (ESI, pos. ion) m/z: 222.0 [M+H]$^+$.

Step 5) N-(5-(3-cyanopyrazolo[1,5-a]pyridin-5-yl)-2-methoxypyridin-3-yl)-2,4-difluorobenzenesulfonamide 2,4-difluoro-N-(2-methoxy-5-(4,4,5,5-tetramethyl-1,3,2-dioxaborolan-2-yl)pyridin-3-yl)benzenesulfonamide (612 mg, 1.5 mmol), 5-bromopyrazolo[1,5-a]pyridine-3-carbonitrile (222 mg, 1 mmol), Pd(dppf)Cl$_2$.CH$_2$Cl$_2$ (16 mg, 0.02 mmol) and $Na_2CO_3$ (85 mg, 0.8 mmol) were placed into a two-neck flask, then degassed with $N_2$ for 3 times, and followed by adding 1,4-dioxane (5 mL) and water (1 mL). The resulted mixture was degassed with $N_2$ for 3 times, then heated to 90° C. and stirred further for 5 hours. The mixture was cooled to rt and filtered. The filtrate was concentrated in vacuo and the residue was purified by a silica gel column chromatography (PE/EtOAc (v/v)=1/2) to give the title compound as a light yellow solid (400 mg, 81.6%).

MS (ESI, pos. ion) m/z: 442.0 [M+H]$^+$;
$^1$H NMR (400 MHz, DMSO-d$_6$) δ (ppm): 10.37 (s, 1H), 9.02 (d, J=7.2 Hz, 1H), 8.67 (s, 1H), 8.60 (d, J=2.2 Hz, 1H), 8.26-8.16 (m, 2H), 7.82-7.72 (m, 1H), 7.57 (dd, J=13.2, 5.8 Hz, 2H), 7.21 (t, J=8.5 Hz, 1H), 3.67 (s, 3H).

Example 4

2,4-difluoro-N-(5-(3-(3-hydroxyprop-1-yn-1-yl)pyrazolo[1,5-a]pyridin-5-yl)-2-methoxypyridin-3-yl)benzenesulfonamide

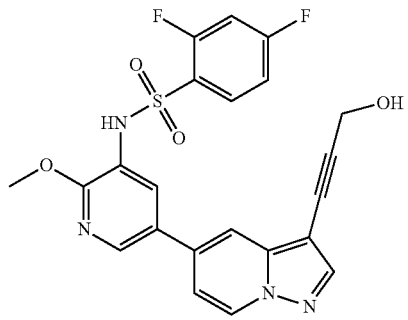 [SMILES: COc1ncc(-c2ccn3ncc(C#CCO)c3c2)cc1NS(=O)(=O)c1ccc(F)cc1F]

Step 1) 5-bromopyrazolo[1,5-a]pyridine

A solution of ethyl 5-bromopyrazolo[1,5-a]pyridine-3-carboxylate (1.2 g, 4.46 mmol) in 40% $H_2SO_4$ (60 mL) was stirred at 100° C. for 4 hours, then cooled to rt, and neutralized to pH=7 with aq. NaOH (6 M) in ice bath. The resulted mixture was extracted with DCM (120 mL×2). The combined organic phases were dried over anhydrous $Na_2SO_4$ and concentrated in vacuo to give the title compound as a light yellow solid (900 mg, 100%).

MS (ESI, pos. ion) m/z: 196.9 [M+H]$^+$.

Step 2) 5-bromo-3-iodopyrazolo[1,5-a]pyridine

To a solution of 5-bromopyrazolo[1,5-a]pyridine (900 mg, 4.46 mmol) in methanol (100 mL) was added N-iodosuccinimide (1 g, 4.46 mmol) slowly at −10° C. The mixture was stirred at −10° C. for 0.5 hour, then warmed to rt and stirred further for 18 hours. The mixture was concentrated in vacuo, and the residue was dissolved in DCM (200 mL). The resulted mixture was washed with a saturated $Na_2S_2O_3$ aqueous solution (200 mL). The separated organic phase was concentrated in vacuo to give the title compound as a light pink solid (1.4 g, 97.5%).

MS (ESI, pos. ion) m/z: 322.8 $[M+H]^+$.

Step 3) 3-(5-bromopyrazolo[1,5-a]pyridin-3-yl)prop-2-yn-1-ol

A mixture of 5-bromo-3-iodopyrazolo[1,5-a]pyridine (644 mg, 2 mmol), prop-2-yn-1-ol (112 mg, 2 mmol), $Pd(PPh_3)_2Cl_2$ (140 mg, 0.2 mmol), CuI (38 mg, 0.2 mmol), and diisopropylethylamine (645 mg, 5 mmol) in DMF (32 mL) was stirred at rt under $N_2$ atmosphere for 3 hours, then diluted with $H_2O$ (200 mL), and extracted with EtOAc (200 mL×3). The combined organic phases were dried over anhydrous $Na_2SO_4$, concentrated in vacuo and the residue was purified by a silica gel column chromatography (pure DCM) to give the title compound as a yellow solid (200 mg, 4%).

MS (ESI, pos. ion) m/z: 251.0 $[M+H]^+$.

Step 4) 2,4-difluoro-N-(5-(3-(3-hydroxyprop-1-yn-1-yl)pyrazolo[1,5-a]pyridin-5-yl)-2-methoxypyridin-3-yl)benzenesulfonamide 2,4-difluoro-N-(2-methoxy-5-(4,4,5,5-tetramethyl-1,3,2-dioxaborolan-2-yl)pyridin-3-yl)benzenesulfonamide (509 mg, 1.2 mmol), 3-(5-bromopyrazolo[1,5-a]pyridin-3-yl)prop-2-yn-1-ol (200 mg, 0.8 mmol), $Pd(dppf)Cl_2 \cdot CH_2Cl_2$ (65 mg, 0.08 mmol) and $Na_2CO_3$ (339 mg, 3.2 mmol) were placed into a two-neck flask, and the mixture was degassed with $N_2$ for 3 times, followed by adding 1,4-dioxane (15 mL) and water (2.5 mL). The resulted mixture was degassed with $N_2$ for 3 times again. The mixture was heated to 90° C. and stirred further for 5 hours, then cooled to rt, and filtered. The filtrate was concentrated in vacuo and the residue was purified by a silica gel column chromatography (PE/EtOAc (v/v)=3/1) to give the title compound as a white solid (122 mg, 32.5%).

HPLC: 91%;
MS (ESI, pos. ion) m/z: 471.0 $[M+H]^+$;
$^1H$ NMR (400 MHz, DMSO-$d_6$) δ (ppm): 10.37 (s, 1H), 8.83 (d, J=7.2 Hz, 1H), 8.53 (d, J=2.3 Hz, 1H), 8.23 (s, 1H), 8.05 (d, J=2.3 Hz, 1H), 7.87 (s, 1H), 7.77 (dd, J=14.8, 8.5 Hz, 1H), 7.59 (dd, J=13.9, 5.9 Hz, 1H), 7.33 (dd, J=7.3, 1.9 Hz, 1H), 7.22 (t, J=8.4 Hz, 1H), 5.33 (t, J=5.9 Hz, 1H), 4.39 (d, J=5.8 Hz, 2H), 3.67 (s, 3H).

Example 5

2,4-difluoro-N-(5-(3-(3-hydroxybut-1-yn-1-yl)pyrazolo[1,5-a]pyrimidin-5-yl)-2-methoxypyridin-3-yl)benzenesulfonamide

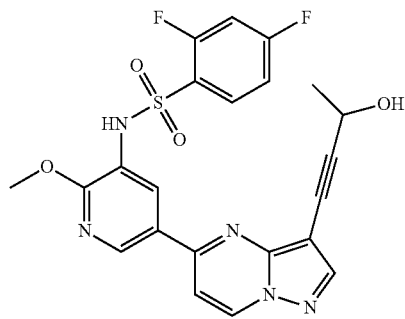 [SMILES: COc1ncc(-c2ccn3ncc(C#CC(C)O)c3n2)cc1NS(=O)(=O)c1ccc(F)cc1F]

Step 1) 2,4-difluoro-N-(2-methoxy-5-(pyrazolo[1,5-a]pyrimidin-5-yl)pyridin-3-yl)benzenesulfonamide To a mixture of 5-chloropyrazolo[1,5-a]pyrimidine (0.46 g, 3.0 mmol) in 60 mL DME were added $Pd(dppf)_2Cl_2 \cdot CH_2Cl_2$ (0.25 g, 0.3 mmol) and a solution of sodium carbonate (0.95 g, 9.0 mmol) in water (8 mL). The mixture was purged with nitrogen several times and then stirred at room temperature for a while. To the resulted solution was added 2,4-difluoro-N-(2-methoxy-5-(4,4,5,5-tetramethyl-1,3,2-dioxaborolan-2-yl)pyridin-3-yl)benzene sulfonamide (1.53 g, 3.6 mmol). The mixture was purged with nitrogen again and stirred at 100° C. for 6 hours, then cooled to rt, and concentrated in vacuo. The residue was purified by a silica gel column chromatography (DCM/MeOH (v/v)=20/1) to give the title compound as a yellow solid (1.24 g, 100%).

MS (ESI, pos. ion) m/z: 418.2 $[M+H]^+$.

Step 2) 2,4-difluoro-N-(5-(3-iodopyrazolo[1,5-a]pyrimidin-5-yl)-2-methoxypyridin-3-yl)benzenesulfonamide To a solution of 2,4-difluoro-N-(2-methoxy-5-(pyrazolo[1,5-a]pyrimidin-5-yl)pyridin-3-yl)benzenesulfonamide (1.98 g, 10.0 mmol) in methanol (50 mL) was added N-iodosuccinimide (2.47 g, 11.0 mmol) portionwise at rt. The mixture was stirred at 45° C. for 10 hours, then concentrated in vacuo, and the residue was diluted with $H_2O$ (40 mL). The resulted mixture was stirred at rt over 2 hours, then filtered, and the collected solid was diluted with PE/EtOAc (40 mL/4 mL). The resulted suspension was stirred at rt for 1 hour, and then filtered to give the title compound as a pale yellow solid (1.05 g, 80.57%).

MS (ESI, pos. ion) m/z: 544.0 $[M+H]^+$;

Step 3) 2,4-difluoro-N-(5-(3-(3-hydroxybut-1-yn-1-yl)pyrazolo[1,5-a]pyrimidin-5-yl)-2-methoxypyridin-3-yl)benzenesulfonamide To a suspension of 2,4-difluoro-N-(5-(3-iodopyrazolo[1,5-a]pyrimidin-5-yl)-2-methoxypyridin-3-yl)benzenesulfonamide (2.32 g, 4.27 mmol), $Pd(PPh_3)_2Cl_2$ (0.31 g, 0.43 mmol) and CuI (82 mg, 0.43 mmol) in 15 mL DMF was added triethylamine (2.15 g, 21.3 mmol). After the mixture was purged with nitrogen several times, but-3-yn-2-ol (1.08 g, 15.4 mmol) was added via a syringe. The mixture was stirred at 50° C. under $N_2$ atmosphere for 6 hours, then quenched with water (40 mL), and the resulted mixture was stirred over 1 hour. Filtered and the filter cake was purified by a silica gel column chromatography (EtOAc/PE (v/v)=1/2) to provide the crude product, which was diluted with a mixture of DCM/MeOH/PE (15 mL/3 mL/65 mL). The resulted mixture was stirred at rt over 2 hours, and then filtered to give the title compound as a pale yellow solid (1.01 g, 48.77%).

MS (ESI, neg. ion) m/z: 484.1 $[M-H]^-$;
$^1H$ NMR (600 MHz, DMSO-$d_6$) δ (ppm): 10.45 (s, 1H), 9.21 (d, J=7.4 Hz, 1H), 8.88 (d, J=2.0 Hz, 1H), 8.44 (d, J=2.0 Hz, 1H), 8.38 (s, 1H), 7.80 (dd, J=14.8, 8.4 Hz, 1H), 7.75 (d, J=7.4 Hz, 1H), 7.58 (t, J=8.8 Hz, 1H), 7.23 (t, J=7.4 Hz, 1H), 4.69 (dd, J=13.1, 6.5 Hz, 1H), 3.72 (s, 3H), 1.45 (d, J=6.6 Hz, 3H).

Example 6

2,4-difluoro-N-(5-(3-(3-hydroxy-3-methylbut-1-yn-1-yl)pyrazolo[1,5-a]pyrimidin-5-yl)-2-methoxypyridin-3-yl)benzenesulfonamide

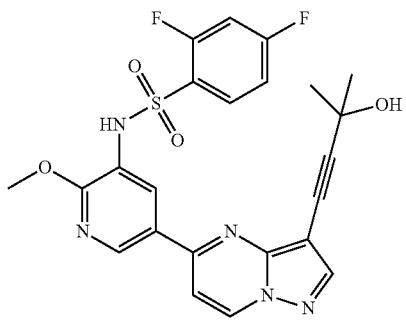 [SMILES: COc1ncc(-c2ccn3ncc(C#CC(C)(C)O)c3n2)cc1NS(=O)(=O)c1ccc(F)cc1F]

To a mixture of 2,4-difluoro-N-(5-(3-iodopyrazolo[1,5-a]pyrimidin-5-yl)-2-methoxypyridin-3-yl)benzenesulfonamide (1.05 g, 1.93 mmol), Pd(PPh$_3$)$_2$Cl$_2$ (0.136 g, 0.19 mmol) and CuI (37 mg, 0.19 mmol) in 5 mL DMF was added diisopropylethylamine (0.98 g, 7.60 mmol). After the mixture was purged with nitrogen several times, 2-methylbut-3-yn-2-ol (0.49 g, 5.79 mmol) was added via a syringe. The mixture was stirred at 50° C. for 4 hours under N$_2$ atmosphere. The reaction mixture was concentrated in vacuo and quenched with water (25 mL). The resulted mixture was stirred over 1 hour and filtered. The collected solid was purified by a silica gel column chromatography (PE/EtOAc (v/v)=3/1) to give the title compound as a yellow solid (520 mg, 53.99%).

MS (ESI, neg. ion) m/z: 498.0 [M−H]$^−$.
HPLC: 96.74%
1H NMR (600 MHz, DMSO-d$_6$) δ (ppm): 10.45 (s, 1H), 9.22 (d, J=7.4 Hz, 1H), 8.89 (d, J=1.8 Hz, 1H), 8.48 (d, J=2.1 Hz, 1H), 8.36 (s, 1H), 7.80 (dd, J=14.8, 8.5 Hz, 1H), 7.76 (d, J=7.4 Hz, 1H), 7.65-7.53 (m, 1H), 7.24 (td, J=8.5, 2.3 Hz, 1H), 5.52 (s, 1H), 3.74 (s, 3H), 1.54 (s, 6H).

Example 7

2,4-difluoro-N-(2-methoxy-5-(3-(prop-1-yn-1-yl)pyrazolo[1,5-a]pyrimidin-5-yl)pyridin-3-yl)benzenesulfonamide

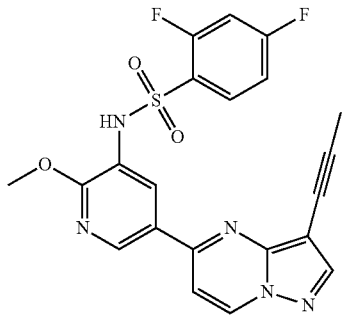 [SMILES: CC#Cc1cnn2ccc(-c3cnc(OC)c(NS(=O)(=O)c4ccc(F)cc4F)c3)nc12]

To a mixture of 2,4-difluoro-N-(5-(3-iodopyrazolo[1,5-a]pyrimidin-5-yl)-2-methoxypyridin-3-yl)benzenesulfonamide (1.50 g, 2.76 mmol), Pd(PPh$_3$)$_2$Cl$_2$ (0.189 g, 0.27 mmol) and CuI (52 mg, 0.27 mmol) in DMF (20 mL) was added diisopropylethylamine (1.78 g, 13.8 mmol). After the mixture was purged with nitrogen several times, propyne (0.44 g, 11.04 mmol) was added via a syringe. The mixture was stirred at 45° C. for 10 hours under N$_2$ atmosphere, then concentrated in vacuo, and quenched with water (40 mL). The resulted mixture was stirred over 1 hour, then filtered, and the collected solid was purified by a silica gel column chromatography (DCM/MeOH (v/v)=300/1) to give the title compound as a yellow solid (220 mg, 17.52%).

MS (ESI, pos. ion) m/z: 456.1 [M+H]$^+$;
$^1$H NMR (600 MHz, DMSO-d$_6$) δ (ppm): 10.46 (s, 1H), 9.18 (d, J=7.3 Hz, 1H), 8.86 (s, 1H), 8.41 (s, 1H), 8.34 (s, 1H), 7.78 (dd, J=14.6, 8.0 Hz, 1H), 7.72 (d, J=7.3 Hz, 1H), 7.58 (t, J=9.1 Hz, 1H), 7.21 (t, J=7.6 Hz, 1H), 3.71 (s, 3H), 2.14 (s, 3H).

Example 8

2,4-difluoro-N-(5-(3-(3-hydroxy-3-methylbut-1-yn-1-yl)pyrazolo[1,5-a]pyridin-5-yl)-2-methoxypyridin-3-yl)benzenesulfonamide

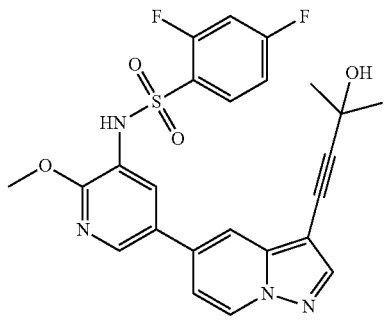 [SMILES: COc1ncc(-c2ccn3ncc(C#CC(C)(C)O)c3c2)cc1NS(=O)(=O)c1ccc(F)cc1F]

Step 1) 2,4-difluoro-N-(2-methoxy-5-(pyrazolo[1,5-a]pyridin-5-yl)pyridin-3-yl)benzenesulfonamide A mixture of 5-bromopyrazolo[1,5-a]pyridine (197 mg, 1 mmol), 2,4-difluoro-N-(2-methoxy-5-(4,4,5,5-tetramethyl-1,3,2-dioxaborolan-2-yl)pyridin-3-yl)benzene sulfonamide (639 mg, 1.5 mmol), Na$_2$CO$_3$ (318 mg, 3.0 mmol) and Pd(PPh$_3$)$_2$Cl$_2$ (35 mg, 0.05 mmol) in 1,4-dioxane/H$_2$O (5 mL/1 mL) was stirred at 90° C. under nitrogen atmosphere, and the reaction was monitored by TLC. After completion, the reaction mixture was cooled to room temperature and extracted with diethyl ether (10 mL). The organic phase was washed with brine (10 mL×2), dried with anhydrous sodium sulfate, and concentrated in vacuo. The residue was purified by a silica gel column chromatography (PE/EtOAc (v/v)=30/1) to give the title compound as a white solid (303 mg, 73%).

MS (ESI, pos. ion) m/z: 416.9 [M+H]$^+$.

Step 2) 2,4-difluoro-N-(5-(3-iodopyrazolo[1,5-a]pyridin-5-yl)-2-methoxypyridin-3-yl)benzenesulfonamide To a solution of 2,4-difluoro-N-(2-methoxy-5-(pyrazolo[1,5-a]pyridin-5-yl)pyridin-3-yl)benzenesulfonamide (2.3 g, 5.52 mmol) in DMF (10 mL) was added N-iodosuccinimide (1.3 g, 5.8 mmol) portionwise at rt. The reaction mixture was stirred at rt for 1.0 hour, then quenched with saturated Na$_2$S2O3 aqueous solution (10 mL), and the resulted mixture was filtered to give the title compound as a white solid (2.87 g, 96%).

MS (ESI, pos. ion) m/z: 542.9 [M+H]$^+$;
$^1$H NMR (600 MHz, CDCl$_3$) δ (ppm): 8.52 (d, J=7.2 Hz, 1H), 8.19 (d, J=2.2, 1H), 8.03-7.98 (m, 2H), 7.97-7.91 (m, 1H) 7.49 (d, J=1.0 Hz, 1H), 7.32 (s, 1H), 7.05-6.91 (m, 2H), 4.00 (s, 3H), 2.80 (s, 1H).

Step 3) 2,4-difluoro-N-(5-(3-(3-hydroxy-3-methyl-but-1-yn-1-yl)pyrazolo[1,5-a]pyridin-5-yl)-2-methoxypyridin-3-yl)benzenesulfonamide A mixture of 2,4-difluoro-N-(5-(3-iodopyrazolo[1,5-a]pyridin-5-yl)-2-methoxypyridin-3-yl)benzenesulfonamide (1.0 g, 1.85 mmol), 2-methylbut-3-yn-2-ol (0.23 g, 2.76 mmol), Pd(PPh$_3$)$_2$Cl$_2$ (0.13 g, 0.19 mmol), CuI (36 mg, 0.19 mmol), and diisopropylethylamine (0.74 g, 0.57 mmol) in DMF (20 mL) was stirred at rt for 3 hours under N$_2$ atmosphere. Then the mixture was concentrated in vacuo and the residue was purified by a silica gel column chromatography (PE/EtOAc (v/v)=10/1) to give the title compound as a pale yellow solid (0.42 g, 46%).

MS (ESI, pos. ion) m/z: 499.0 [M+H]$^+$;
$^1$H NMR (600 MHz, CDCl$_3$) δ (ppm): 8.52 (d, J=6.1 Hz, 1H), 8.20 (d, J=2.1 Hz, 1H), 8.08 (s, 1H), 8.03 (d, J=2.1 Hz, 1H), 7.92 (dd, J=14.5, 8.3 Hz, 1H), 7.68 (s, 1H), 7.59-7.52 (m, 1H), 7.51-7.42 (m, 1H), 7.05-6.94 (m, 2H), 4.00 (s, 3H), 1.60 (s, 6H).

Example 9

N-(5-(3-cyanopyrazolo[1,5-a]pyridin-5-yl)-2-methoxypyridin-3-yl)cyclopropanesulfonamide

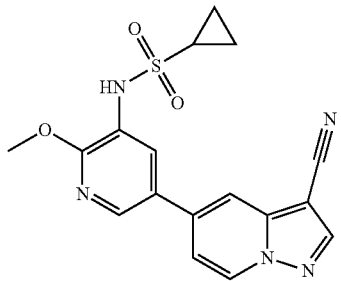 [SMILES: COc1ncc(-c2ccn3ncc(C#N)c3c2)cc1NS(=O)(=O)C1CC1]

To a solution of 5-bromopyrazolo[1,5-a]pyridine-3-carbonitrile (50 mg, 0.225 mmol) in 1,4-dioxane (5 mL) and water (0.5 mL) were added N-(2-methoxy-5-(4,4,5,5-tetramethyl-1,3,2-dioxaborolan-2-yl)pyridin-3-yl)cyclopropanesulfonamide (96 mg, 0.270 mmol), Na$_2$CO$_3$ (48 mg, 0.45 mmol) and Pd(dppf)Cl$_2$.CH$_2$Cl$_2$ (37 mg, 0.045 mmol) under N$_2$ atmosphere. The reaction was stirred at 90° C. for 3.5 hours under N$_2$ atmosphere, then cooled to rt and stirred overnight. The mixture was diluted with EtOAc (30 mL), filtered through a pad of CELITE®, and the filter cake was washed with EtOAc (20 mL). The filtrate was washed with H$_2$O (30 mL) and brine (30 mL). Then the separated organic phase was dried over anhydrous Na$_2$SO$_4$, and concentrated in vacuo. The residue was purified by a silica gel column chromatography (DCM/EtOAc (v/v)=10/1) to give the title compound as a white solid (55 mg, 66%).

MS (ESI, pos. ion) m/z: 370.0 [M+H]$^+$;
$^1$H NMR (300 MHz, CDCl$_3$) δ (ppm): 8.61 (d, J=7.26 Hz, 1H), 8.27-8.25 (m, 2H), 8.09 (d, J=2.07 Hz, 1H), 7.87 (s, 1H), 7.21 (dd, J=1.77, 7.35 Hz, 1H), 6.80 (br s, 1H), 4.11 (s, 3H), 2.60-2.51 (m, 1H), 1.33-1.22 (m, 2H), 1.07-0.99 (m, 2H).

Example 10

N-(5-(3-cyanopyrazolo[1,5-a]pyridin-5-yl)-2-methoxypyridin-3-yl)-2,2,2-trifluoroethanesulfonamide

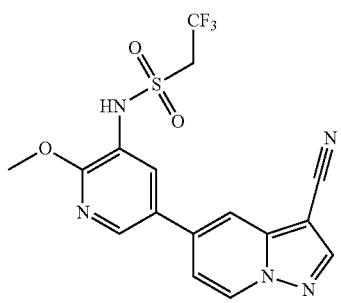 [SMILES: COc1ncc(-c2ccn3ncc(C#N)c3c2)cc1NS(=O)(=O)CC(F)(F)F]

Step 1) N-(5-bromo-2-methoxypyridin-3-yl)-2,2,2-trifluoroethanesulfonamide

To a solution of 5-bromo-2-methoxypyridin-3-amine (500 mg, 2.46 mmol) in pyridine (10 mL) was added 2,2,2-trifluoroethanesulfonyl chloride (898 mg, 4.92 mmol) dropwise. The reaction was stirred at rt for 18 hours, then concentrated in vacuo, and the residue was diluted with water (30 mL). The resulted mixture was extracted with DCM (20 mL×3). The combined organic phases were washed with water (25 mL×2) and brine (25 mL), dried over anhydrous Na$_2$SO$_4$, and concentrated in vacuo to give the title compound as a yellow solid (859 mg, 100%) which was directly used in the next step reaction without further purification.

MS (ESI, pos. ion) m/z: 348.9 [M+H]$^+$;
$^1$H NMR (300 MHz, CDCl$_3$) δ (ppm): 8.03 (d, J=2.19 Hz, 1H), 7.91 (d, J=2.22 Hz, 1H), 7.00 (br s, 1H), 4.00 (s, 3H), 3.87 (q, J=8.73 Hz, 2H).

Step 2) 2,2,2-trifluoro-N-(2-methoxy-5-(4,4,5,5-tetramethyl-1,3,2-dioxaborolan-2-yl)pyridin-3-yl)ethanesulfonamide A mixture of N-(5-bromo-2-methoxypyridin-3-yl)-2,2,2-trifluoroethanesulfonamide (500 mg, 1.43 mmol), 4,4,4',4',5,5,5',5'-octamethyl-2,2'-bi-1,3,2-dioxaborolane (1.45 g, 5.729 mmol) and KOAc (562 mg, 5.729 mmol) in 1,4-dioxane (10 mL) was purged with nitrogen several times, and then Pd(dppf)Cl$_2$.CH$_2$Cl$_2$ (248 mg, 0.304 mmol) was added. The reaction was stirred at 80° C. for 3.5 hours, and concentrated in vacuo. The residue was dissolved in DCM (50 mL). The resulted mixture was filtered through a pad of CELITE®, and the filtrate was washed with water (25 mL×3) and brine (35 mL). The separated organic phase was dried over anhydrous Na$_2$SO$_4$ and concentrated in vacuo. The residue was purified by a silica gel column chromatography (PE/EtOAc (v/v)=5/1) to give the title compound as yellow oil (395 mg, 70%).

MS (ESI, pos. ion) m/z: 397.0 [M+H]$^+$;
$^1$H NMR (300 MHz, CDCl$_3$) δ (ppm): 8.36 (d, J=1.59 Hz, 1H), 8.05 (d, J=1.59 Hz, 1H), 6.94 (br s, 1H), 4.04 (s, 3H), 3.85 (q, J=7.82 Hz, 2H), 1.33 (s, 12H).

Step 3) N-(5-(3-cyanopyrazolo[1,5-a]pyridin-5-yl)-2-methoxypyridin-3-yl)-2,2,2-trifluoroethanesulfonamide To a solution of 5-bromopyrazolo[1,5-a]pyridine-3-carbonitrile (100 mg, 0.450 mmol) in 1,4-dioxane (20 mL) and water (4 mL) were added 2,2,2-trifluoro-N-(2-methoxy-5-(4,4,5,5-tetramethyl-1,3,2-dioxaborolan-2-yl)pyridin-3-yl)ethanesulfonamide (196 mg, 0.495 mmol), KOAc (88 mg, 0.900 mmol) and Pd(dppf)Cl$_2$.CH$_2$Cl$_2$ (74 mg, 0.09 mmol) under N$_2$ atmosphere. The reaction was stirred at 90° C. for 2.5 hours under N$_2$ atmosphere, then cooled to rt and stirred overnight. The mixture was concentrated in vacuo, then the residue was diluted with EtOAc (35 mL), and the resulted mixture was filtered through a pad of CELITE®. The filter cake was washed with EtOAc (35 mL) and the filtrate was washed with H$_2$O (15 mL) and brine (20 mL). The separated organic phase was dried over anhydrous Na$_2$SO$_4$, and concentrated in vacuo. The residue was purified by a silica gel column chromatography (PE/EtOAc (v/v)=2.5/1) to give the title compound as a yellow solid (94 mg, 51%).

MS (ESI, pos. ion) m/z: 412.0 [M+H]$^+$;
$^1$H NMR (300 MHz, DMSO-d$_6$) δ (ppm): 10.15 (s, 1H), 9.03 (d, J=7.32 Hz, 1H), 8.67 (s, 1H), 8.65 (d, J=2.25 Hz, 1H), 8.24 (d, J=1.05 Hz, 1H), 8.18 (d, J=2.28 Hz, 1H), 7.59 (dd, J=1.80, 7.26 Hz, 1H), 4.63 (q, J=9.78 Hz, 2H), 4.00 (s, 3H).

Example 11

N-(2-chloro-5-(3-cyanopyrazolo[1,5-a]pyridin-5-yl)pyridin-3-yl)-2,4-difluorobenzenesulfonamide

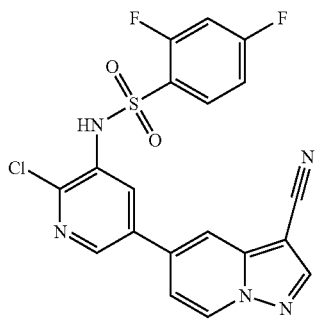 [SMILES: N#Cc1cnn2ccc(-c3cnc(Cl)c(NS(=O)(=O)c4ccc(F)cc4F)c3)cc12]

To a solution of 5-bromopyrazolo[1,5-a]pyridine-3-carbonitrile (110 mg, 0.5 mmol) in 1,4-dioxane (20 mL) were added N-(2-chloro-5-(4,4,5,5-tetramethyl-1,3,2-dioxaborolan-2-yl)pyridin-3-yl)-2,4-difluorobenzenesulfonamide (235 mg, 0.55 mmol), KOAc (98 mg, 1 mmol), H$_2$O (2 mL) and Pd(dppf)Cl$_2$.CH$_2$Cl$_2$ (81 mg, 0.1 mmol). The reaction was stirred at 93° C. under N$_2$ atmosphere for 2 hours, then concentrated in vacuo, and the residue was extracted with EtOAc (20 mL×3). The combined organic phases were dried anhydrous Na$_2$SO$_4$, and concentrated in vacuo. The residue was purified by a silica gel column chromatography (PE/EtOAc (v/v)=4.5/1) to give the title compound as a white solid (130 mg, 59%).

MS (ESI, pos. ion) m/z: 446.0 [M+H]$^+$;
$^1$H NMR (300 MHz, DMSO-d$_6$) δ (ppm): 10.98 (br s, 1H), 9.08 (d, J=7.29 Hz, 1H), 8.87 (d, J=2.67 Hz, 1H), 8.71 (s, 1H), 8.41-8.39 (m, 2H), 7.84-7.76 (m, 1H), 7.63-7.54 (m, 2H), 7.26-7.20 (m, 1H).

Biological Testing

The efficacy of the compounds disclosed herein as inhibitors of PI3 kinases and mTOR kinases can be evaluated as follows. The assay results demonstrate that certain compounds disclosed herein potently inhibit PI3Ks and mTOR.

The LC/MS/MS system used in the analysis consists of an Agilent 1200 Series vacuum degasser, binary pump, well-plate autosampler, thermostatted column compartment, the Agilent G6430 Triple Quadrupole Mass Spectrometer with an electrospray ionization (ESI) source. Quantitative analysis was carried out using MRM mode. The parameters for MRM transitions are in the Table A.

TABLE A

| MRM | 490.2→383.1 |
|---|---|
| Fragmentor | 230 V |
| CE | 55 V |
| Drying Gas Temp | 350° C. |
| Nebulize | 40 psi |
| Drying Gas Flow | 10 L/min |

An Agilent XDB-C18, 2.1×30 mm, 3.5 μM column was used for the analysis. 5 μL of the samples were injected. Analysis condition: The mobile phase was 0.1% formic acid in water (A) and 0.1% formic acid in methanol (B). The flow rate was 0.4 mL/min. And the gradient of Mobile phase was in the Table B.

TABLE B

| Time | Gradient of Mobile Phase B |
|---|---|
| 0.5 min | 5% |
| 1.0 min | 95% |
| 2.2 min | 95% |
| 2.3 min | 5% |
| 5.0 min | stop |

Alternatively, an Agilent 6330 series LC/MS/MS spectrometer equipped with G1312A binary pumps, a G1367A autosampler and a G1314C UV detector were used in the analysis. An ESI source was used on the LC/MS/MS spectrometer. The analysis was done in positive ion mode as appropriate and the MRM transition for each analyte was optimized using standard solution. A Capcell MP-C18 100× 4.6 mm I.D., 5 μM column (Phenomenex, Torrance, Calif., USA) was used during the analysis. The mobile phase was 5 mM ammonia acetate, 0.1% MeOH in water (A): 5 mM ammonia acetate, 0.1% MeOH in acetonitrile (B) (70/30, v/v). The flow rate was 0.6 mL/min. Column was maintained at ambient temperature. 20 μL of the samples were injected.

Example A

Compound Stability in Human and Rat Liver Microsomes

Human or rat liver microsomes incubations were conducted in duplicate in polypropylene tubes. The typical incubation mixtures consisted of human or rat liver microsomes (0.5 mg protein/mL), compounds of interest (5 μM) and NADPH (1.0 mM) in a total volume of 200 μL potassium phosphate buffer (PBS, 100 mM, pH=7.4). Compounds were dissolved in DMSO and diluted with PBS such that the final concentration of DMSO was 0.05%. The enzymatic reactions were commenced with the addition of protein after a 3-min preincubation and incubated in a water bath open to the air at 37° C. Reactions were terminated at various time points (0, 5, 10, 15, 30, 60 min) by adding equal volume of ice-cold acetonitrile. The samples were stored at −80° C. until LC/MS/MS assays.

The concentrations of compounds in the incubation mixtures of human or rat liver microsomes were determined by a LC/MS/MS method. The ranges of the linearity in the concentration range were determined for each tested compounds.

A parallel incubation was performed using denatured microsomes as the negative control, and reactions were terminated at various time points (0, 15, 60 min) after incubation at 37° C.

Dextromethorphan (70 μM) was selected as the positive control, and reactions were terminated at various time points (0, 5, 10, 15, 30, 60 min) after incubation at 37° C. Both positive and negative control samples were included in each assay to ensure the integrity of the microsomal incubation system.

Data Analysis

The concentrations of compounds in human or rat liver microsome incubations were plotted as a percentage of the relevant zero time point control for each reaction. The in vivo $CL_{int}$ were extrapolated (ref.: Naritomi Y, Terashita S, Kimura S, Suzuki A, Kagayama A, Sugiyama Y. "Prediction of human hepatic clearance from in vivo animal experiments and in vitro metabolic studies with liver microsomes from animals and humans", *Drug Metabolism and Disposition*, 2001, 29, 1316-1324).

TABLE 2

Human and rat liver microsomes stability

| | Human | | Rat | |
|---|---|---|---|---|
| Example # | $T_{1/2}$ (min) | $CL_{int}$ (mL/min/kg) | $T_{1/2}$ (min) | $CL_{int}$ (mL/min/kg) |
| Ex. 1 | 710.7 | 2.45 | 175.4 | 14.16 |
| Ex. 2 | ∞ | N/A | ∞ | N/A |
| Ex. 3 | 2404 | 0.72 | 575.1 | 4.32 |
| Ex. 4 | 299.2 | 5.81 | 153.3 | 16.20 |
| Ex. 5 | 303.0 | 5.74 | 216.7 | 11.46 |
| Ex. 6 | ∞ | N/A | ∞ | N/A |
| Ex. 7 | 3344 | 0.52 | 92.42 | 26.87 |
| Ex. 8 | 7825 | 0.22 | 1262 | 1.97 |
| Ex. 10 | 1223 | 2.03 | ∞ | N/A |

Example B

Evaluation of Pharmacokinetics after Intravenous and Oral Administration of the Compounds Disclosed Herein in Mice, Rats, Dogs and Monkeys The compounds disclosed herein are assessed in pharmacokinetic studies in mice, rats, dogs or monkeys. The compounds are administered as a water solution, 2% HPMC+1% TWEEN®80 in water solution, 5% DMSO+5% solutol in saline, 4% MC suspension or capsule. For the intravenous administration, the animals are generally given at 1 or 2 mg/kg dose. For the oral (p.o.) dosing, mice and rats are generally given 5 or 10 mg/kg dose, and dogs and monkeys are generally given 10 mg/kg dose. The blood samples (0.3 mL) are drawn at 0.25, 0.5, 1.0, 2.0, 3.0, 4.0, 6.0, 8.0, 12 and 24 h time points or 0.083, 0.25, 0.5, 1.0, 2.0, 4.0, 6.0, 8.0 and 24 h time points and centrifuged at 3,000 or 4000 rpm for 2 to 10 min. The plasma solutions are collected and stored at −20° C. or −70° C. until analyzed by LC/MS/MS as described above.

TABLE 3

Pharmacokinetic profiles in rats

| | | | iv dosing | | | |
|---|---|---|---|---|---|---|
| Example # | dose (mg/kg) | $T_{1/2}$ (h) | $AUC_{last}$ (ng · h/ml) | Cl/F (L/h/kg) | Vss (L/kg) | F % |
| Ex. 1 | 2 | 3.93 | 12121 | 0.17 | 0.32 | 102.00 |
| Ex. 2 | 2 | 3.70 | 7720 | 0.26 | 0.80 | 69.48 |
| Ex. 3 | 2 | 2.77 | 7069 | 0.29 | 0.85 | 94.75 |
| Ex. 4 | 2 | 1.93 | 7353 | 0.28 | 0.48 | 91.75 |
| Ex. 5 | 2 | 3.00 | 35176 | 0.05 | 0.20 | 96.20 |
| Ex. 6 | 1 | 10.96 | 40869 | 0.02 | 0.24 | 50.80 |
| Ex. 7 | 1 | 3.94 | 5328 | 0.19 | 0.63 | 80.10 |
| Ex. 8 | 1 | 10.77 | 41751 | 0.02 | 0.28 | 103.40 |
| Ex. 10 | 1 | 2.74 | 1240 | 0.76 | 1.72 | 112.95 |

TABLE 4

Pharmacokinetic profiles in Mice, Dogs and Monkeys

| | | | | iv dosing | | | |
|---|---|---|---|---|---|---|---|
| Example # | Species | dose (mg/kg) | $T_{1/2}$ (h) | $AUC_{last}$ (ng · h/ml) | Cl/F (L/h/kg) | Vss (L/kg) | F % |
| Ex. 3 | Mouse | 1 | 5.45 | 57059 | 0.02 | 0.13 | 79.3 |
| | Dog | 1 | 0.67 | 3672 | 0.27 | 0.23 | 108.5 |
| | Monkey | 1 | 9.70 | 5978 | 0.16 | 0.92 | 59.8 |
| Ex. 4 | Mouse | 1 | 1.11 | 5812 | 0.17 | 0.18 | 70.0 |
| | Dog | 1 | 6.13 | 9069 | 0.11 | 0.19 | 108.5 |
| | Monkey | 1 | 4.64 | 5739 | 0.18 | 0.42 | 24.0 |

Example C

Kinase Activity Assay

The efficacy of the compounds disclosed herein as inhibitors of PI3 kinases and mTOR kinases can be evaluated as follows.

General Description for Kinase Assays

Kinase assays can be performed by measurement of incorporation of γ-$^{33}$P ATP into immobilized myelin basic protein (MBP). High binding white 384 well plates (Greiner) are coated with MBP (Sigma #M-1891) by incubation of 60 μL/well of 20 μg/mL MBP in Tris-buffered saline (TBS; 50 mM Tris pH 8.0, 138 mM NaCl, 2.7 mM KCl) for 24 h at 4° C. Plates are washed 3× with 100 μL TBS. Kinase reactions are carried out in a total volume of 34 μL in kinase buffer (5 mM Hepes pH 7.6, 15 mM NaCl, 0.01% bovine gamma globulin (Sigma #I-5506), 10 mM MgCl$_2$, 1 mM DTT, 0.02% TritonX-100). Compound dilutions are performed in DMSO and added to assay wells to a final DMSO concentration of 1%. Each data point is measured in duplicate, and at least two duplicate assays are performed for each individual compound determination. Enzyme is added to final concentrations of 10 nM or 20 nM, for example. A mixture of unlabeled ATP and γ-$^{33}$P ATP is added to start the reaction (2×10$^6$ cpm of γ-$^{33}$P ATP per well (3000 Ci/mmole) and 10 μM unlabeled ATP, typically. The reactions are carried out for 1 hour at rt with shaking Plates are washed 7× with TBS, followed by the addition of 50

μL/well scintillation fluid (Wallac). Plates are read using a Wallac Trilux counter. This is only one format of such assays; various other formats are possible, as known to one skilled in the art.

The above assay procedure can be used to determine the $IC_{50}$ for inhibition and/or the inhibition constant, $K_i$. The $IC_{50}$ is defined as the concentration of compound required to reduce the enzyme activity by 50% under the condition of the assay. The $IC_{50}$ value is estimated by preparing a 10 point curve using a ½ log dilution series (for example, a typical curve may be prepared using the following compound concentrations: 10 μM, 3 μM, 1 μM, 0.3 μM, 0.1 μM, 0.03 μM, 0.01 μM, 0.003 μM, 0.001 μM and 0 μM).

PI3 Kianse General Assay Protocol

PI3K p110α/p85α (h) [Non-Radioactive Assay]

PI3K p110α/p85α (h) is incubated in assay buffer containing 10 μM phosphatidylinositol 4,5-bisphosphate and MgATP (concentration as required). The reaction is initiated by the addition of the ATP solution. After incubation for 30 minutes at room temperature, the reaction is stopped by the addition of stop solution containing EDTA and biotinylated phosphatidylinositol-3,4,5-trisphosphate. Finally, detection buffer is added, which contains europium-labelled anti-GST monoclonal antibody, GST-tagged GRP1 PH domain and streptavidin allophycocyanin. The plate is then read in time-resolved fluorescence mode and the homogenous time-resolved fluorescence (HTRF) signal is determined according to the formula HTRF=10000×(Em665 nm/Em620 nm).

PI3K p110β/p85α (h) [Non-Radioactive Assay]

PI3K (p110β/p85α) (h) is incubated in assay buffer containing 10 μM phosphatidylinositol-4,5-bisphosphate and MgATP (concentration as required). The reaction is initiated by the addition of the MgATP mix. After incubation for 30 minutes at room temperature, the reaction is stopped by the addition of stop solution containing EDTA and biotinylated phosphatidylinositol-3,4,5-trisphosphate. Finally, detection buffer is added, which contains europium-labelled anti-GST monoclonal antibody, GST-tagged GRP1 PH domain and streptavidin-allophycocyanin. The plate is then read in time-resolved fluorescence mode and the homogenous time-resolved fluorescence (HTRF) signal is determined according to the formula HTRF=10000×(Em665 nm/Em620 nm).

PI3K (p110δ/p85α) (h) [Non-Radioactive Assay]

PI3K (p110δ/p85α) (h) is incubated in assay buffer containing 10 μM phosphatidylinositol-4,5-bisphosphate and MgATP (concentration as required). The reaction is initiated by the addition of the MgATP mix. After incubation for 30 minutes at room temperature, the reaction is stopped by the addition of stop solution containing EDTA and biotinylated phosphatidylinositol-3,4,5-trisphosphate. Finally, detection buffer is added, which contains europium-labelled anti-GST monoclonal antibody, GST-tagged GRP1 PH domain and streptavidin-allophycocyanin. The plate is then read in time-resolved fluorescence mode and the homogenous time-resolved fluorescence (HTRF) signal is determined according to the formula HTRF=10000×(Em665 nm/Em620 nm).

PI3K (p120γ) (h) [Non-Radioactive Assay]

PI3K (p120γ) (h) is incubated in assay buffer containing 10 μM phosphatidylinositol-4,5-bisphosphate and MgATP (concentration as required). The reaction is initiated by the addition of the MgATP mix. After incubation for 30 minutes at room temperature, the reaction is stopped by the addition of stop solution containing EDTA and biotinylated phosphatidylinositol-3,4,5-trisphosphate. Finally, detection buffer is added, which contains europium-labelled anti-GST monoclonal antibody, GST-tagged GRP1 PH domain and streptavidin-allophycocyanin. The plate is then read in time-resolved fluorescence mode and the homogenous time-resolved fluorescence (HTRF) signal is determined according to the formula HTRF=10000×(Em665 nm/Em620 nm).

mTOR (h)

mTOR (h) is incubated with 50 mM HEPES pH 7.5, 1 mM EDTA, 0.01% TWEEN®20, 2 mg/mL substrate, 3 mM Manganese Chloride and [γ-$^{33}$P-ATP] (specific activity approx. 500 cpm/pmol, concentration as required). The reaction is initiated by the addition of the MnATP mix. After incubation for 40 minutes at room temperature, the reaction is stopped by the addition of 3% phosphoric acid solution. Aliquote of the reaction (10 μL) is then spotted onto a P30 filtermat and washed three times for 5 minutes in 75 mM phosphoric acid and once in methanol prior to drying and scintillation counting.

The kinase assays described herein were performed at Millipore UK Ltd, Dundee Technology Park, Dundee DD2 1SW, UK.

The compounds disclosed herein exhibited potent activities in the PI3Kα(h) and mTOR (h) assays. Table 5 listed the $IC_{50}$s of some examples described herein in the PI3Kα(h) and mTOR (h) assays.

TABLE 5

Kinase inhibition data

| | | | $IC_{50}$(nM) | | |
| | | | PI3K | | |
| Example # | mTOR | p110α/p85α | p110β/p85α | p110δ/p85α | p120γ |
| --- | --- | --- | --- | --- | --- |
| Ex. 1 | 9 | 4 | 84 | 5 | 6 |
| Ex. 2 | 4 | 4 | 45 | 5 | 5 |
| Ex. 3 | 4 | 4 | 41 | 2 | 6 |
| Ex. 4 | 4 | 1 | 22 | 1 | 15 |
| Ex. 5 | 7 | 3 | 75 | 1 | 6 |

Alternatively, the kinase activities of the compounds can be measured using KINOMEscan™, which is based on a competition binding assay that quantitatively measures the ability of a compound to compete with an immobilized, active-site directed ligand. The assay was performed by combining three components: DNA-tagged kinase; immobilized ligand; and a test compound. The ability of the test compound to compete with the immobilized ligand was measured via quantitative PCR of the DNA tag.

For most assays, kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. The remaining kinases were produced in HEK-293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SEABLOCK™ (Pierce), 1% BSA, 0.05% TWEEN®20, 1 mM DTT) to remove unbound ligand and to reduce nonspecific binding. Binding reactions were assembled by combining kinases, liganded affinity beads, and test compounds in 1× binding buffer (20% SEA-BLOCK™, 0.17×PBS, 0.05% TWEEN®20, 6 mM DTT). All reactions were performed in polystyrene 96-well plates in a final volume of 0.135 mL. The assay plates were incubated at room temperature with shaking for 1 hour and the affinity beads were washed with wash buffer (1×PBS, 0.05% TWEEN® 20). The beads were then re-suspended in elution buffer (1×PBS, 0.05% TWEEN®20, 0.5 μM non-biotinylated affinity ligand) and incubated at room temperature with shaking for 30 minutes. The kinase concentration in the eluates was measured by qPCR.

The kinase assays described herein were performed using KINOMEscan™ Profiling Service at DiscoveRx Corporation, 42501 Albrae St. Fremont, Calif. 94538, USA.

Example D

Tumor Xenograft Models

The efficacy of compounds disclosed herein was evaluated in a standard murine model of tumorigenesis. Human tumor cells (U87MG glioblastoma cells from ATCC) were expended in culture, harvested, and injected subcutaneously onto the rear flank of 6-7 week old female athymic nude mice (BALB/cA nu/nu, Hunan SLAC Laboratory Animal, Co.) (n=6-10 for vehicle group and for each dosing group). When tumors reached a volume of 100-250 mm³, animals were randomly divided into vehicle control (for example, 5% DMSO+70% CAPTISOL® (30%), 7% HCl (pH1), 18% CAPTISOL® (30%); or 7% DMSO, 7% HCl (pH1), 70% CAPTISOL® (30%), 16% CAPTISOL® (30%), or the like) and compound groups. Subsequent administration of compound by oral gavage begins anywhere from day 0 to day 15 post tumor cell challenge and generally continues with once a day for the duration of the experiment.

Tumor Growth Inhibition (TGI) Analysis

Progression of tumor growth is assessed by tumor volumes and recorded as a function of time. The long (L) and short (W) axes of the subcutaneous tumors were measured with calipers twice weekly, and the tumor volume (TV) calculated as (L×W²)/2). TGI was calculated from the difference between the median tumor volumes of vehicle-treated and drug-treated mice, expressed as a percentage of the median tumor volume of the vehicle-treated control group, by the following relation:

$$\%TGI = \left( \frac{\text{Median Tumor Volume}_{control} - \text{Median Tumor Volume}_{drug\text{-}treated}}{\text{Median Tumor Volume}_{control}} \right) \times 100$$

Initial statistical analysis is done by repeated measures analysis of variance (RMANOVA), followed by Scheffe post hoc testing for multiple comparisons. Vehicle alone (5% DMSO+70% CAPTISOL® (30%), 7% HCl (pH1), 18% CAPTISOL® (30%); or 7% DMSO, 7% HCl (pH1), 70% CAPTISOL® (30%), 16% CAPTISOL® (30%), or the like) is the negative control.

TABLE 6

Selected results from tumor xenograft model (U87MG) studies

| Example # | Dosing (mg/kg) | TGI % U87MG |
|---|---|---|
| Ex. 1 (12 days) | 1 | 26 |
| | 3 | 37 |
| | 10 | 68 |
| Ex. 2 (12 days) | 1 | 59 |
| | 3 | 76 |
| Ex. 3 (13 days) | 0.3 | 26 |
| | 1 | 70 |

TABLE 6-continued

Selected results from tumor xenograft model (U87MG) studies

| Example # | Dosing (mg/kg) | TGI % U87MG |
|---|---|---|
| | 3 | 95 |
| Ex. 4 (13 days) | 1 | 32 |
| | 3 | 53 |
| | 10 | 89 |

Finally, it should be noted that there are alternative ways of implementing the present invention. Accordingly, the present embodiments are to be considered as illustrative and not restrictive, and the invention is not be limited to the details given herein, but may be modified within the scope and equivalents of the appended claims. All publications and patents cited herein are incorporated by reference.

What is claimed is:

1. A compound having Formula (I):

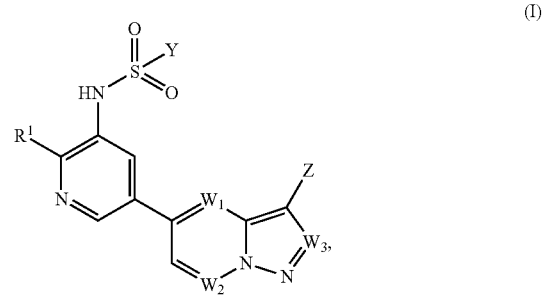

(I)

or a stereoisomer, a geometric isomer, a tautomer, an N-oxide, a solvate, a pharmaceutically salt or a prodrug thereof, wherein:
each of $W_1$, $W_2$ and $W_3$ is independently N or $CR^c$;
Z is D, CN, $N_3$, or

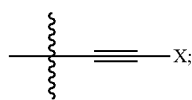

X is H, D, ($C_1$-$C_6$)alkyl, ($C_3$-$C_6$)cycloalkyl, ($C_3$-$C_6$) heterocyclyl, —($C_1$-$C_4$)alkylene-($C_3$-$C_6$)cycloalkyl, —($C_1$-$C_4$)alkylene-($C_3$-$C_6$)heterocyclyl, ($C_6$-$C_{10}$) aryl, or 5-10 membered heteroaryl comprising 1, 2, 3 or 4 heteroatoms independently selected from O, S and N, wherein each of the ($C_1$-$C_6$)alkyl, ($C_3$-$C_6$) cycloalkyl, ($C_3$-$C_6$)heterocyclyl, —($C_1$-$C_4$)alkylene-($C_3$-$C_6$)cycloalkyl, —($C_1$-$C_4$)alkylene-($C_3$-$C_6$)heterocyclyl, ($C_6$-$C_{10}$)aryl and 5-10 membered heteroaryl is optionally substituted with 1, 2, 3 or 4 substituents independently selected from D, F, Cl, Br, CN, $N_3$, $OR^a$, $SR^a$, $NR^aR^b$, —C(=O)$NR^aR^b$, ($C_1$-$C_6$)alkyl, ($C_1$-$C_6$)haloalkyl, ($C_2$-$C_6$)alkenyl, ($C_2$-$C_6$)alkynyl, —($C_1$-$C_4$)alkylene-CN, —($C_1$-$C_4$)

alkylene-OR$^a$, —(C$_1$-C$_4$)alkylene-NR$^a$R$^b$, (C$_6$-C$_{10}$)aryl, and 5-10 membered heteroaryl;

Y is (C$_1$-C$_6$)alkyl, (C$_3$-C$_6$)cycloalkyl, (C$_3$-C$_6$)heterocyclyl, —(C$_1$-C$_4$)alkylene-(C$_3$-C$_6$)cycloalkyl, —(C$_1$-C$_4$)alkylene-(C$_3$-C$_6$)heterocyclyl, (C$_2$-C$_6$)alkenyl, (C$_2$-C$_6$)alkynyl, (C$_6$-C$_{10}$)aryl, or 5-10 membered heteroaryl comprising 1, 2, 3 or 4 heteroatoms independently selected from O, S and N, wherein each of the (C$_1$-C$_6$)alkyl, (C$_3$-C$_6$)cycloalkyl, (C$_3$-C$_6$)heterocyclyl, —(C$_1$-C$_4$)alkylene-(C$_3$-C$_6$)cycloalkyl, —(C$_1$-C$_4$)alkylene-(C$_3$-C$_6$)heterocyclyl, (C$_2$-C$_6$)alkenyl, (C$_2$-C$_6$)alkynyl, (C$_6$-C$_{10}$)aryl and 5-10 membered heteroaryl is optionally substituted with 1, 2, 3 or 4 substituents independently selected from D, F, Cl, Br, CN, N$_3$, OR$^a$, SR$^a$, NR$^a$R$^b$, —C(=O)NR$^a$R$^b$, (C$_1$-C$_6$)alkyl, (C$_1$-C$_6$)haloalkyl, (C$_2$-C$_6$)alkenyl, (C$_2$-C$_6$)alkynyl, —(C$_1$-C$_4$)alkylene-CN, —(C$_1$-C$_4$)alkylene-OR$^a$, —(C$_1$-C$_4$)alkylene-NR$^a$R$^b$, (C$_6$-C$_{10}$)aryl, and 5-10 membered heteroaryl;

R$^1$ is H, D, Cl, OR$^a$, NR$^a$R$^b$, (C$_1$-C$_6$)aliphatic, or (C$_3$-C$_6$)cycloalkyl, wherein each of the (C$_1$-C$_6$)aliphatic and (C$_3$-C$_6$)cycloalkyl is optionally substituted with 1, 2, 3 or 4 substituents independently selected from D, F, Cl, CN, N$_3$, OR$^a$, SR$^a$, and NR$^a$R$^b$;

each R$^a$ and R$^b$ is independently H, (C$_1$-C$_6$)alkyl, (C$_3$-C$_6$)cycloalkyl, (C$_3$-C$_6$)heterocyclyl, (C$_6$-C$_{10}$)aryl, 5-10 membered heteroaryl comprising 1, 2, 3 or 4 heteroatoms independently selected from O, S and N, —(C$_1$-C$_4$)alkylene-(C$_6$-C$_{10}$)aryl, —(C$_1$-C$_4$)alkylene-(5-10 membered heteroaryl), or R$^a$ and R$^b$ are taken together with the nitrogen atom to which they are attached form a 3-8 membered heterocyclic ring, wherein each of the above substituents is optionally substituted with 1, 2, 3 or 4 substituents independently selected from D, F, Cl, CN, N$_3$, OH, NH$_2$, (C$_1$-C$_6$)alkoxy, and (C$_1$-C$_6$)alkylamino; and each R$^c$ is independently H, D, F, Cl, Br, I, N$_3$, CN, OH, NH$_2$, (C$_1$-C$_6$)alkyl, (C$_1$-C$_6$)alkoxy, (C$_1$-C$_6$)alkylamino, (C$_3$-C$_6$)cycloalkyl, (C$_3$-C$_6$)heterocyclyl, (C$_6$-C$_{10}$)aryl, or 5-10 membered heteroaryl comprising 1, 2, 3 or 4 heteroatoms independently selected from O, S and N, wherein each of the (C$_1$-C$_6$)alkyl, (C$_1$-C$_6$)alkoxy, (C$_1$-C$_6$)alkylamino, (C$_3$-C$_6$)cycloalkyl, (C$_3$-C$_6$)heterocyclyl, (C$_6$-C$_{10}$)aryl and 5-10 membered heteroaryl is optionally substituted with 1, 2, 3 or 4 substituents independently selected from D, F, Cl, CN, N$_3$, OH, NH$_2$, (C$_1$-C$_6$)alkyl, (C$_3$-C$_6$)cycloalkyl, (C$_1$-C$_6$)haloalkyl, (C$_1$-C$_6$)alkoxy, and (C$_1$-C$_6$)alkylamino.

2. The compound according to claim 1, wherein W$_1$ is N or CR$^c$; and each of W$_2$ and W$_3$ is independently CR$^c$.

3. The compound according to claim 1, wherein Z is CN, N$_3$, or

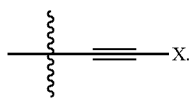

4. The compound according to claim 1, wherein X is H, D, (C$_1$-C$_6$)alkyl, (C$_3$-C$_6$)cycloalkyl, (C$_3$-C$_6$)heterocyclyl, —(C$_1$-C$_4$)alkylene-(C$_3$-C$_6$)cycloalkyl, or —(C$_1$-C$_4$)alkylene-(C$_3$-C$_6$) heterocyclyl, wherein each of the (C$_1$-C$_6$)alkyl, (C$_3$-C$_6$)cycloalkyl, (C$_3$-C$_6$)heterocyclyl, —(C$_1$-C$_4$)alkylene-(C$_3$-C$_6$)cycloalkyl and —(C$_1$-C$_4$)alkylene-(C$_3$-C$_6$)heterocyclyl is optionally substituted with 1, 2, 3 or 4 substituents independently selected from D, F, Cl, Br, CN, N$_3$, OR$^a$, SR$^a$, NR$^a$R$^b$, —C(=O)NR$^a$R$^b$, (C$_1$-C$_3$)alkyl, (C$_1$-C$_3$)haloalkyl, (C$_2$-C$_4$)alkenyl, and (C$_2$-C$_4$)alkynyl.

5. The compound according to claim 1, wherein Y is (C$_1$-C$_6$)alkyl, (C$_3$-C$_6$)cycloalkyl, (C$_2$-C$_6$)alkenyl, (C$_2$-C$_6$)alkynyl, (C$_6$-C$_{10}$)aryl, or 5-10 membered heteroaryl comprising 1, 2, 3 or 4 heteroatoms independently selected from O, S and N, wherein each of the (C$_1$-C$_6$)alkyl, (C$_3$-C$_6$)cycloalkyl, (C$_2$-C$_6$)alkenyl, (C$_2$-C$_6$)alkynyl, (C$_6$-C$_{10}$)aryl and 5-10 membered heteroaryl is optionally substituted with 1, 2, 3 or 4 substituents independently selected from D, F, Cl, Br, CN, N$_3$, OR$^a$, SR$^a$, NR$^a$R$^b$, —C(=O)NR$^a$R$^b$, (C$_1$-C$_3$)alkyl, (C$_1$-C$_3$)haloalkyl, (C$_2$-C$_4$)alkynyl, (C$_6$-C$_{10}$)aryl, and 5-10 membered heteroaryl.

6. The compound according to claim 1, wherein R$^1$ is H, D, Cl, CH$_3$, CH$_2$CH$_3$, CF$_3$, CH$_2$CF$_3$, OCH$_3$, or OCH$_2$CH$_3$.

7. The compound according to claim 1, wherein each R$^c$ is independently H, D, F, Cl, N$_3$, CN, NH$_2$, (C$_1$-C$_3$)alkyl, (C$_1$-C$_3$)alkoxy, (C$_1$-C$_3$)alkylamino, (C$_3$-C$_6$)cycloalkyl, or (C$_3$-C$_6$)heterocyclyl, wherein each of the (C$_1$-C$_3$)alkyl, (C$_1$-C$_3$)alkoxy, (C$_1$-C$_3$)alkylamino, (C$_3$-C$_6$)cycloalkyl and (C$_3$-C$_6$)heterocyclyl is optionally substituted with 1, 2, 3 or 4 substituents independently selected from D, F, CN, N$_3$, OH, NH$_2$, (C$_1$-C$_3$)alkyl, (C$_3$-C$_6$)cycloalkyl, and (C$_1$-C$_3$)haloalkyl.

8. The compound according to claim 1 having one of the following structures:

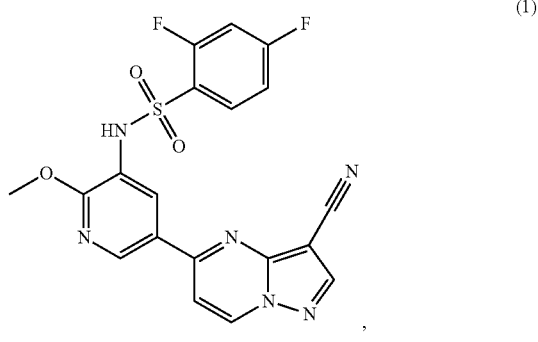

(1)

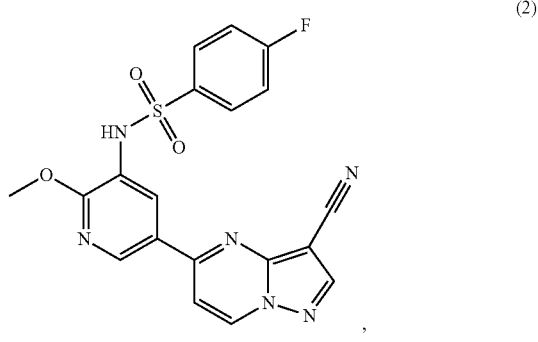

(2)

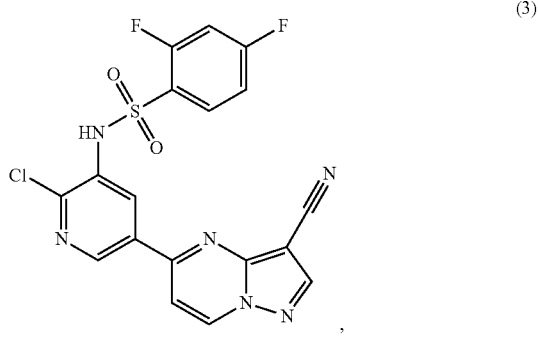

(3)

-continued
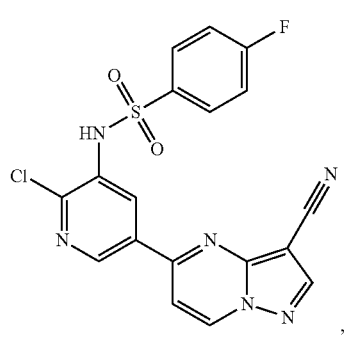
(4)
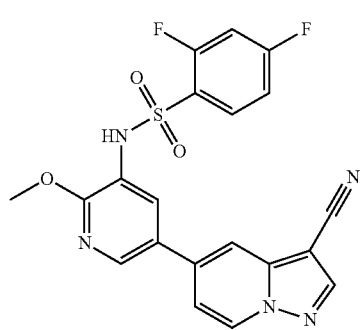
(5)
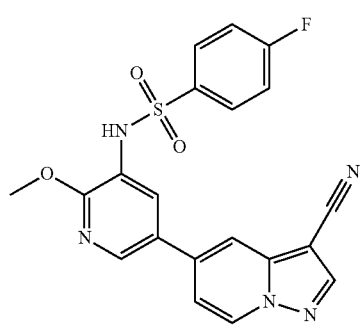
(6)
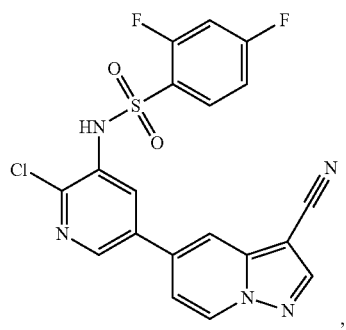
(7)
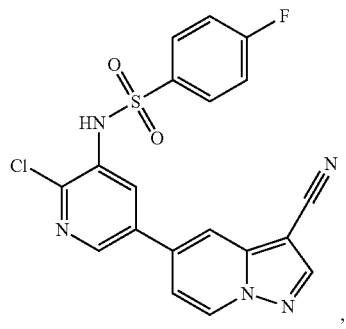
(8)
-continued
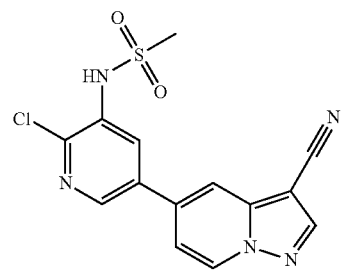
(9)
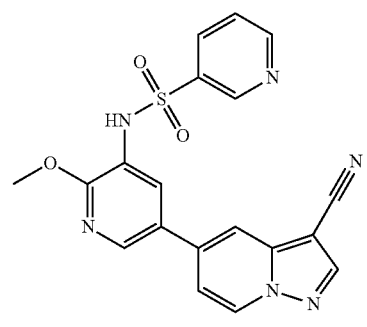
(10)
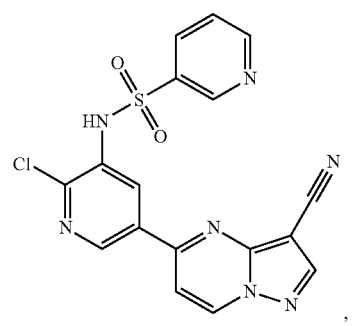
(11)
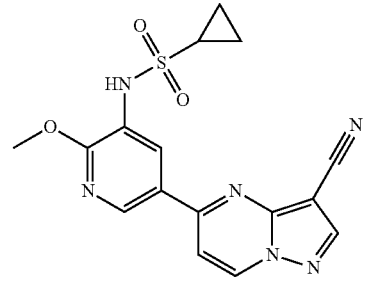
(12)
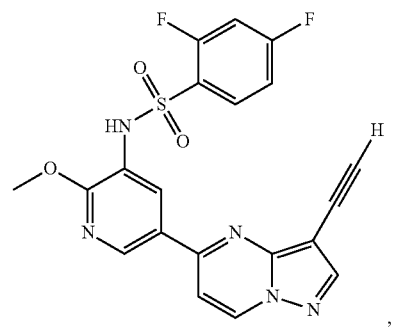
(13)

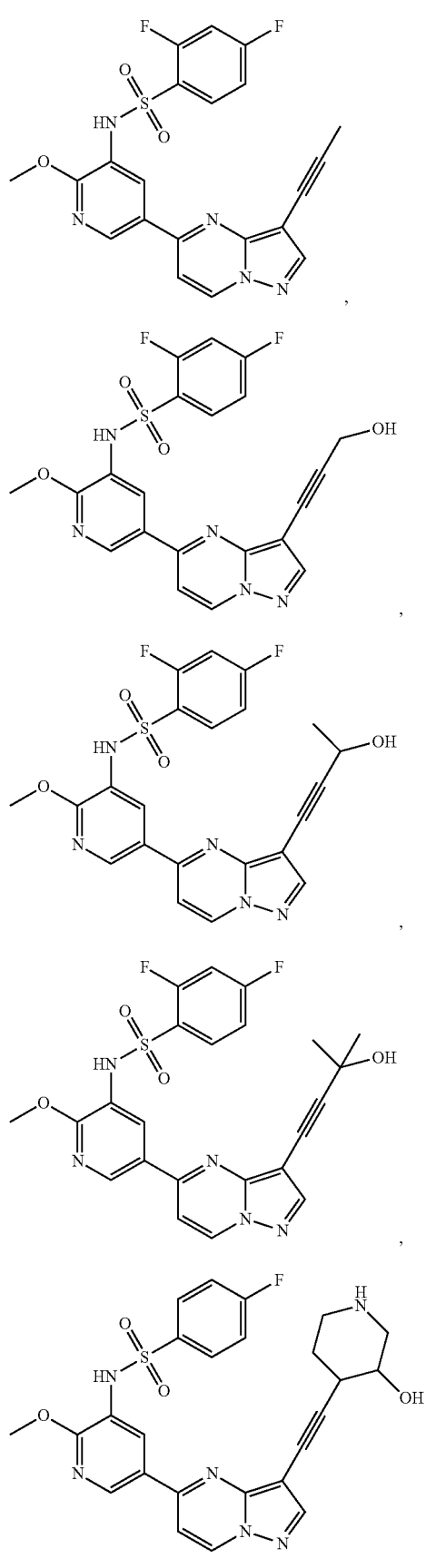
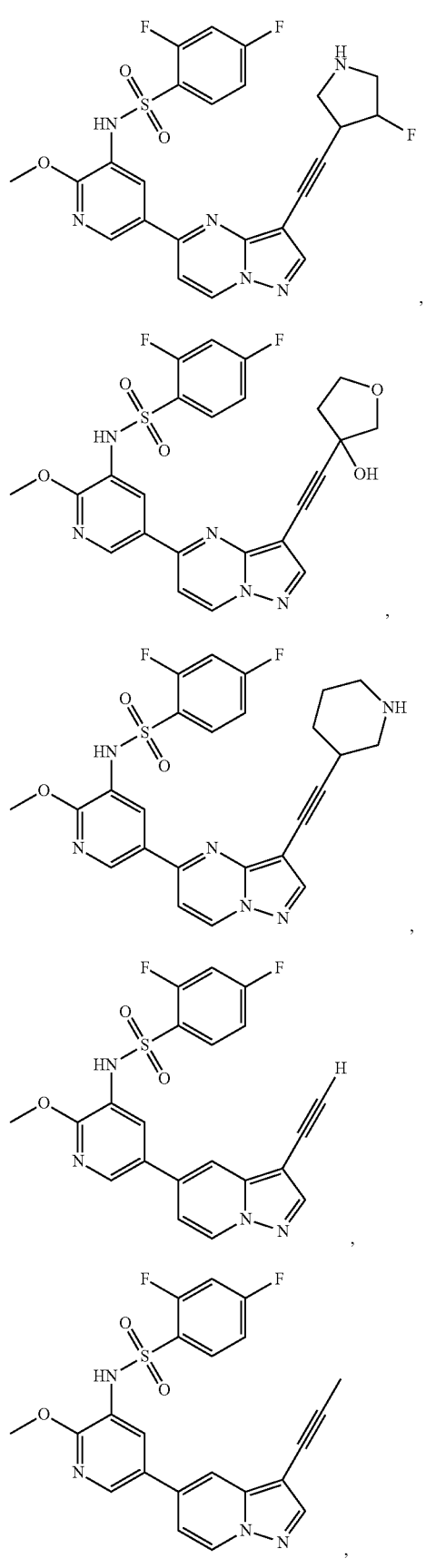

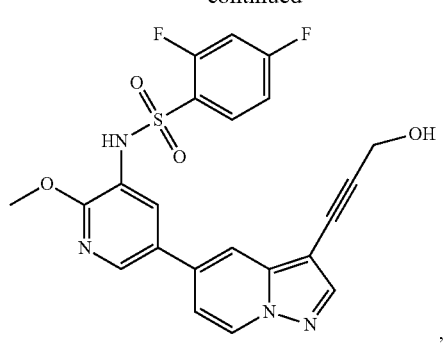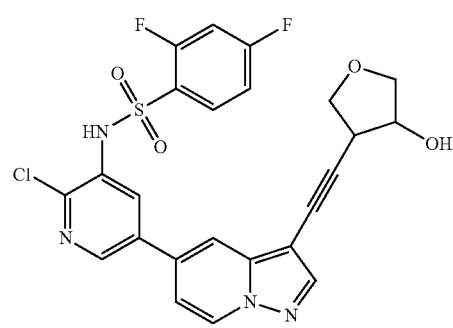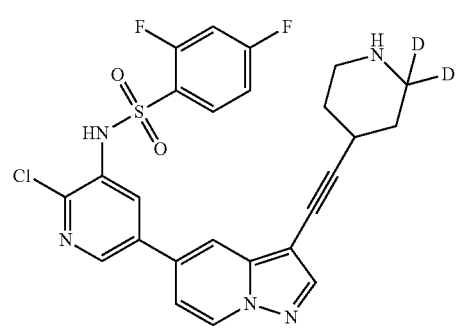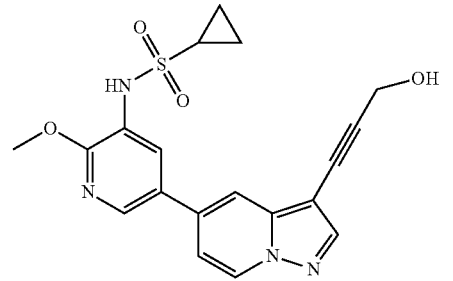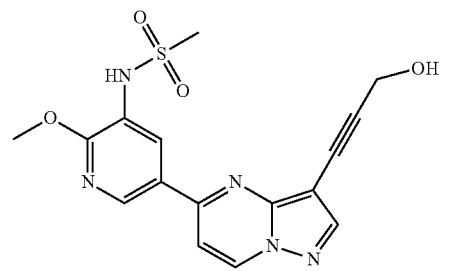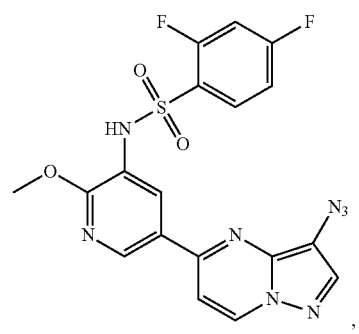

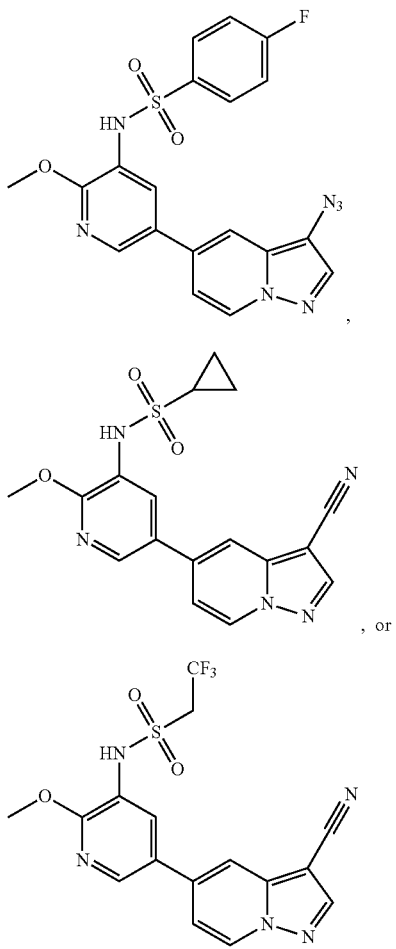

9. A pharmaceutical composition comprising the compound according to claim 1, and a pharmaceutically acceptable carrier, excipient, diluent, adjuvant, vehicle or a combination thereof.

10. The pharmaceutical composition according to claim 9 further comprising an additional therapeutic agent selected from a chemotherapeutic agent, an anti-proliferative agent, an agent for treating atherosclerosis, an agent for treating lung fibrosis or a combination thereof.

11. The pharmaceutical composition according to claim 10, wherein the additional therapeutic agent is chlorambucil, melphalan, cyclophosphamide, ifosfamide, busulfan, carmustine, lomustine, streptozocin, cisplatin, carboplatin, oxaliplatin, dacarbazine, temozolomide, procarbazine, methotrexate, fluorouracil, cytarabine, gemcitabine, mercaptopurine, fludarabine, vinblastine, vincristine, vinorelbine, paclitaxel, docetaxel, topotecan, irinotecan, etoposide, trabectedin, dactinomycin, doxorubicin, epirubicin, daunorubicin, mitoxantrone, bleomycin, mitomycin, ixabepilone, tamoxifen, flutamide, gonadorelin analogues, megestrol, prednidone, dexamethasone, methylprednisolone, thalidomide, interferon alfa, leucovorin, sirolimus, temsirolimus, everolimus, afatinib, alisertib, amuvatinib, apatinib, axitinib, bortezomib, bosutinib, brivanib, cabozantinib, cediranib, crenolanib, crizotinib, dabrafenib, dacomitinib, danusertib, dasatinib, dovitinib, erlotinib, foretinib, ganetespib, gefitinib, ibrutinib, icotinib, imatinib, iniparib, lapatinib, lenvatinib, linifanib, linsitinib, masitinib, momelotinib, motesanib, neratinib, nilotinib, niraparib, oprozomib, olaparib, pazopanib, pictilisib, ponatinib, quizartinib, regorafenib, rigosertib, rucaparib, ruxolitinib, saracatinib, saridegib, sorafenib, sunitinib, tasocitinib, telatinib, tivantinib, tivozanib, tofacitinib, trametinib, vandetanib, veliparib, vemurafenib, vismodegib, volasertib, alemtuzumab, bevacizumab, brentuximab vedotin, catumaxomab, cetuximab, denosumab, gemtuzumab, ipilimumab, nimotuzumab, ofatumumab, panitumumab, ramucirumab, rituximab, tositumomab, trastuzumab, or a combination thereof.

12. A method of treating or lessening the severity of a proliferative disorder in a patient by administering to the patient the compound according to claim 1, wherein the proliferative disorder is glioblastoma.

13. A method of treating or lessening the severity of a proliferative disorder in a patient by administering to the patient the pharmaceutical composition according to claim 9, wherein the proliferative disorder is glioblastoma.

14. A method of inhibiting the activity of a protein kinase in a biological sample comprising contacting a biological sample with the compound according to claim 1, wherein the protein kinase is PI3K, mTOR or a combination thereof.

15. A method of inhibiting the activity of a protein kinase in a biological sample comprising contacting a biological sample with the pharmaceutical composition according to claim 9, wherein the protein kinase is PI3K, mTOR or a combination thereof.

* * * * *